United States Patent
Shalek et al.

(10) Patent No.: US 11,865,168 B2
(45) Date of Patent: Jan. 9, 2024

(54) COMPOSITIONS AND METHODS FOR TREATING BACTERIAL INFECTIONS

(71) Applicants: Massachusetts Institute of Technology, Cambridge, MA (US); The United States of America, as represented by The Secretary, Department of Health & Human Services, Bethesda, MD (US); University of Pittsburgh—Of The Commonwealth System of Higher Education, Pittsburgh, PA (US)

(72) Inventors: Alexander K. Shalek, Cambridge, MA (US); Travis Hughes, Cambridge, MA (US); Marc H. Wadsworth, Cambridge, MA (US); Robert Seder, Bethesda, MD (US); Mario Roederer, Bethesda, MD (US); Joanne L. Flynn, Pittsburgh, PA (US); Patricia Darrah, Bethesda, MD (US)

(73) Assignees: Massachusetts Institute of Technology, Cambridge, MA (US); The United States of America, as represented by The Secretary, Department of Health & Human Services, Bethesda, MD (US); University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/137,481

(22) Filed: Dec. 30, 2020

(65) Prior Publication Data
US 2021/0213126 A1    Jul. 15, 2021

Related U.S. Application Data

(60) Provisional application No. 62/954,998, filed on Dec. 30, 2019.

(51) Int. Cl.
| | | |
|---|---|---|
| *A61K 39/02* | (2006.01) | |
| *A61K 39/04* | (2006.01) | |
| *A61P 31/06* | (2006.01) | |
| *A61K 39/00* | (2006.01) | |

(52) U.S. Cl.
CPC .............. *A61K 39/04* (2013.01); *A61P 31/06* (2018.01); *A61K 2039/54* (2013.01)

(58) Field of Classification Search
CPC ........ A61K 39/00; A61K 39/02; A61K 39/04; A61K 47/6813; A61K 31/06
USPC .................. 424/9.1, 9.2, 234.1, 248.1, 278.1
See application file for complete search history.

(56) References Cited

U.S. PATENT DOCUMENTS

| | | |
|---|---|---|
| 5,641,870 A | 6/1997 | Rinderknecht et al. |
| 5,811,097 A | 9/1998 | Allison et al. |
| 5,858,358 A | 1/1999 | June et al. |
| 5,883,223 A | 3/1999 | Gray |
| 6,040,177 A | 3/2000 | Riddell et al. |
| 6,352,694 B1 | 3/2002 | June et al. |
| 6,534,055 B1 | 3/2003 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,144,575 B2 | 12/2006 | June et al. |
| 7,175,843 B2 | 2/2007 | June et al. |
| 7,232,566 B2 | 6/2007 | June et al. |
| 7,572,631 B2 | 8/2009 | Berenson et al. |
| 8,034,334 B2 | 10/2011 | Dudley et al. |
| 8,088,379 B2 | 1/2012 | Robbins et al. |
| 8,637,307 B2 | 1/2014 | June et al. |
| 8,697,854 B2 | 4/2014 | Schendel et al. |
| 2004/0224402 A1 | 11/2004 | Bonyhadi et al. |

(Continued)

FOREIGN PATENT DOCUMENTS

| | | |
|---|---|---|
| EP | 0 404 097 B1 | 9/1996 |
| WO | 93/11161 A1 | 6/1993 |

(Continued)

OTHER PUBLICATIONS

McNeil Jr, D (The New York Times. Jan. 1, 2020; Global Health "New Injection Method Makes an Old TB Vaccine Far More Powerful", pp. 1-2.*
Barclay et al (Infect. Immun. 1970. 2(5): 574-82).*
Li et al (Eur. Review for Med. and Pharma. Sci. 2012. 16:2029-2036).*
Li et al (Molecular Med. Reports. 2015. 12: 3073-3080).*
Hu et al (Molecular Therapy. May 2017. 25(5): 1222-1233).*
Bertholet et al (Science Translational Med. Oct. 2010. 2(53): 1-10).*
Booty, et al., "IL-21 Signaling is Essential for Optimal Host Resistance Against Mycobacterium Tuberculosis Infection", Scientific Reports, vol. 6, No. 36720, Nov. 7, 2016, 13 pages.

(Continued)

*Primary Examiner* — Jennifer E Graser
(74) *Attorney, Agent, or Firm* — F. Brent Nix, Esq.; Johnson, Marcou, Isaacs & Nix, LLC; Michael B. Scher, Esq.

(57) ABSTRACT

Provided herein are compositions and methods for therapeutic and/or prophylactic treatment of an intracellular bacterial infection in a subject in need thereof, comprising one or more modulating agents, wherein the one or more modulating agents increase expression of IFNγ, IL-2, TNF, and/or IL-17 in systemic and/or lung T cells. In some embodiments, the increase of expression of IFNγ, IL-2, TNF, and/or IL-17 occurs in lung T cells. The lung T cells can be lung resident T cells or systemic T cells that are recruited to the lung. In some embodiments, the T cells are CD4+ and/or CD8+ T cells. In some embodiments, the intracellular bacterial infection is a *Mycobacterium tuberculosis* (MTB) infection.

2 Claims, 52 Drawing Sheets

(56) References Cited

U.S. PATENT DOCUMENTS

| | | | |
|---|---|---|---|
| 2011/0117133 A1* | 5/2011 | Shafferman | A61P 31/06 424/248.1 |
| 2012/0244133 A1 | 9/2012 | Rosenberg et al. | |
| 2013/0071414 A1 | 3/2013 | Dotti et al. | |

FOREIGN PATENT DOCUMENTS

| | | |
|---|---|---|
| WO | 96/40281 A2 | 12/1996 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2010/101870 A1 | 9/2010 |
| WO | 2011/146862 A1 | 11/2011 |
| WO | 2013/039889 A1 | 3/2013 |
| WO | 2013/040371 A2 | 3/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/059173 A2 | 4/2014 |
| WO | 2014/083173 A1 | 6/2014 |
| WO | 2014/172606 A1 | 10/2014 |
| WO | 2014/184744 A1 | 11/2014 |
| WO | 2014/191128 A1 | 12/2014 |
| WO | 2016/191756 A1 | 12/2016 |

OTHER PUBLICATIONS

Orr, et al., "Interferon γ and Tumor Necrosis Factor Are Not Essential Parameters of CD4[+] T-Cell Responses for Vaccine Control of Tuberculosis", The Journal of Infectious Diseases, vol. 212, Aug. 1, 2015, 495-504.

Quiroga, et al., "Inducible Costimulator: A Modulator of IFN— Production in Human Tuberculosis", The Journal of Immunology, vol. 176, No. 10, doi:10.4049/jimmunol.176.10.5965, 2006, 5965-5974.

Sakai, et al., "CD4 T Cell-Derived IFN-γ Plays a Minimal Role in Control of Pulmonary Mycobacterium tuberculosis Infection and Must be Actively Repressed by PD-1 to Prevent Lethal Disease", Plos Pathogens, vol. 12, No. e1005667, DOI:10.1371/journal.ppat. 1005667, May 31, 2016, 22 pages.

Sallin, et al., "Host Resistance to Pulmonary Mycobacterium Tuberculosis Infection Requires CD153 Expression", Nature Microbiology, 2018, 11 pages.

Song, et al., "The Activation and Regulation of IL-17 Receptor Mediated Signaling", Cytokine, vol. 62, No. 2, doi:10.1016/j.cyto. 2013.03.014, 2013, 175-182.

Spolski, et al., "Biology and Regulation of IL-2: From Molecular Mechanisms to Human Therapy", Nature Reviews Immunology, vol. 18, doi:10.1038/s41577-018-0046-y, Oct. 2018, 648-659.

* cited by examiner

| Cohort | | BCG Dose (CFU) | | | Duration | Challenge | Number of Animals Per Arm | | | | | | | Total |
|---|---|---|---|---|---|---|---|---|---|---|---|---|---|---|
| | | Low Dose ID | High Dose ID | High Dose IV, AE, EB | Time to Challenge (Weeks) | Mtb Dose (CFU) | ID low (n) | ID high (n) | IV (n) | AE (n) | AE/ID (n) | EB (n) | Unvax (n) | (n) |
| Immunology & Challenge | 1 | 3.5×10⁵ | - | 5.2×10⁷ | 27 | 4 | 3 | - | 2 | 3 | 2 | - | - | 10 |
| | 2 | 3.1×10⁵ | 2.9×10⁷ | 3.7×10⁷ | 29 | 16 | 2 | - | 3 | 2 | 3 | - | - | 10 |
| | 3 | 3.1×10⁵ | 2.9×10⁷ | 3.7×10⁷ | 22/26 | 8 | 2 | 2 | 2 | 2 | 2 | - | - | 10 |
| | 4 | 2.1×10⁶ | 4.7×10⁷ | 3.7×10⁷ | 24/28 | 11 | 2 | 2 | 2 | 2 | 2 | - | - | 10 |
| Immunology Only | 5a | 1.6×10⁶ | 1.9×10⁷ | 2.5×10⁷ | 37/41 | 16 | 0 | 2 | 1 | 0 | 1 | - | 2 | 6 |
| | 5b | 2.2×10⁶ | 2.2×10⁷ | 1.2×10⁷ | 38/42 | 36 | 1 | 2 | 0 | 1 | 0 | - | 2 | 6 |
| | 5c | 1.5×10⁶ | 4.3×10⁷ | 2.4×10⁷ | N/A | N/A | 3 | 3 | 3 | 3 | 3 | - | - | 15 |
| hCD45 | 6 | - | 7.4×10⁷ | 3.6×10⁷ | N/A | N/A | 1 | 1 | 1 | - | 1 | - | - | 4 |
| | | | | | N/A | N/A | 1 | 1 | 1 | - | 1 | - | - | 4 |
| | | | | | N/A | N/A | 2 | 2 | 2 | 2 | - | - | - | 8 |
| | | | | | N/A | N/A | - | 2 | 2 | 2 | - | 2 | - | 8 |

| | | BCG Dose (CFU) | | | | | | | | | | | | |
|---|---|---|---|---|---|---|---|---|---|---|---|---|---|---|
| | | Low Dose ID | High Dose IV or AE | Medium Dose IV or AE | Low Dose AE | | | | | | | | | |
| Pilot Immunology | Pilot a | 3.7×10⁵ | 5.6×10⁶ (AE) | 5.7×10⁶ (AE) | 6.0×10⁵ | | 3 | - | - | - | 9 | - | - | 12 |
| | Pilot b | - | 2.1×10⁷ (AE) | 2.7×10⁶ (AE) | - | | | | - | 6 | - | - | - | 6 |
| | Pilot c | - | 3.5×10⁵ (IV) | 5.8×10⁵ (IV) | - | | | | 6 | - | - | - | - | 6 |
| NHP (BCG or Unvax) | | | | | | | 20 | 17 | 25 | 23 | 24 | 2 | 4 | 115 |
| NHP (TB Challenge) | | | | | | | 10 | 8 | 10 | 10 | 10 | - | 4 | 52 |

FIG. 3A

FIG. 4A
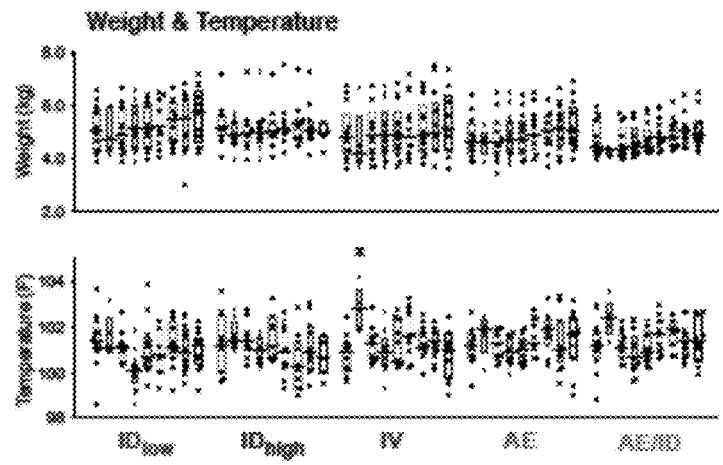
FIG. 4B
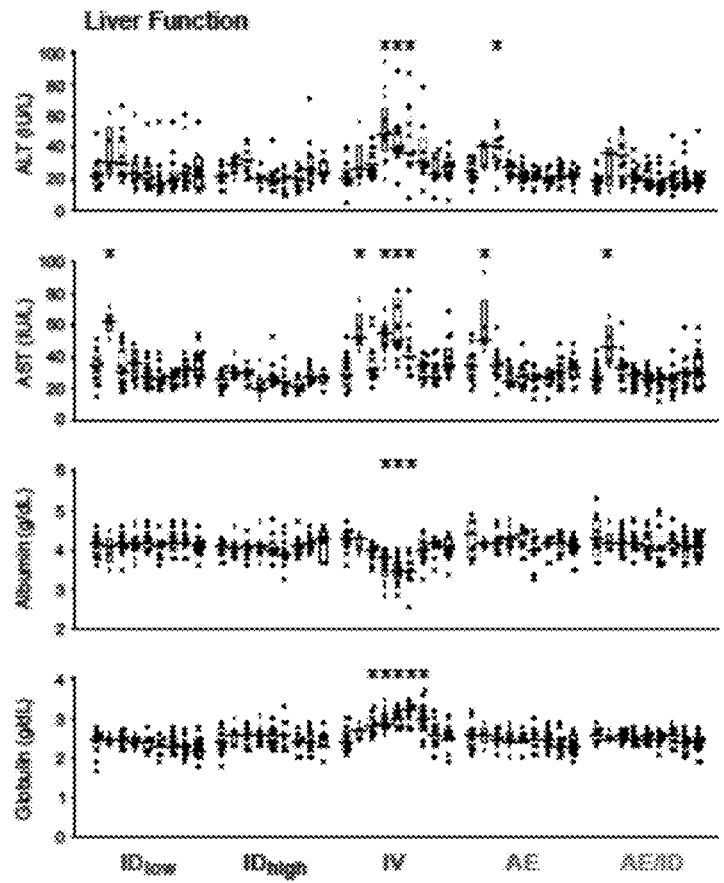
FIG. 4A-4B

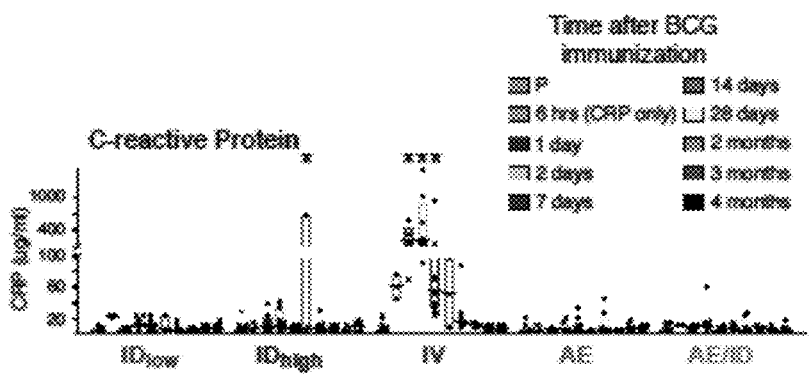
FIG. 4C
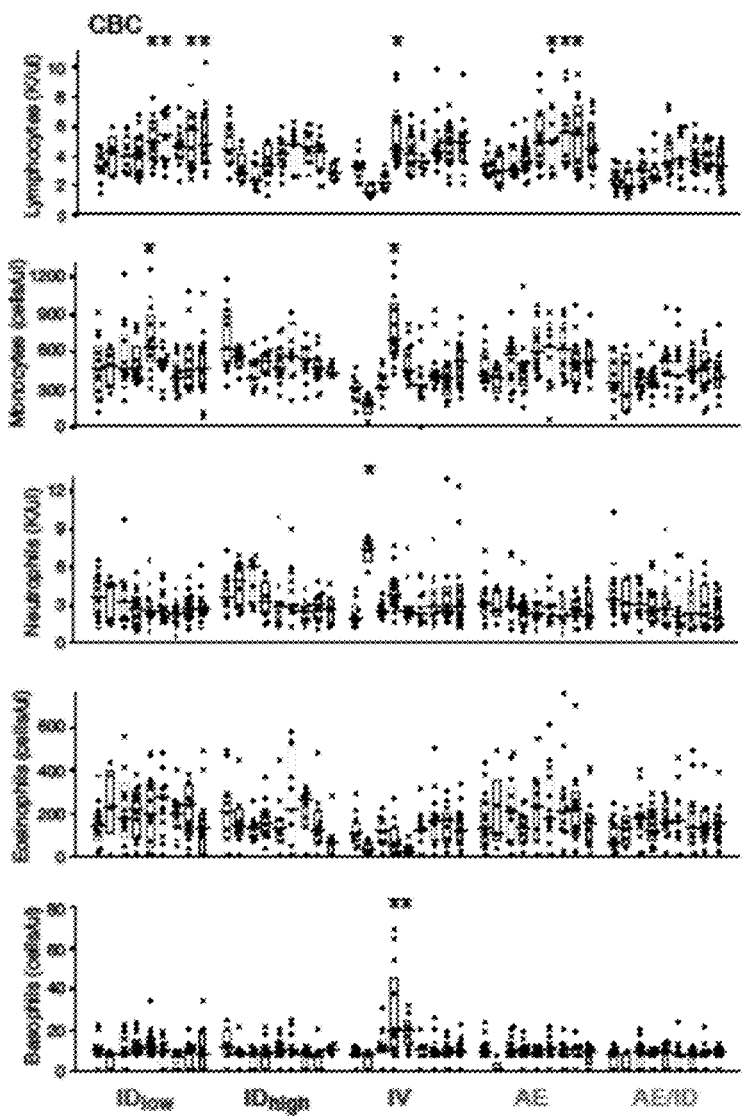
FIG. 4D
FIG. 4C-4D

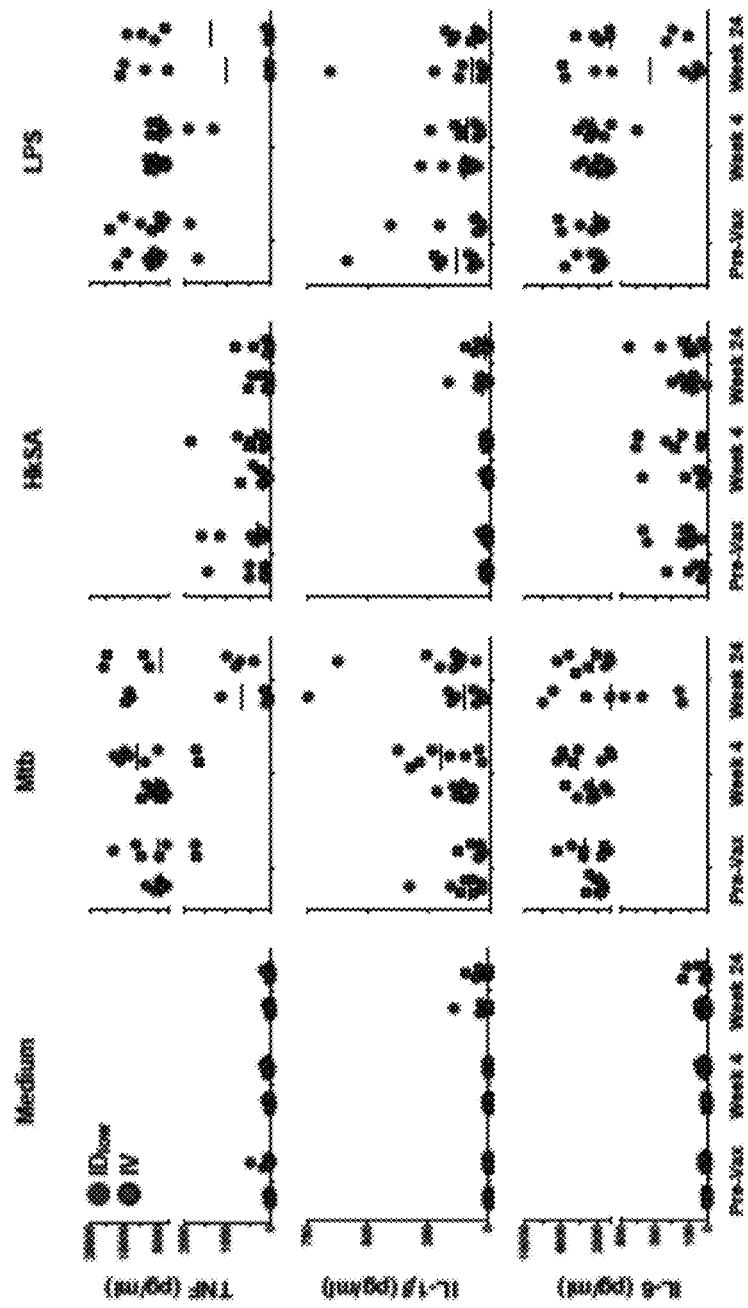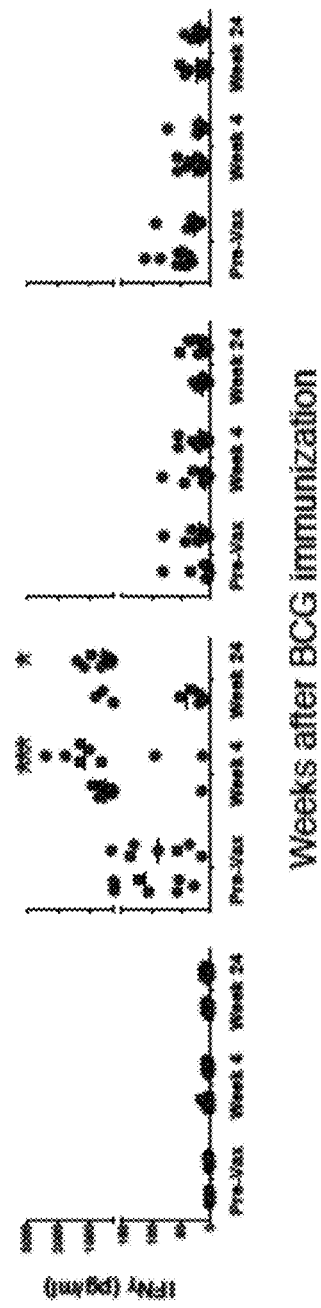
FIG. 8A
FIG. 8B

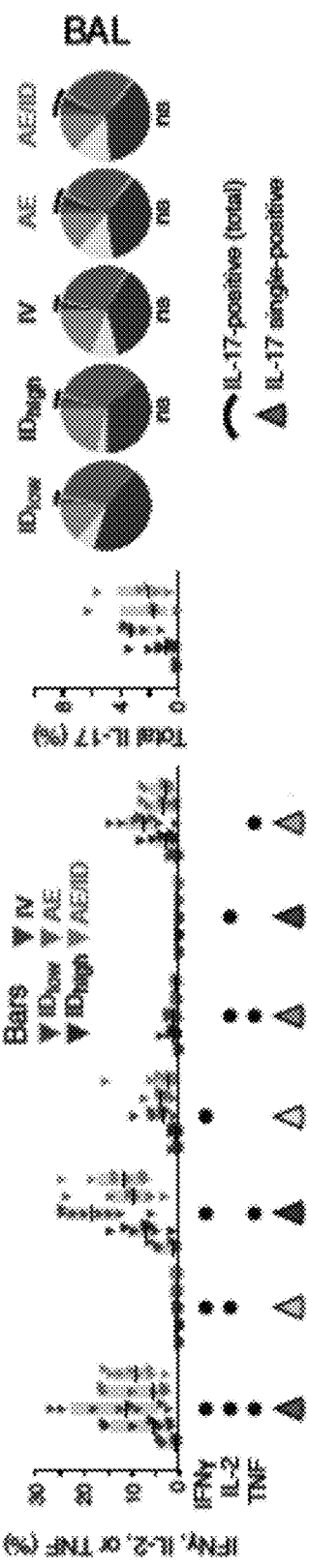
FIG. 9E
FIG. 9F
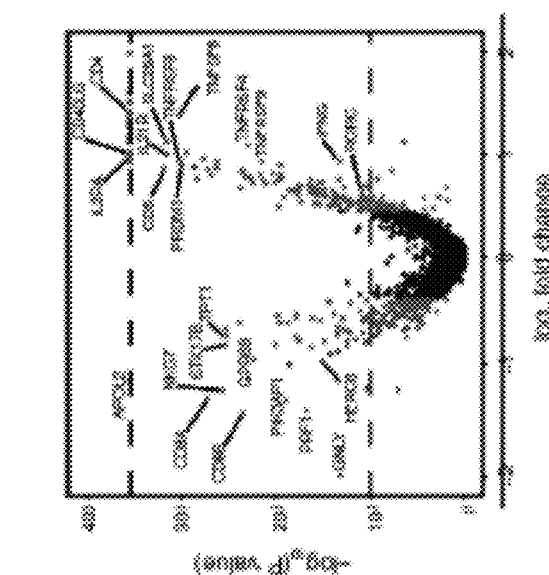
FIG. 9H
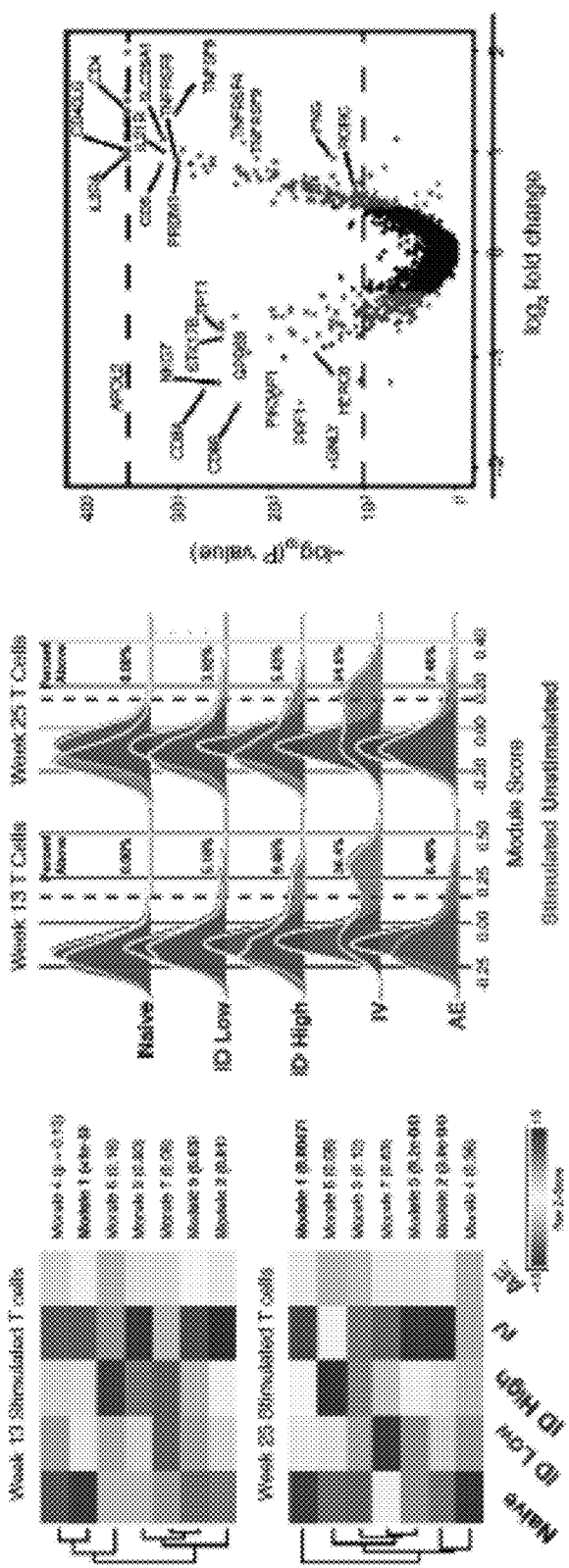
FIG. 9G

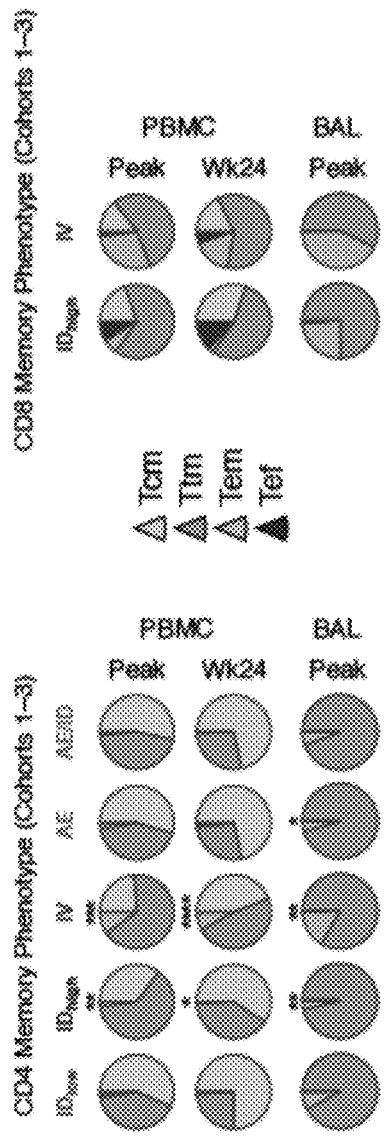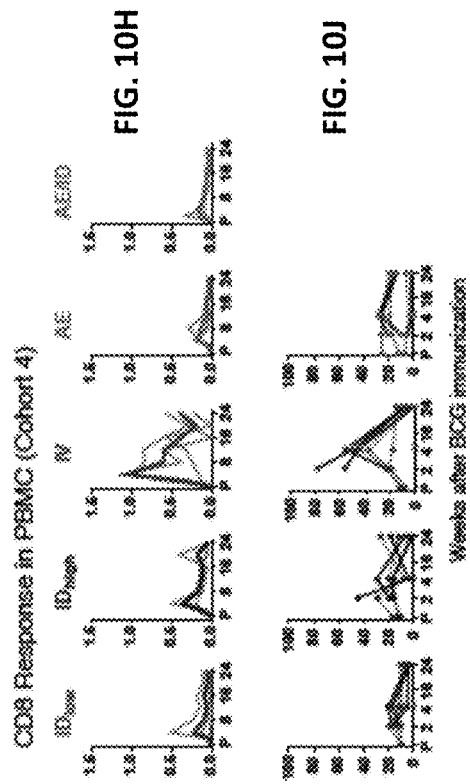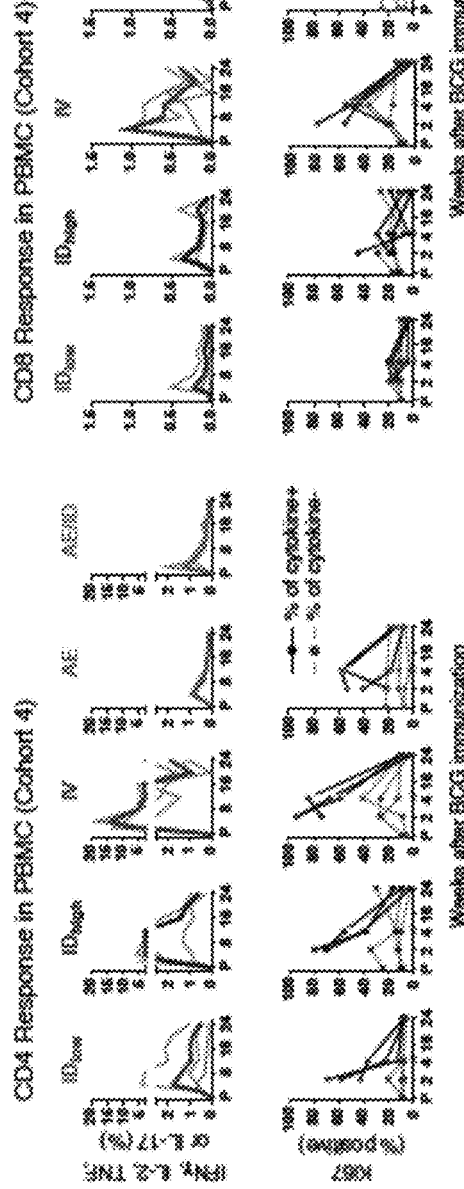

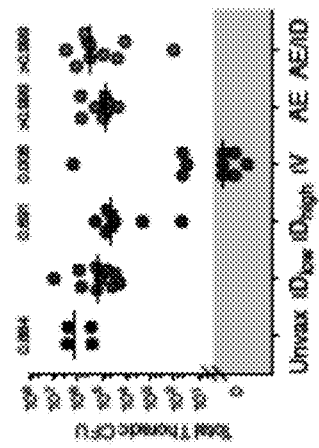
FIG. 18A
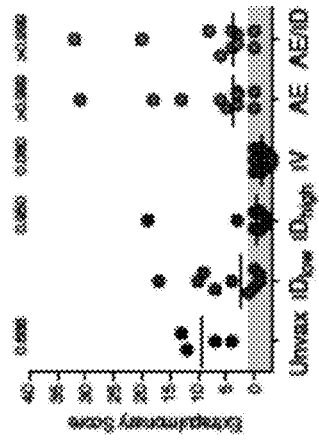
FIG. 18B
FIG. 18C
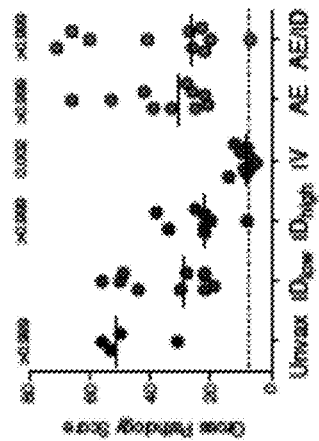
FIG. 18D
FIG. 18E
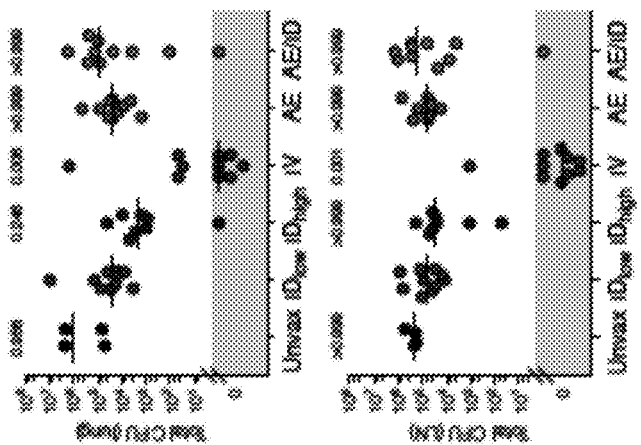
FIG. 18F

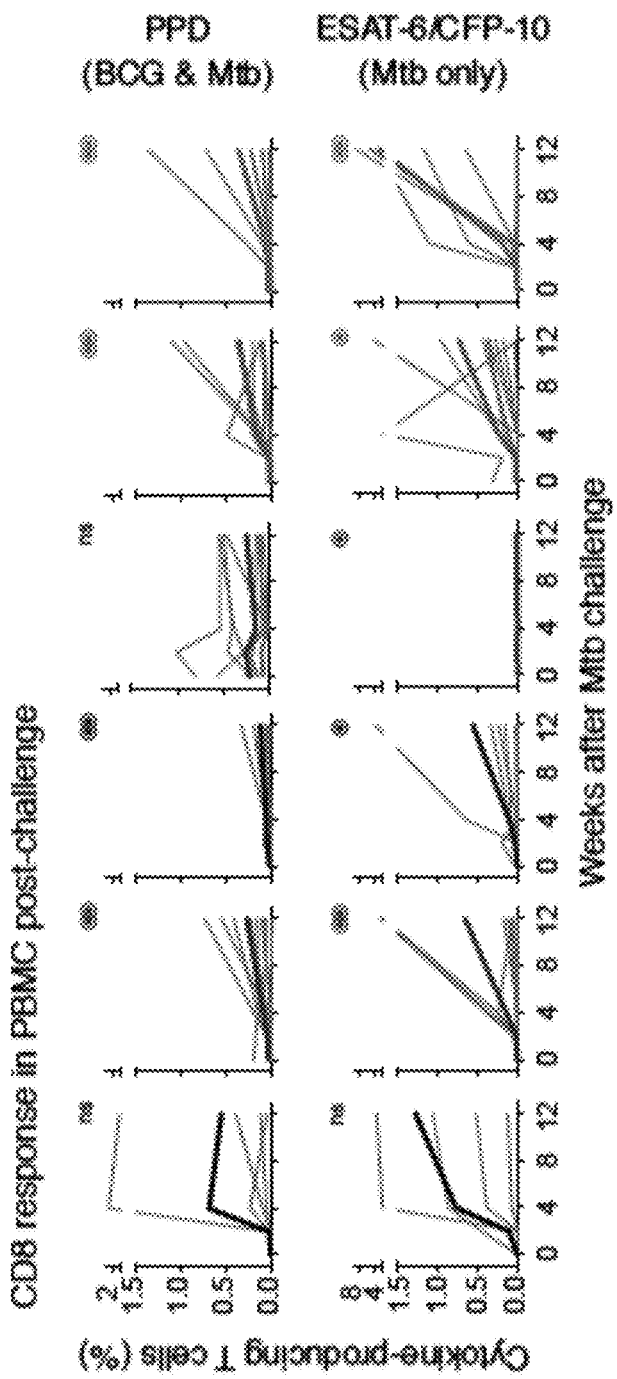
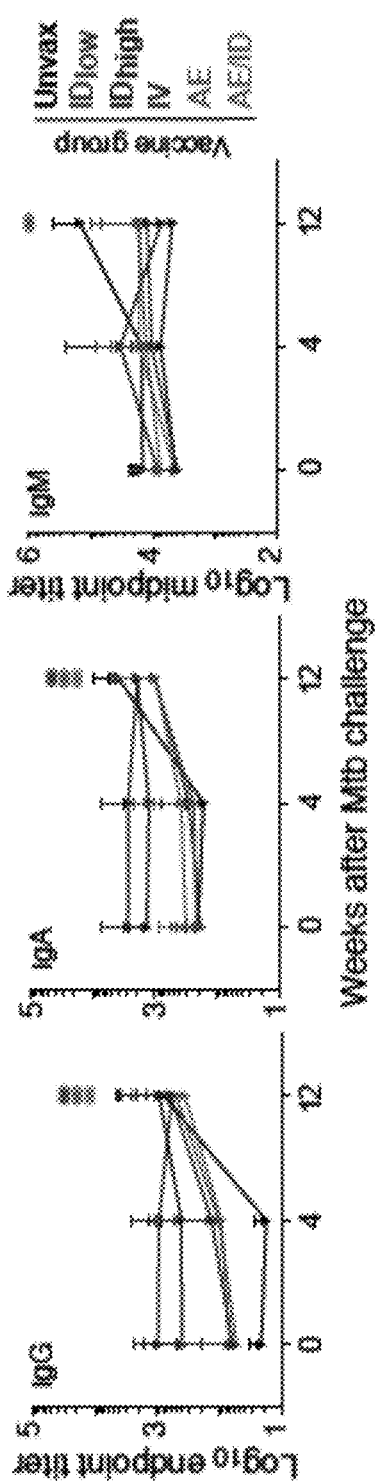
FIG. 19B
FIG. 19C

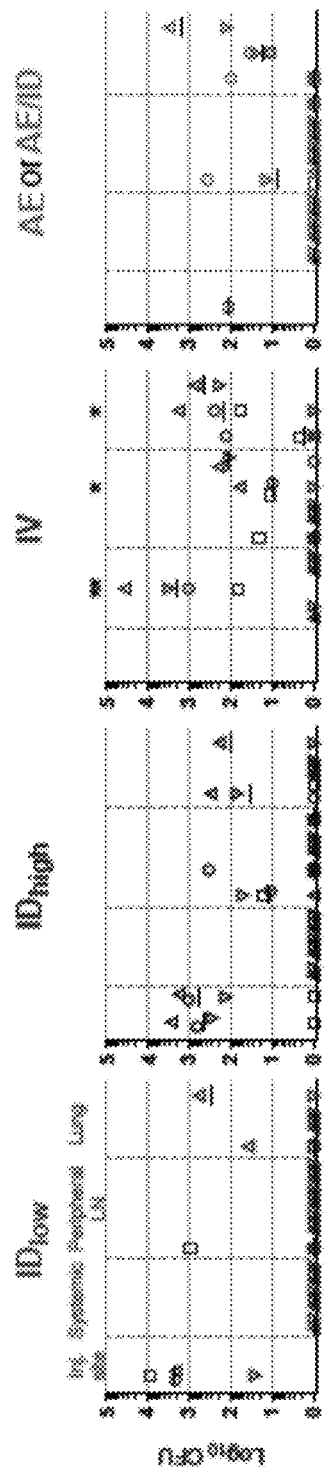
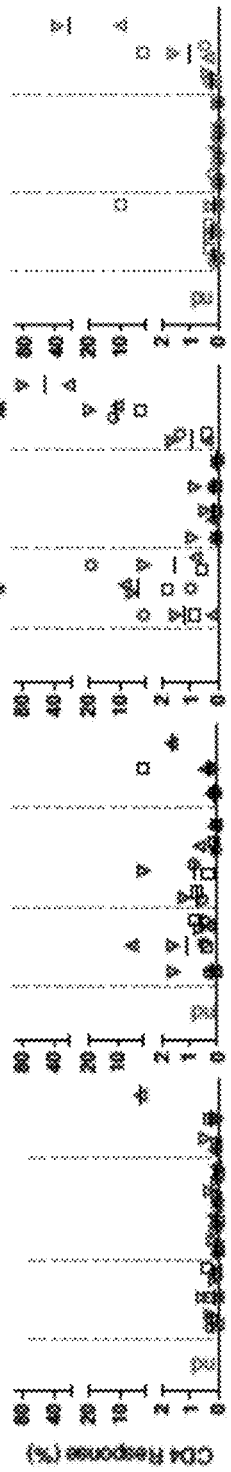
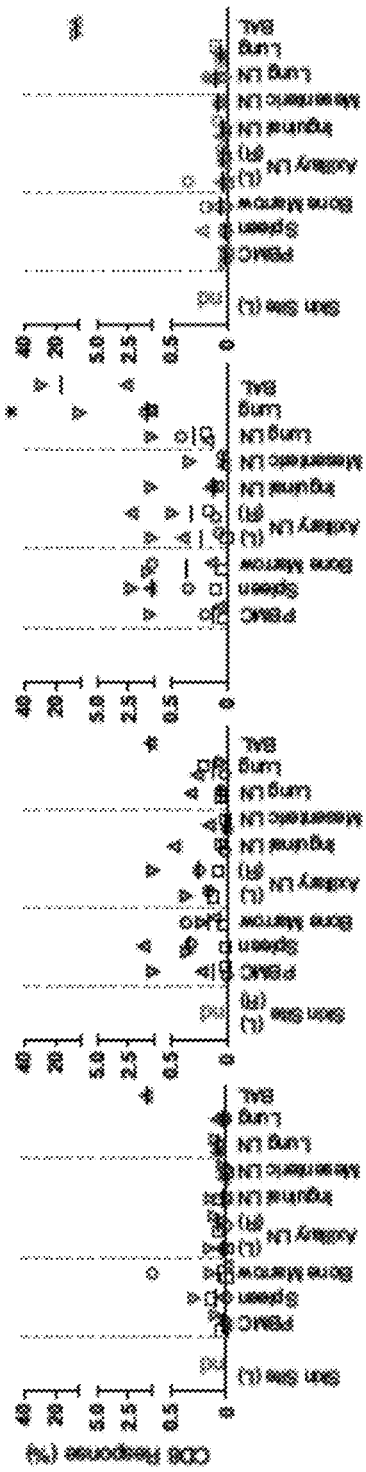
FIG. 20A
FIG. 20B
FIG. 20C

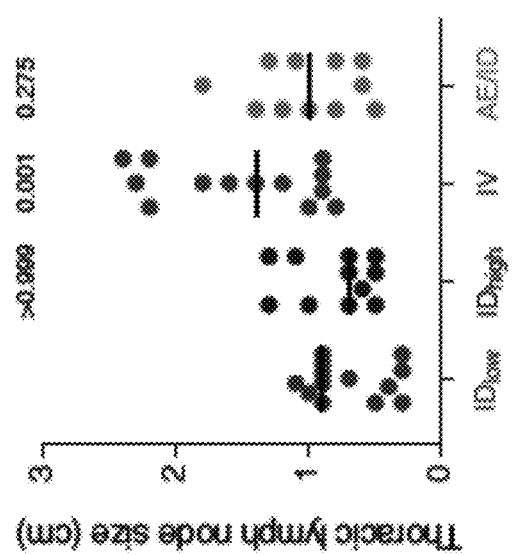
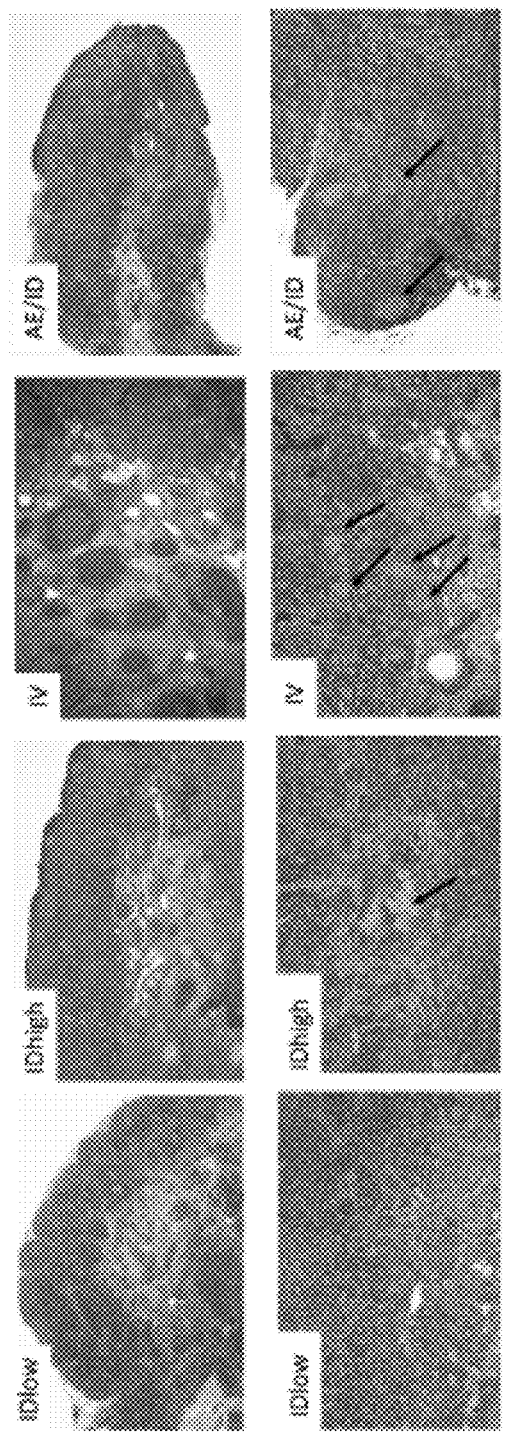
FIG. 21A
FIG. 21B
FIG. 21C

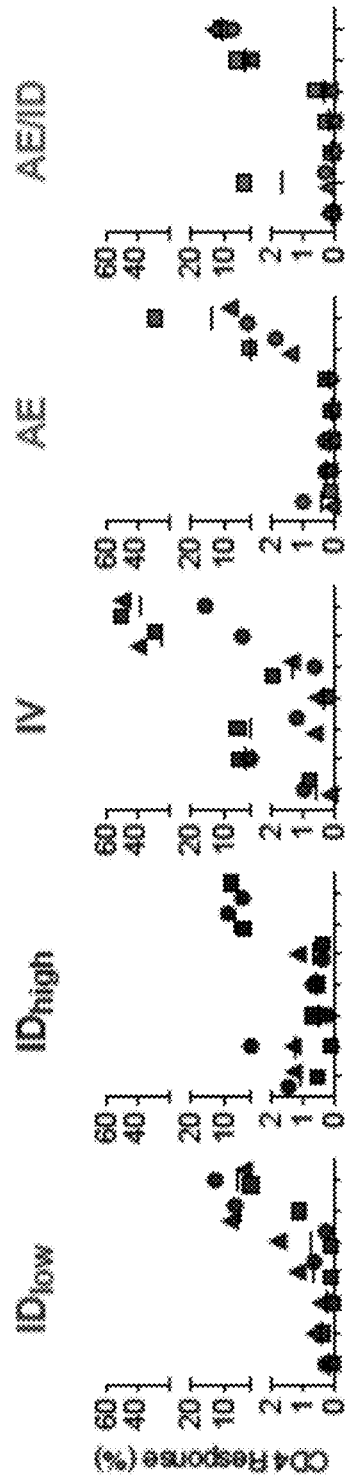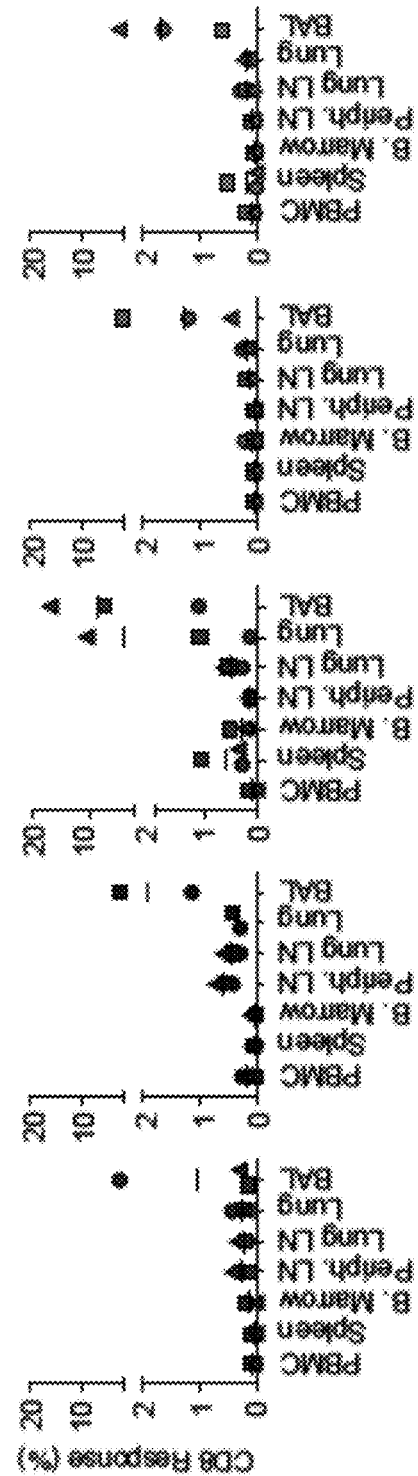
FIG. 22A
FIG. 22B

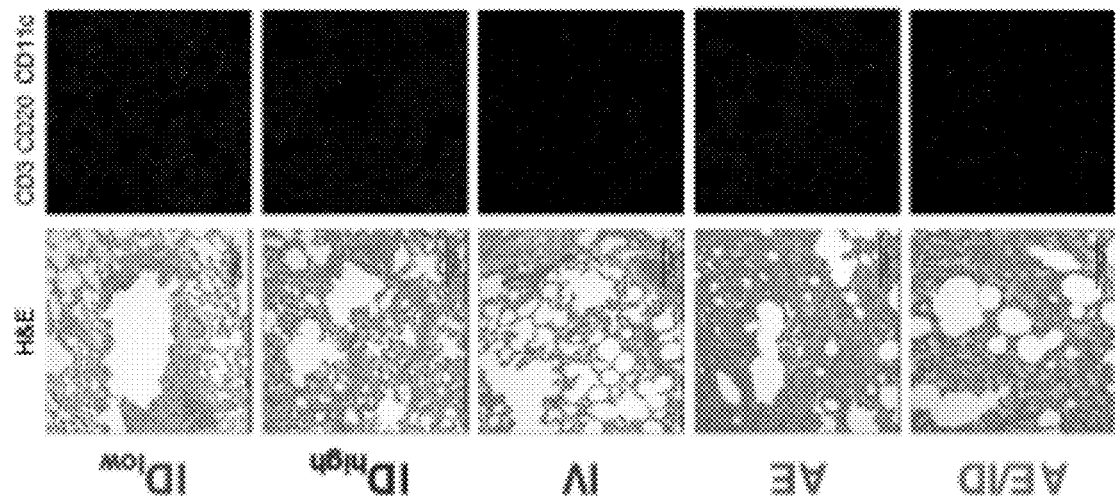
FIG. 22D
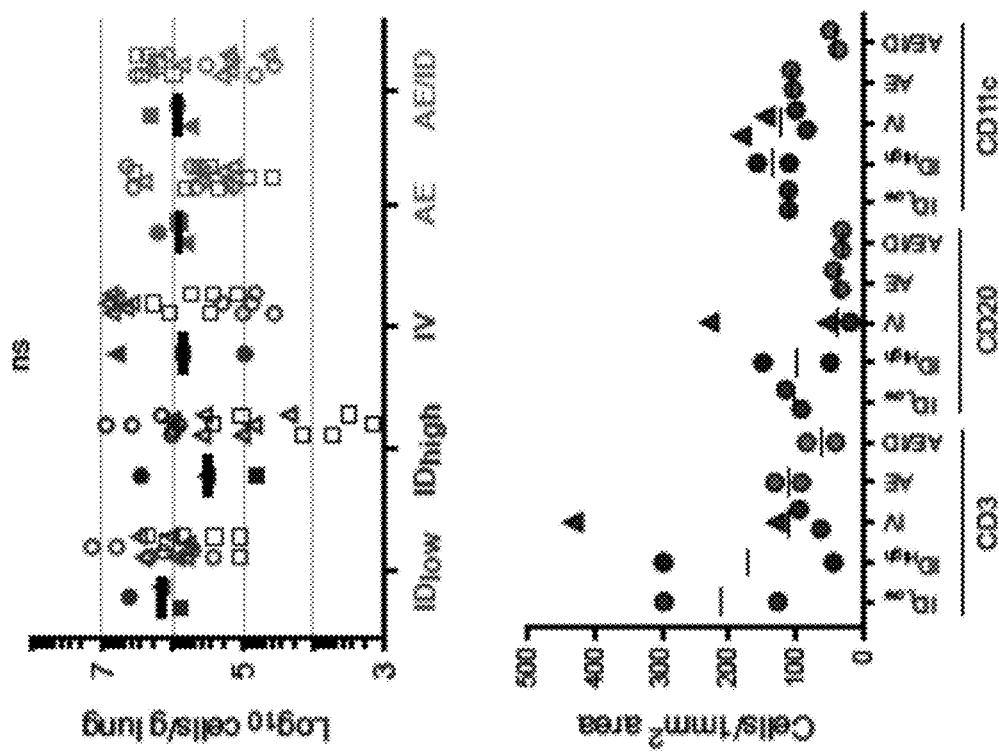
FIG. 22C
FIG. 22E

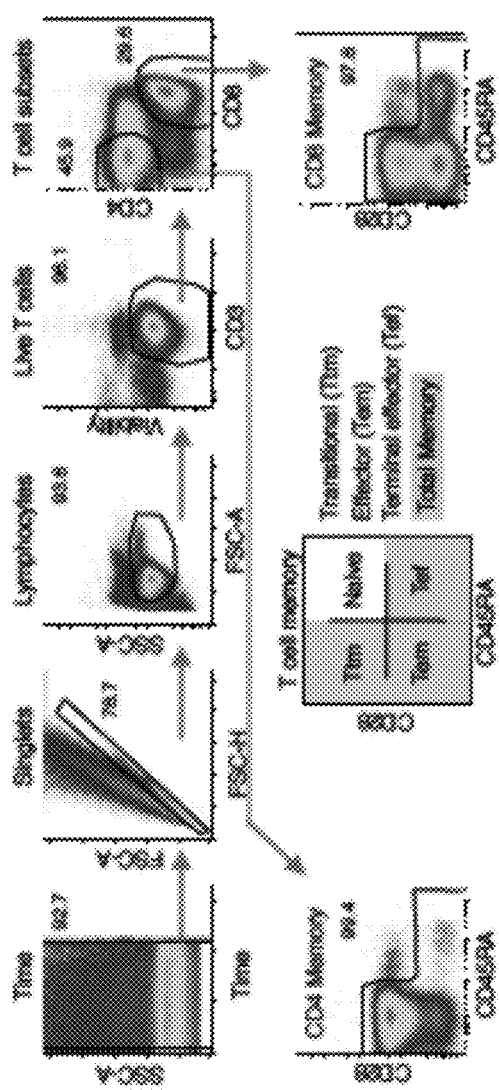
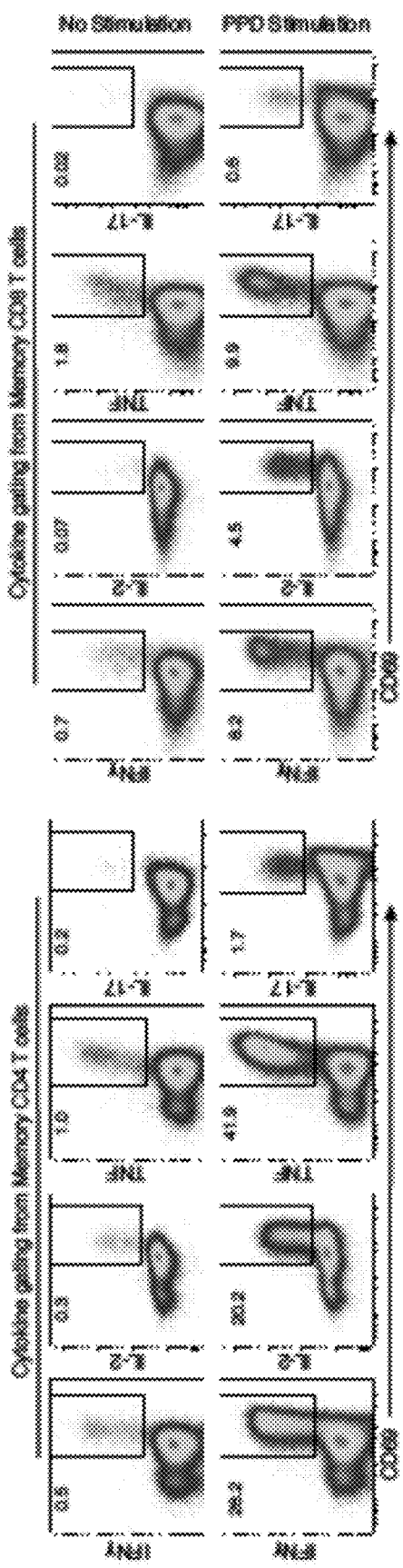
FIG. 27A
FIG. 27B
FIG. 27C

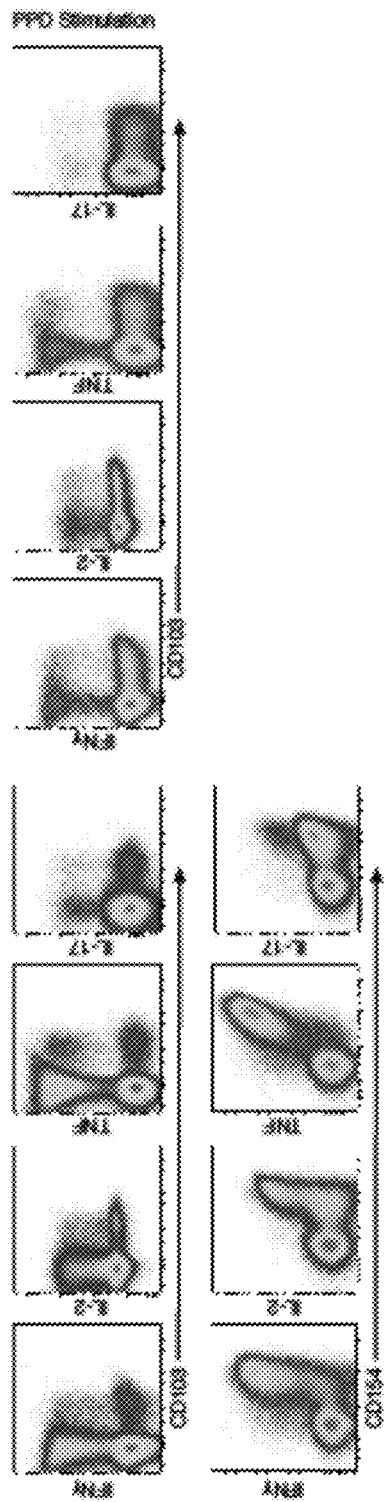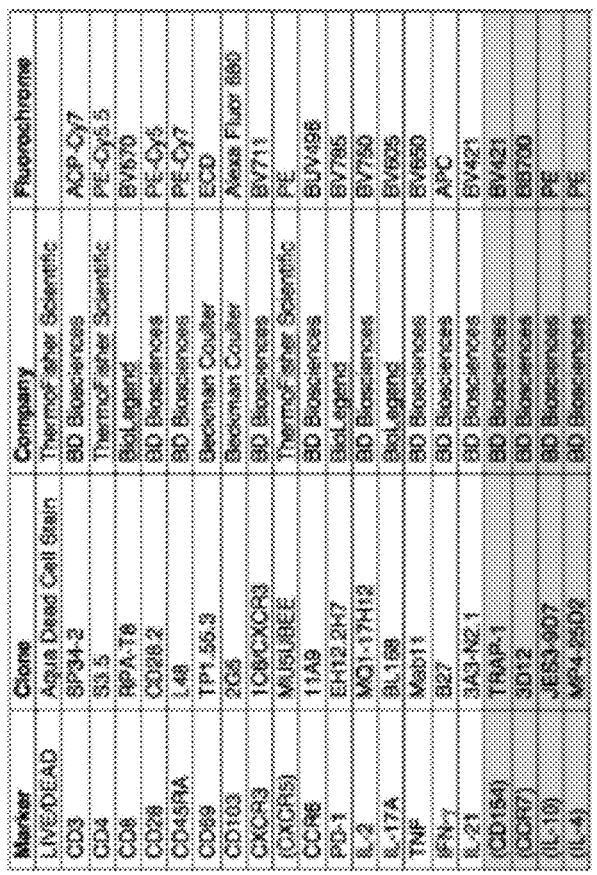
FIG. 27D
FIG. 27E
FIG. 27F

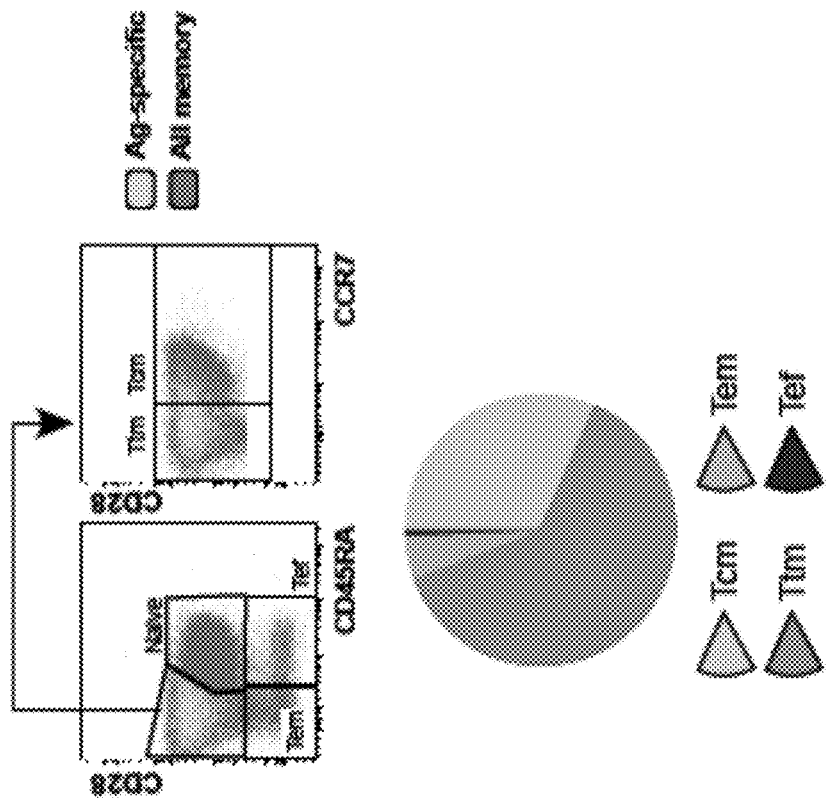

| PBMC Challenge Panel | | | |
|---|---|---|---|
| Marker | Color | Clone | Company |
| CCR4 | BV510 | L291H4 | Biolegend |
| CCR6 | BUV737 | 11A9 | BD Biosciences |
| CCR7 | AF680 | 150503 | VRC |
| CD127 | BV785 | A019D5 | Biolegend |
| CD137 | BUV395 | 4B4-1 | BD Biosciences |
| CD154 | BV421 | TRAP1 | BD Biosciences |
| CD25 | BUV563 | 2A3 | BD Biosciences |
| CD28 | PECy5 | CD28.2 | BD Biosciences |
| CD3 | APCCy7 | SP34-2 | BD Biosciences |
| CD4 | BUV496 | SK3 | BD Biosciences |
| CD45RA | PECy7 | 5H9 | BD Biosciences |
| CD69 | ECD | TP1.55.3 | Beckman Coulter |
| CD8 | BUV805 | SK1 | BD Biosciences |
| CXCR3 | BV711 | G025H7 | Biolegend |
| CXCR5 | SBR00 | MU5UBEE | InSitrogen |
| HLA-DR | PECy5.5 | Tu36 | TTermo |
| IFNg | APC | B27 | BD Biosciences |
| IL-17A | BV570 | BL168 | Biolegend |
| IL-2 | BV750 | MV1-17H12 | BD Biosciences |
| PD-1 | BB660 | EH12.1 | BD Biosciences |
| TCRgd | PE | 5A6.E9 | InSitrogen |
| TCR Vg9 | FITC | 7A5 | InSitrogen |
| TUFa | BV650 | MaW11 | BD Biosciences |
| Viability | UV-Blue | - | InSitrogen |

COMPOSITIONS AND METHODS FOR TREATING BACTERIAL INFECTIONS

CROSS-REFERENCE TO RELATED APPLICATIONS

This application claims the benefit of U.S. Provisional Application No. 62/954,998, filed Dec. 30, 2019. The entire contents of the above-identified application are hereby fully incorporated herein by reference.

STATEMENT REGARDING FEDERALLY SPONSORED RESEARCH

This invention was made with government support under Grant No.(s) AI118672 and HG006193 awarded by the National Institutes of Health. The government has certain rights in the invention.

TECHNICAL FIELD

The subject matter disclosed herein is generally directed to formulations and methods for treating and preventing infections by *Mycobacterium tuberculosis* (MTB).

BACKGROUND

There are 2 billion people in the world infected with *Mycobacterium tuberculosis* (Mtb), with 10 million new cases of active tuberculosis (TB) and 1.7 million deaths each year. TB is the leading cause of mortality in HIV-infected individuals. Mathematical modeling suggests that prevention of pulmonary infection or disease in adolescents and adults would have the largest impact on the epidemic, by controlling Mtb transmission (Harris et al. *Human Vaccines Immunother* 12:2813-2832 (2016)). Thus, development of a highly effective vaccine against pulmonary Mtb infection is an urgent global health priority. The only licensed TB vaccine, Bacille Calmette-Guerin (BCG; live, attenuated *Mycobacterium bovis*), is commonly administered by the intradermal (ID) route at birth and provides excellent protection against disseminated TB and some protection against pulmonary TB in young children, but has variable efficacy against pulmonary disease at other ages.

Mtb infection is initiated in lung macrophages following aerosol exposure. Once macrophages are infected, T cell immunity is required to control Mtb infection and prevent clinical disease (Cooper *Annu Rev Immunol* 27:393-422 (2009)). Accordingly, most current vaccine candidates in clinical development focus on eliciting T cell immunity to prevent pulmonary TB (Ottenhoff and Kaufmann *PLoS Pathogens* 8:e1002607 (2012)). A major hurdle is the ability to induce and sustain T cell responses with sufficient antigenic breadth—Mtb encodes ~4,000 proteins—in the lung to exert immediate control of infection. Induction of circulating, long-lived T cell memory may also be critical to provide a reservoir for renewal of tissue resident cells in the lung (Beverley et al. *Muc Immunol* 7:20-26 (2014); Sakai et al. *J Immunol* 192:2965-2969 (2014)). Thus, formulations that elicit broad antigenic breadth combined with delivery approaches that induce systemic and tissue resident T cells may be critical for developing efficacious TB vaccines.

ID and intramuscular (IM) administration are the most common routes of vaccine delivery. However, such routes do not induce high frequencies of lung resident T cells that may be critical for protection against TB (Beverley et al. *Muc Immunol* 7:20-26 (2014)). Of note, studies performed nearly 50 years ago in nonhuman primates (NHP) suggested that administration of BCG by the aerosol (AE) or intravenous (IV) route enhanced protection in some animals when challenged shortly after immunization (Barclay et al. *Infect Immun* 2:574-582 (1970); Barclay et al. *Am Rev Resp Dis* 107:351-358 (1973)). However, there remains a limited understanding for the mechanisms by which the dose and route of BCG influence systemic and tissue immunity, and whether optimizing these variables can lead to high level prevention of Mtb infection and disease. A sufficiently high dose of IV BCG might elicit a high frequency of systemic and tissue resident T cells that would mediate durable protection against Mtb infection and disease in the highly susceptible rhesus macaque model.

Citation or identification of any document in this application is not an admission that such a document is available as prior art to the present invention.

SUMMARY

In one aspect the invention provides a pharmaceutical formulation for therapeutic or prophylactic treatment of an intracellular bacterial infection in a subject in need thereof, comprising one or more modulating agents, wherein the one or more modulating agents increase expression of IFNγ, IL-2, TNF, and/or IL-17 in systemic and/or lung T cells.

In some embodiments, the increase of expression of IFNγ, IL-2, TNF, and/or IL-17 occurs in lung T cells. In some embodiments, the lung T cells are lung resident T cells. In some embodiments, the lung cells are T cells that are recruited to the lung.

In some embodiments, the T cells are CD4+ and/or CD8+ T cells.

In some embodiments, the one or more modulating agents further increases the fractional or overall abundance of CD3+ T cells, CD11c+ macrophages, dendritic cells, or a combination thereof.

In some embodiments, the lung resident T cells are CD4+ T cells that also express CD69. In some embodiments, the lung resident T cells also express CD40L. In some embodiments, the CD4+ T cells further express CD103.

In some embodiments, the lung resident T cells are CD8+ T cells.

In some embodiments, the one or more modulating agents further increase the expression of one or more of IFNγ, TBX21, RORC, TNFSF8, IL-21R, ABCA1, ADAM19, AGO2, ANKRD11, ARAP2, ARID5B, ATP2A3, ATP2B4, BATF, BCL2L11, BCOR, BHLHE40, BIRC3, BTG1, C3, CBLB, CCDC6, CCDC88C, CCL5, CCND2, CCR5, CCR7, CD2, CD247, CD28, CD3D, CD6, CD84, CHD3, CORO1A, CPD, CYFIP2, DNAJC1, DOCK10, DUSP16, EIF4G3, ELK4, ERC1, ETS1, FAM107B, FOSL2, FOX03, FRMD4B, FURIN, FYB, GIMAP7, GPRIN3, GZMB, HERC1, HIPK2, HIVEP1, HOPX, HTATSF1, HUWE1, ICOS, IFITM1, IKZF1, IL1R1, IRF4, ITGA4, KAT6A, KMT2A, KMT2E, LAT, LAT2, LCK, LOC698693, LOC703029, LOC710951, LPIN1, LTA, LTB, LYST, MAF, MAP3K14, MAP4K4, MPHOSPH8, MPRIP, NCOA1, NCOA2, NCOA3, NEDD4L, NOTCH2, PCNX, PHIP, PIK3CD, PITPNM1, PITRM1, POLR1B, PPP1R16B, PRDM1, PRKCH, PRKCQ, PRRC2B, RASGRP1, RASSF5, RBL2, RCSD1, REST, REV3L, RGS1, RNF19A, RORA, SAMS1, SATB1, SEMA4D, SETD7, SH3KBP1, SLA, SLAMF1, SMARCA2, SOS1, SPOCK2, SPTAN1, SSH1, STK17B, STK4, SUZ12, TLE3, TNFAIP3, TNFRSF1B, TNFRSF8, TPR, TRAF1, UBE20, USE1, WHSC1L1, WNK1, YLPM1, ZBED2, ZBTB38, ZNF281, AKAP1, APOBEC3A, ARID1A, CMAH, CSK, DGKA, DPP4, ECE1, EPHB2, FAM53B, FGFR10P2, FOXO1, GIMAP8, HEG1, IFI27, LAIR1, LAMP3, LSP1, MAMU-A, MMP25, NDRG1, PDGFA, PLA2G2D, RTEL1, SSRP1, SYT11, TGFBI, TMEM176B, TRERF1, UBD, UBTF, ARHGEF6, CLSTN1, DUSP4, FBXW2, LAD1, LY75, MIIP, PAPSS2, SCML4, SIGLEC1, VDR, ZC3H4, GPR171, HECA, HIVEP3, ID2, OGFRL1, PARP1, PSIP1, RASA3, RFTN1, SERPINB9, SLAMF7, SLC39A14, TNFRSF9, ANTXR2, BMP2K, BRD9, CLDND1, EHD1, ETV3, GABPB1, IL2RA, MCOLN2, NAV1, NFKBIA, NSMCE1, PARP8, SPECC1, TMEM176A, TNFRSF25, or TNIP1 in a cell, or the fractional or total abundance of cells that express them. In some embodiments, the one or more modulating agents increases the fractional or absolute number of Vγ9+γδ T cells and mucosal-associated invariant T (MAIT) cells. In some embodiments, the Vγ9+γδ T cells and MAIT cells are lung resident cells.

In some embodiments, the TNF is TNFβ or TNFα.

In some embodiments, the one or more modulating agents increases the ratio of T cells to macrophages.

In some embodiments, the one or more modulating agents are comprised in a Bacille Calmette-Guerin (BCG) vaccine. In some embodiments, the vaccine is administered intradermally, intramuscularly, intravenously, or by aerosol. In specific embodiments, the vaccine is administered intravenously.

In some embodiments, the one or more modulating agents modulates the microenvironment of a cell mass. In some embodiments, the cell mass is a granuloma. In some embodiments, the cell mass is a fibroma.

In some embodiments, the intracellular bacterial infection is a *Mycobacterium tuberculosis* (MTB) infection.

In another aspect, the invention provides a pharmaceutical formulation for therapeutic or prophylactic treatment of an infection in a subject in need thereof, comprising one or more modulating agents, wherein the one or more modulating agents increase expression of IFNγ, IL-2, TNF, and/or IL-17 in systemic and/or lung resident T cells; and wherein the infection is caused by intracellular and/or extracellular pathogens.

In some embodiments, the increase of expression of IFNγ, IL-2, TNF, and/or IL-17 occurs in lung cells. In some embodiments, the lung cells are lung resident T cells. In some embodiments, the lung cells are T cells that are recruited to the lung.

In some embodiments, the T cells are CD4+ and/or CD8+ T cells.

In some embodiments, the one or more modulating agents further increase the fractional or overall abundance of CD3+ T cells, CD11c+ macrophages, dendritic cells, or a combination thereof. In some embodiments, the lung resident T cells are CD4+ T cells that also express CD69. In some embodiments, the lung resident T cells also express CD40L. In some embodiments, the CD4+ T cells further express CD103.

In some embodiments, the lung resident T cells are CD8+ T cells.

In some embodiments, the one or more modulating agents further increase the expression of one or more of IFNγ, TBX21, RORC, TNFSF8, IL-21R, ABCA1, ADAM19, AGO2, ANKRD11, ARAP2, ARID5B, ATP2A3, ATP2B4, BATF, BCL2L11, BCOR, BHLHE40, BIRC3, BTG1, C3, CBLB, CCDC6, CCDC88C, CCL5, CCND2, CCR5, CCR7, CD2, CD247, CD28, CD3D, CD6, CD84, CHD3, CORO1A, CPD, CYFIP2, DNAJC1, DOCK10, DUSP16, EIF4G3, ELK4, ERC1, ETS1, FAM107B, FOSL2, FOX03, FRMD4B, FURIN, FYB, GIMAP7, GPRIN3, GZMB, HERC1, HIPK2, HIVEP1, HOPX, HTATSF1, HUWE1, ICOS, IFITM1, IKZF1, IL1R1, IRF4, ITGA4, KAT6A, KMT2A, KMT2E, LAT, LAT2, LCK, LOC698693, LOC703029, LOC710951, LPIN1, LTA, LTB, LYST, MAF, MAP3K14, MAP4K4, MPHOSPH8, MPRIP, NCOA1, NCOA2, NCOA3, NEDD4L, NOTCH2, PCNX, PHIP, PIK3CD, PITPNM1, PITRM1, POLR1B, PPP1R16B, PRDM1, PRKCH, PRKCQ, PRRC2B, RASGRP1, RASSF5, RBL2, RCSD1, REST, REV3L, RGS1, RNF19A, RORA, SAMS1, SATB1, SEMA4D, SETD7, SH3KBP1, SLA, SLAMF1, SMARCA2, SOS1, SPOCK2, SPTAN1, SSH1, STK17B, STK4, SUZ12, TLE3, TNFAIP3, TNFRSF1B, TNFRSF8, TPR, TRAF1, UBE20, USE1, WHSC1L1, WNK1, YLPM1, ZBED2, ZBTB38, ZNF281, AKAP1, APOBEC3A, ARID1A, CMAH, CSK, DGKA, DPP4, ECE1, EPHB2, FAM53B, FGFR10P2, FOXO1, GIMAP8, HEG1, IFI27, LAIR1, LAMP3, LSP1, MAMU-A, MMP25, NDRG1, PDGFA, PLA2G2D, RTEL1, SSRP1, SYT11, TGFBI, TMEM176B, TRERF1, UBD, UBTF, ARHGEF6, CLSTN1, DUSP4, FBXW2, LAD1, LY75, MIIP, PAPSS2, SCML4, SIGLEC1, VDR, ZC3H4, GPR171, HECA, HIVEP3, ID2, OGFRL1, PARP1, PSIP1, RASA3, RFTN1, SERPINB9, SLAMF7, SLC39A14, TNFRSF9, ANTXR2, BMP2K, BRD9, CLDND1, EHD1, ETV3, GABPB1, IL2RA, MCOLN2, NAV1, NFKBIA, NSMCE1, PARP8, SPECC1, TMEM176A, TNFRSF25, or TNIP1 in a cell, or the fractional or total abundance of cells that express them.

In some embodiments, the one or more modulating agents increases the fractional or absolute number of Vγ9+γδ T cells and MAIT cells. In some embodiments, the Vγ9+γδ T cells and MAIT cells are lung resident cells.

In some embodiments, the TNF is TNFβ or TNFα.

In some embodiments, the one or more modulating agents increases the ratio of T cells to macrophages.

In some embodiments, the one or more modulating agents are comprised in a Bacille Calmette-Guerin (BCG) vaccine. In some embodiments, the vaccine is administered intradermally, intramuscularly, intravenously, or by aerosol. In specific embodiments, the vaccine is administered intravenously.

In some embodiments, the one or more modulating agents modulates the microenvironment of a cell mass. In some embodiments, the cell mass is a granuloma.

In another aspect, the invention provides a pharmaceutical formulation comprising one or more modulating agents capable of modulating the microenvironment of a cell or cell mass by altering the relative expression and/or secretion of IFNγ, IL-2, TNF, and/or IL-17 in systemic and/or lung resident T cells and/or macrophages.

In some embodiments, the cell mass is a granuloma. In some embodiments, the cell mass is a fibroma.

In yet another aspect, the invention provides a pharmaceutical formulation for therapeutic or prophylactic treatment of an intracellular bacterial infection in a subject in need thereof, comprising one or more modulating agents, wherein the one or more modulating agents increase expression of IFNγ, IL-2, TNF, and/or IL-17 in systemic and/or lung resident macrophages.

In yet another aspect, the invention provides a method of preventing a *Mycobacterium tuberculosis* (MTB) infection in a subject comprising administering a therapeutically effective amount of any of the pharmaceutical formulations described herein to the subject.

In yet another aspect, the invention provides a method of treating a *Mycobacterium tuberculosis* (MTB) infection in a subject in need thereof, comprising administering a therapeutically effective amount of any of the pharmaceutical formulations described herein to the subject.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 3A) except at weeks 2, 20, and 24 (n=3; cohort 4 only). For pie charts, ◉ P<0.05, ◉ ◉ P<0.01, ◉ ◉ ◉ P<0.001, ◉ ◉ ◉ ◉ P<0.0001 indicate differences compared to pre-vaccination within the same vaccine group using a Permutation test.

FIGS. 3A-3B—Animals, vaccine groups, and study cohorts. (3A) Data presented in this report are from a total of 115 NHP, 52 of which were challenged with Mtb. Due to the ABSL-3 capacity constraints and logistical limits in the number of animals that can be sampled, PET CT-scanned, or necropsied at any given time point, studies were broken into multiple sequentially immunized and/or challenged cohorts. A maximum of 20 NHP were infected with Mtb in any challenge cohort; Mtb infections were split over two days, staggered by 2 weeks. The actual doses of BCG for each immunization, determined by subsequent culture, is noted for each vaccine group. The time interval between vaccination and challenge is noted in weeks and the challenge dose of Mtb is listed for each challenge cohort. Protection data were from 10 NHP per group (8 for $ID_{high}$ and 4 unvax) in Cohorts 1-3 ("Immunology & Challenge"). BAL and PBMC T cell responses in FIGS. 9A-9H and FIGS. 11 and 12 include data from these challenged animals. Per protocol, BAL samples were not collected from these animals 8 weeks prior to, or after, challenge. Three NHP per vaccine group (n=15 total) were immunized just as in cohorts 1-3 but were not challenged. Instead, these animals (cohort 4; "Immunology Only") were sampled (BAL, PBMC) for 6 months after BCG immunization and were then euthanized to perform extensive immune analysis on various tissues at what would have been the time of challenge (6 months). Immune data from these animals are shown in FIGS. 10C, 10D, 10G-10J and FIG. 22A-22E. BAL samples from cohort 4 were transcriptionally profiled at weeks 13 and 25 (FIGS. 9F-9H, 13, and 14). Cohort 5 (a-c) includes 4 animals per group (except AE and AE/ID groups, n=2 NHP each) that were immunized with BCG and were euthanized 1-3 months later to assess BCG CFU and T cell responses in various tissues. Data from these animals are shown in FIGS. 20A-20F and 16B. NHP in cohort 6 ("ivCD45", n=2 per group) received IV anti-CD45 injection prior to necropsy to distinguish blood- and tissue-derived cells as shown in FIGS. 23A-23C, 24, and 25. Pilot cohorts (a-c) include NHP enrolled in the dose-finding pilot study (n=3 per dose and route; "Immunology Pilot"; FIG. 2) (3B) Total Mtb CFU ($log_{10}$) following Mtb challenge of unvaccinated rhesus macaques in this study (solid black dots, n=4) is similar to the total CFU ($log_{10}$) of Mtb-challenged unvaccinated rhesus macaques in a previous study (Darrah et al. *npj Vaccines* 4, 21, doi: 10.1038/s41541-019-0113-9 (2019)) (grey dots, n=12), with infection doses ranging from 8 to 16 CFU.

FIGS. 4A-4D—Clinical parameters after BCG immunization of NHP. NHP in each BCG vaccine group (n=11-13 per group; cohorts 1-4) were monitored for changes in clinical parameters at various time points after BCG vaccination. (4A) Weight and temperature; (4B) Liver function tests (ALT, AST, albumin, and globulin); (4C)C-reactive protein (CRP); (4D) Complete blood counts (CBC: lymphocytes, monocytes, neutrophils, eosinophils, and basophils). All tests were performed longitudinally on whole blood at time of collection except CRP which was batch-analyzed from frozen plasma samples; a 6 hour time point was measured for CRP only. Prior to vaccination, average temperature was 101.2° F. and CRP values ranged from 0-28 μg/ml (n=62). Data points shown are individual animals with interquartile range (box) and median (line). For each parameter, pre-vaccination (P) measurements for all animals (n=54) were combined and compared against distributions from every vaccine group at every time point using Dunnett's test for multiple comparisons; * P<0.05.

FIGS. 8A-8B—Innate cytokine production from PBMC after BCG vaccination. Studies show that recent Mtb exposure or BCG immunization in humans leads to increased innate cytokine production following stimulation of PBMC with unrelated microbial stimuli. This "trained innate immunity" has been associated with growth inhibition of BCG by PBMC in vitro, and enhanced protection in mice after IV BCG vaccination (Joosten et al. *J Clin Invest* 128:1837-1851 (2018); Kaufmann et al. *Cell* 172:176-190 (2018)). (8A) To investigate if a trained immune effect could be detected, PBMC from NHP before BCG (pre-vax) and at 4 and 24 weeks after $ID_{low}$- or IV-BCG immunization were stimulated in vitro with medium alone, Mtb whole cell lysate (Mtb), heat-killed *Staphylococcus aureus* (HkSA), or LPS for 24 hours. TNF, IL-1b and IL-6 were measured as primary indicators of trained immunity; however, no increases in cytokines were observed for either vaccine group after vaccination. (8B) As a positive control for stimulation, Applicants measured IFNγ as a cytokine produced following antigenic stimulation of T cells. Consistent with the flow cytometry data in FIG. 9A, PBMC from IV BCG-immunized NHP secreted higher levels of IFNγ compared to $ID_{low}$-immunized NHP in response to Mtb at 4 and 24 weeks after BCG. * P<0.05, *** P<0.001 using a 2-way ANOVA and Dunnett's multiple comparisons test.

FIGS. 9A-9H—Antigen-responsive immune analysis in blood and BAL after BCG immunization. (9A, 9B) Frequency (%) of memory CD4 (9A) or CD8 (9B) T cells in PBMC producing any combination of IFNγ, IL-2, TNF, or IL-17 in response to PPD stimulation, identified as in Methods. Shown are individual and median (horizontal bar) responses from NHP in challenge cohorts at weeks 4 (peak) and 24 (time of challenge) post-BCG. (9C, 9D) Frequency (%, top) and absolute number ($\log_{10}$, bottom) of cytokine+ memory CD4 (9C) and CD8 (9D) T cells in BAL before (pre, P) and up to 16 weeks after BCG vaccination (per protocol, NHP were not lavaged within 8 weeks of, or after, challenge). Shown are individual animal (light shaded lines) and mean responses (bold lines) for each vaccine group in challenge study. *P<0.05, P<0.01, *P<0.001, **P<0.0001 comparing all vaccine groups to $ID_{low}$ for PBMC (weeks 4 and 24; one-way ANOVA followed by Dunnett's multiple comparison test) or BAL (weeks 8 and 16; using Kruskal-Wallis test followed by Dunn's multiple comparison test). (9E), Memory CD4 T cells in BAL producing every combination of IFNγ, IL-2, or TNF at 8 weeks post-BCG (peak) are shown as frequencies from individual animals with median and interquartile range (bars) and as averaged proportions of the summed response (pie charts). IL-17 production (with or without other cytokines) is displayed on a lower scale (bar graph), and as an arc (proportion). A permutation test was used to compare fractional distributions, as shown in the pie charts, of all vaccine groups to $ID_{low}$; no differences were noted (ns, not significant). (9F-9H) Single-cell transcriptional analysis (Seq-Well) of BAL cells after BCG (two time points, n=3/group; cohort 4). (9F) Z-scored heatmaps of the average cellular score for modules identified in week 13 PPD-stimulated T cells at weeks 13 and 25 post-BCG. Bolded P values denote differences in distributions across vaccination routes (one-way ANOVA); P values for modules 5 and 2 indicate modules uniquely elevated in the IV group. (9G) Ridge plots showing distributions of module 2 expression among unstimulated (back) and stimulated (front) T cells at weeks 13 (left) and 25 (right). Module positivity (dashed line) is defined as two SD above the mean score of unvaccinated controls; percent module 2-positive is shown for each vaccine group. (9H**) Volcano plot showing differentially expressed genes between T cells positive- and negative for module 2 at week 13 (P-values calculated using the likelihood ratio test with Bonferroni correction).

FIGS. 10A-10J—Extended immune data from challenge and immunology cohorts. (10A, 10B) Full kinetic of PBMC responses from animals in challenge cohorts (1-3) as in FIG. 9A, 9B. Shown is the frequency of memory CD4 (10A) or CD8 (10B) T cells producing any combination of IFNγ, IL-2, TNF or IL-17 in response to PPD stimulation at various time points pre-(P) or post-BCG immunization. Light shaded lines are individual animal responses and bold, shaded lines represent the median response for each vaccine group. *P<0.05, P<0.01, *P<0.001, **P<0.0001 indicate increased responses comparing all vaccine groups to $ID_{low}$ at weeks 4 and 24 (one-way ANOVA followed by Dunnett's multiple comparison test, as in FIGS. 9A, 9B). (10C, 10D) T cell responses from a replicate cohort of similarly BCG-immunized rhesus macaques (n=3 per group; cohort 4) from which BAL was collected for 24 weeks post-BCG immunization. Shown is the frequency (top) or absolute number (bottom) of CD4 (10C) or CD8 (10D**) memory T cells expressing any combination of IFNγ, IL-2, TNF or IL-17 in response to PPD stimulation, pre-(P) and post-BCG. Light shaded lines are individual animals and bold, shaded lines represent the mean response for each vaccine group. Kruskal-Wallis test was used followed by Dunn's multiple comparison test to compare cytokine responses at weeks 8 (peak) and 24 ("time of challenge") in all vaccine groups to $ID_{low}$. * P<0.05,  P<0.01, * P<0.001, **** P<0.0001. (10E, 10F) As the memory phenotype of antigen-responsive T cells can correspond with the migration potential and differentiation state of T cell responses, as well as provide insight into their functional capacity and durability (Soares et al. *J Infect Dis* 207:1084-1094 (2013)), Applicants assessed the memory phenotype of antigen-responsive CD4 (10E) and CD8 (10F) T cells in PBMC and BAL at peak (week 4 for PBMC; week 8-12 for BAL) and time of challenge (week 24 collected for PBMC only). Cytokine-positive T cells were categorized as central memory (Tcm), transitional memory (Ttm), effector memory (Tem), or terminal effectors (Tef) based on expression of CD45RA, CD28, and CCR7 as shown in FIGS. 28A-28D (PBMC). The majority of responding cells in PBMC were Tcm and Ttm, with the proportion of Ttm being larger in $ID_{high}$ and IV-immunized NHP compared to $ID_{low}$. In BAL, where T cells are CCR7-negative, most responding CD4 T cells were CD45RA-CD28+ Ttm (FIGS. 27A-27F). For CD8 memory phenotypes, pie graphs are shown only for groups that displayed measurable frequencies of cytokine+ CD8 T cells. IV-immunized animals had larger proportions of Tem in PBMC and BAL suggesting a more diverse composition of memory and effector cells than other routes. Comparisons of all vaccine groups to $ID_{low}$ (CD4 pie graphs only) were performed using a Permutation test; * P<0.05,  P<0.01, * P<0.001, **** P<0.0001. (10G, 10H) T cell responses in PBMC from a replicate cohort of similarly BCG-immunized rhesus macaques (n=3 per group; cohort 4). Shown is the frequency of CD4 (10G) and CD8 (10H) memory T cells producing any combination of IFNγ, IL-2, TNF or IL-17 in response to PPD stimulation pre (P) and post BCG. (10I, 10J) Percent of cytokine-positive (closed symbols, solid lines) or cytokine-negative (open symbols, dashed lines) memory CD4 (10G) or CD8 (10H) T cells expressing Ki-67 as identified in FIGS. 29A-29C. Lines represent 3 NHP per group (cohort 4).

FIGS. 18A-18G—Sterilizing protection in NHP after IV BCG immunization. (18A) Gross pathology score; (18B) Extrapulmonary score; (18C) Total thoracic bacterial burden (CFU); (18D) Bacterial burden in the lungs; and (18E) Bacterial burden in thoracic LN at necropsy. Each data point represents an individual NHP and horizontal bar represents the median. Data points within the grey areas are zero. Dashed line in (18A) is assumed normal pathology score; nonzero values below this result from variability in LN size in healthy rhesus macaques. Kruskal-Wallis tests were used and reported P values represent Dunn's multiple comparison test comparing each group to $ID_{low}$. (18F) Fisher's exact test P values are plotted for a range of CFU thresholds evaluating protection. For each threshold, a stacked bar plot indicates the percent of NHP with fewer CFU than the threshold (i.e., protected), in each vaccine group. Immunization route significantly ($P<10-4$) impacted protection at any given CFU threshold between <1 (sterile) and <104. (18G) PBMC response to ESAT-6 or CFP-10 peptides as determined by IFNγ ELISpot throughout Mtb infection. Each line is one animal over time. Sterile animals are represented by a triangle while non-sterile, protected animals (with 1≤CFU≤50) are squares. Kruskal-Wallis test was run at each time point with Dunn's adjusted P-values reported accounting for comparisons of all groups against $ID_{low}$. IV was lower than $ID_{low}$ at every time point after infection for ESAT-6 (4wk, P=0.001; 6wk, P=0.045; 8wk, P=0.025; 12wk, P=0.006) and CFP-10 (4wk, P<0.0001; 6wk, P=0.035; 8wk, P=0.001; 12wk, P=0.004).

FIGS. 19A-19C—Post-challenge immune responses in PBMC. (19A, 19B) The frequency of memory CD4 (19A) and CD8 (19B) T cells in PBMC from BCG-immunized animals (n=8-10 per group) producing any combination of IFNγ, IL-2, TNF or IL-17 in response to stimulation with either PPD (antigen present in BCG and Mtb; top row) or pooled ESAT-6 and CFP-10 peptides (antigens present in Mtb only; bottom row) were measured at the time of challenge (0), and at 4, 8, and 12 weeks after Mtb challenge. Measurements from 4 unvaccinated, infected animals are included as controls (Unvax). Light Shaded lines represent individual animals' responses and bolded, lines are the mean responses for each vaccine group. (19C) Mtb WCL-specific IgG, IgA, and IgM antibody titers were measured in the plasma of unvaccinated (n=4) and vaccinated animals (n=8-10) at the time of challenge (0), and at 4 and 12 weeks after challenge. Shown are Wilcoxon signed-rank unadjusted P values comparing cytokine frequencies or antibody titers at week 12 post-Mtb (or necropsy) to the time of challenge (week 0) within each vaccine group. ● 1403 P<0.05, ● ● P<0.01, ● ● ● P<0.001, ● ● ● ● P<0.0001.

FIGS. 20A-20F—BCG CFU and immune responses in tissues 1 month after BCG vaccination. NHP (cohorts 5a-c: n=4 $ID_{low}$, $ID_{high}$, and IV; n=2 AE and AE/ID) were euthanized 1 month after vaccination to quantify BCG and immune responses in various tissues. (20A) BCG CFU at immunization site(s) (skin, ID only) and in various tissues, calculated as described in Methods (per ml blood or bone marrow; per whole spleen, LN or lung lobe, or per total BAL harvested). Liver CFU were detected only in IV BCG animals (3 of 4), but T cell responses were not measured. (20B, 20C) Frequency of memory CD4 (20B) and CD8 (20C) T cells producing any combination of IFNγ, IL-2, TNF, or IL-17 in response to PPD-stimulation. Matched symbols within each vaccine group represent data from the same animal. Kruskal-Wallis tests were run, and reported P values represent Dunn's multiple comparison test comparing each vaccine group to $ID_{low}$. *P<0.05, **P<0.01. (20D) Total viable cells ($\log_{10}$) recovered per gram of lung tissue for each vaccine group; data are shown as the median of four animals per group (solid symbols, lung lobes from each animal are averaged) or as counts for each lung lobe from all animals (open symbols with lobes from same animal matched; no comparisons tested). Kruskal-Wallis test was run on medians; Dunn's adjusted P values are reported comparing each vaccine group to $ID_{low}$. (20E) Representative 1 mm² lung sections from each vaccine group were stained with H&E (left) or with antibodies against CD3+ T cells, CD20+ B cells, and CD11c+ macrophages or dendritic cells. (20F) Quantification of CD3+, CD20+, CD11c+ 1144 cells from 2 lung sections (matched symbols) from 2 animals per vaccine group using Cell Profiler™.

FIGS. 21A-21E—Comparative size and histopathological assessment of thoracic LN and spleen after BCG immunization. Thoracic LN from IV BCG animals at 4 weeks post-vaccination are enlarged, with follicular lymphoid hyperplasia, and contain numerous non-necrotizing granulomas. (21A) Thoracic LN from 2 animals per group were measured at 4 weeks post-BCG vaccination. Kruskal-Wallis test was run; Dunn's adjusted P values are reported comparing each vaccine group to $ID_{low}$. (21B) H&E stained sections of thoracic LN from vaccinated NHP. General structure with respect to cortical and medullary architecture and appearance is normal in LN from $ID_{low}$, $ID_{high}$ and AE/ID vaccinated NHP. The thoracic LN from the IV-vaccinated animals demonstrated marked follicular lymphoid hyperplasia, with enlarged, prominent, variably sized follicles, often with active, expanded germinal centers. Magnification 4× (21C) Small, non-necrotizing epithelioid histiocytic aggregates (non-necrotizing granulomas, black arrows) were abundantly disseminated within thoracic LN from the IV BCG animals. In the AE/ID animals, a wide nodal distribution of such lesions was also seen, although granuloma numbers and density were substantially less. The $ID_{high}$ animals had only one observable granuloma in a single thoracic LN and in the $ID_{low}$ NHP, no such structures were evident. Magnification 10×. (21D) Spleen volume was calculated from CT scans at 2 weeks and 4 weeks after BCG vaccination for 8 animals (cohorts 5a, b). (21E) Spleen volume was calculated from CT scans of 44 NHP (cohorts 1-3) just prior to Mtb challenge (6 months after BCG vaccination) and was not significantly different among vaccine routes (Kruskal-Wallis test, P=0.1643). Dots represent individual animals.

FIGS. 22A-22E—Immune response in tissues 6 months after BCG immunization. (22A) separate cohort of animals (n=3 per group, cohort 4; FIG. 3A) were vaccinated with BCG in parallel to the challenge study with the purpose of assessing immune responses in various tissues 6 months after BCG (the time point at which animals are challenged). (22A, 22B) Frequency of memory CD4 (a) and CD8 (b) T cells producing any combination of IFNγ, IL-2, TNF, or IL-17 in response to Mtb whole cell lysate (WCL) stimulation in the PBMC, spleen, bone marrow, peripheral LN, lung LN, lung tissue, and BAL. Individual LN and lung lobe responses were averaged by animal. Data points are three individual animals with symbols matched across tissues within a vaccine group; horizontal bar indicated the mean response. (22A) Number of cells recovered per gram of lung tissue for each animal in cohort 4; data are shown as the median of 3 animals per group (solid symbols, counts from individual lung lobes from each animal are averaged) or as counts for individual lung lobes for each animal (open symbols; lobes from the same animal have matched symbol). Kruskal-Wallis test was used, and P values represent Dunn's multiple comparison test comparing each vaccine group to $ID_{low}$. (22D) Representative 1 mm² lung sections from each vaccine group six months after BCG immunization were stained with H&E (left) or with antibodies against CD3+ T cells, CD20+ B cells, and CD11c+ macrophages or dendritic cells 1442. (22E) Quantification of CD3+, CD20+, CD11c+ cells from two lung sections (matched symbols) from 1-2 animals per vaccine group using Cell Profiler™.

Figures 1A, 1B, 1C:
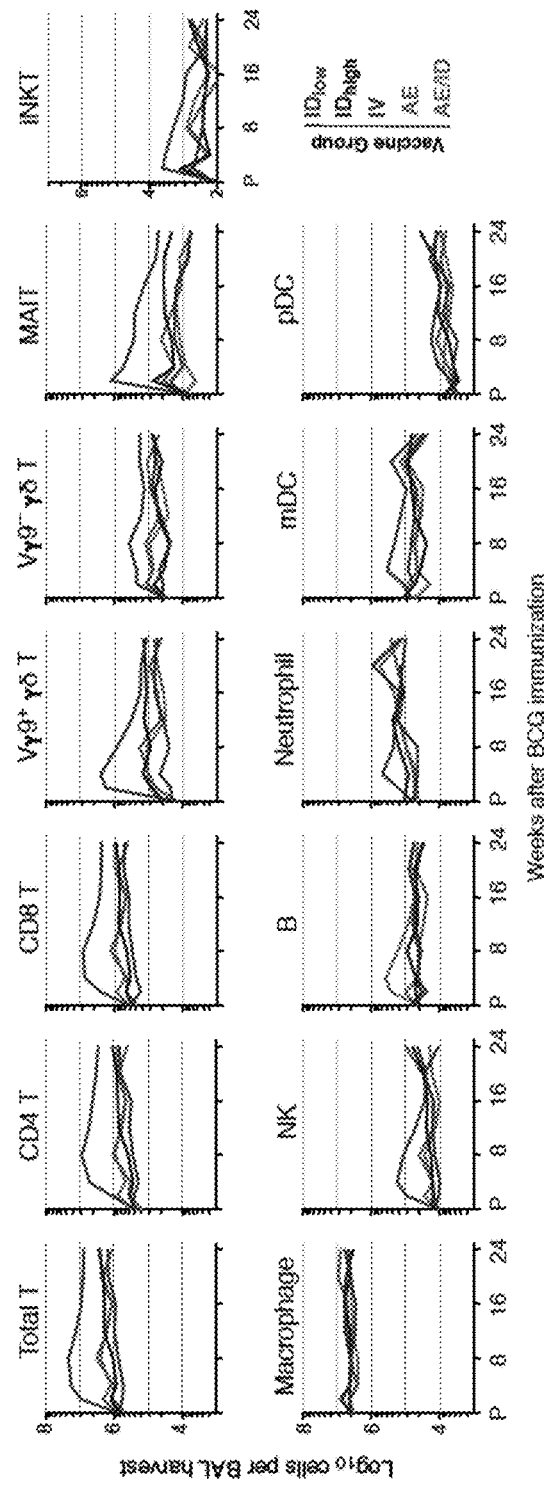
FIGS. 1A-1E—Study design and BAL cellular composition in rhesus macaques after BCG immunization. (1A and 1B) Vaccine groups and experimental design for Mtb challenge study in NHP. (1C) Geometric mean number of cells ($log_{10}$) per BAL harvest for indicated leukocyte populations in each vaccine group pre-vaccination (P) and up to 24 weeks after BCG; see FIGS. 5A and 5B for data from individual NHP and statistical comparisons. (1D, 1E) Pie charts comprising proportions of leukocytes (left) or T cell subsets (right) in BAL for each vaccine group from pre-vaccination (P) to 16 weeks after BCG, identified as in Methods. Data in FIGS. 1C-1E represent NHP cohorts 1-4 (n=11-13.

FIGS. 27A-27F—Gating strategy to measure antigen-responsive CD4 and CD8 T cells in BAL after BCG immunization. The flow cytometric gating strategy shown was applied to BAL (or tissue) samples following in vitro stimulation with antigen and intracellular cytokine staining, as in (FIGS. 9C-9E, 10C, 10D, and 12). (27A) A narrow singlet gate excludes many alveolar macrophages; live CD3+ T cells were gated using FSC-A by SSC-A, followed by exclusion of dead cells. CD4+ or CD8+ T cells were identified, followed by gating for memory T cells. Applicants use CD28 and CD45RA to identify total memory in BAL although few naive (CD28+CD45RA+) T cells are present. Memory populations in the BAL were classified as transitional memory (Ttm; CD28+CD45RA−), effector memory (Tem; CD28− CD45RA−), or terminal effectors (Tef; CD28−CD45RA+). As BAL T cells are largely negative for CCR7 staining (27B) compared to CCR7 staining of lymph node from the same animal), Applicants did not apply a gate to distinguish central memory T cells (Tcm; CD28+CD45RA−CCR7+) from Ttm (CD28+CD45RA−CCR7−). (27C) From total CD4 or CD8 memory, IFNγ, IL-2, TNF or IL-17 production was gated against the activation marker, CD69. Shown is a representative BAL sample from an IV BCG-immunized NHP, after no stimulation or PPD stimulation; it is common to see 'background' cytokine production from unstimulated NHP BAL. (27D) Typical expression of CD103 on BAL CD4 and CD8 T cells, shown against cytokines from a PPD-stimulated sample. (27E) CD154 was included in the intracellular staining mix of some, but not all, BAL samples; CD154 was largely co-expressed with IFNγ and TNF. (27F) Antibodies used in panel; markers in parenthesis were included at some, but not all time points. In a limited number of samples, antigen-induced IL-10 or IL-4 production was tested but not detected in the BAL. For ivCD45-injected animals, IFNγ clone B27 conjugated to BB700 (BD Bioscience) was used.

FIGS. 28A-28D—Gating strategy to measure antigen-responsive CD4 and CD8 T cells in PBMC after BCG immunization. The flow cytometric gating strategy was applied to batch analyzed PBMC following antigen-stimulation and intracellular cytokine staining to assess the frequency and quality of cytokine producing T cells and the memory phenotype of the response, as in FIGS. 9A, 9B, 10A, 10B, 10E, 10F, and 11. (28A) Total PBMC were gated for singlets, followed by a lymphocyte gate (SSC-A by FSC-A), a dump gate to remove HLA-DR high cells, and a viability gate to exclude dead cells. CD3+ T cells gated as Vγ9+γδ+ T cells or γδ− CD4+ and CD8+ T cells. For each T cell subset, naive (CD28+CD45RA+) cells were excluded and effector molecules were gated on total memory cells. (28B) Shown is a representative PBMC sample from an IV BCG-immunized animal with or without PPD stimulation. IFNγ, IL-2, TNF, IL-17 and CD154 were gated against the activation marker, CD69. (28C) The memory phenotype of the antigen-responsive T cell response was determined by gating on total CD4 or CD8 T cells and applying those gates to the Boolean-gated population of T cells producing any combination of cytokines measured. Pie charts display the proportion of the response that are central memory (Tcm; CD28+CD45RA−CCR7+), transitional memory (Ttm; CD28+CD45RA CCR7−), effector memory (Tem; CD28−CD45RA−), or terminal effectors (Tef; CD28−CD45RA+). (28D) Antibodies used in panel.

Figure 29A:
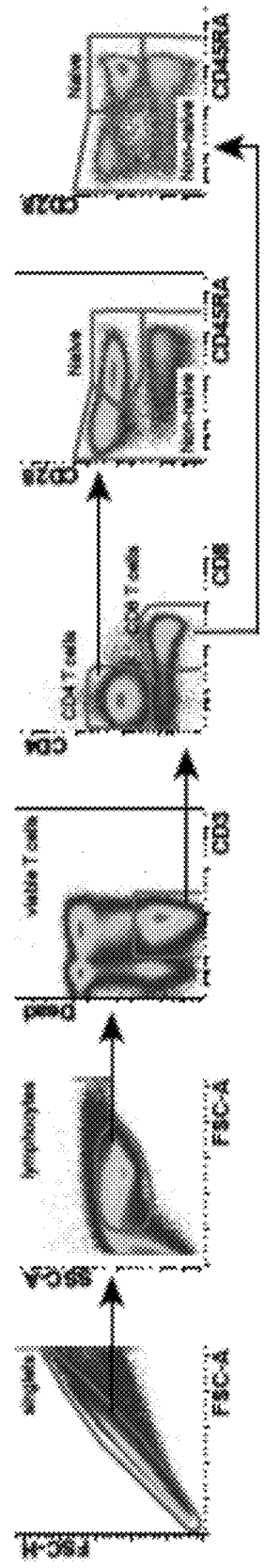
Figure 29B:
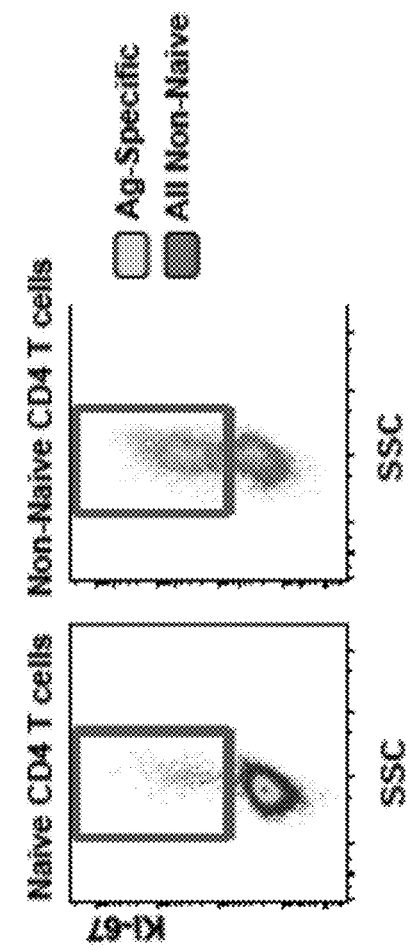
Figure 29C:
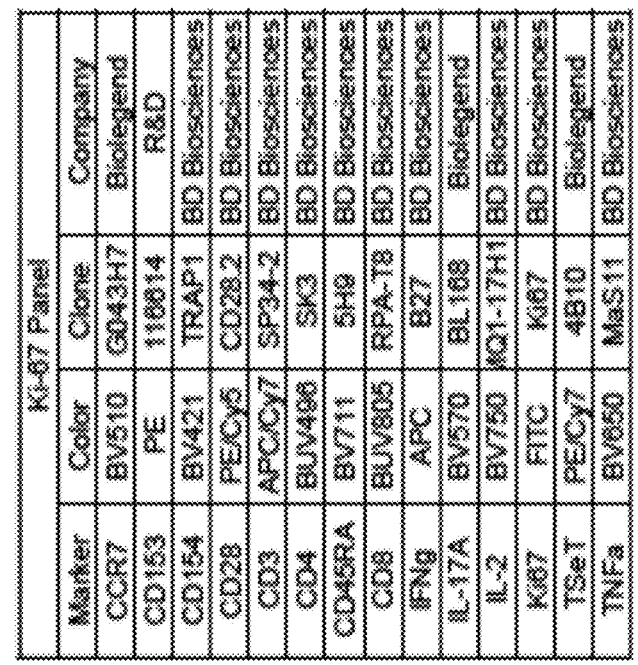

FIGS. 29A-29C—Gating strategy to identify Ki-67-positive antigen-responsive CD4 and CD8 T cells in PBMC after BCG immunization. The flow cytometric gating strategy was applied to PBMC to identify the proportion of antigen-responsive CD4 and CD8 T cells that express the marker of proliferation, Ki-67, as in FIGS. 10G-10J. As described in the methods, a multi-step staining protocol was used to optimize cytoplasmic cytokine and nuclear Ki-67 detection after in vitro antigen stimulation. Shown is a representative PBMC sample from an IV BCG-immunized NHP. (29A) Gating for cytokine-positive memory CD4 and CD8 T cells is shown in FIG. 28. (29B) Ki-67 was gated on total CD4 or CD8 memory cells (all non-naive) compared to naive T cells and then the Ki-67+ gate was applied to all antigen responsive T cells. (29C) Antibodies used in panel.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure $4^{th}$ ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit, and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide compositions and methods for treating subjects infected with *Mycobacterium tuberculosis* (MTB). The only available vaccine, BCG, is given intradermally (ID) and has variable efficacy against pulmonary tuberculosis (TB), the major cause of mortality and disease transmission. Applicants show that intravenous (IV) administration of BCG profoundly alters the outcome of MTB challenge. Compared to other routes, IV vaccination induces substantially more antigen-responsive CD4 and CD8 responses in blood, spleen, bronchoalveolar lavage, and lung lymph nodes. Moreover, IV immunization induces a high frequency of antigen-responsive T cells across all of the lung parenchymal tissue. The finding that IV BCG prevents or substantially limits MTB infection in highly-susceptible rhesus macaques has important implications for vaccine delivery and development and provides a model for determining immune correlates and mechanisms of vaccine-elicited protection against TB.

Applicants provide pharmaceutical formulations for therapeutic or prophylactic treatment of intracellular and extracellular bacterial infections. Formulations provided herein comprise one or more modulating agents that increase expression of IFNγ, IL-2, TNF, and/or IL-17 in systemic and/or lung resident T cells and macrophages. The one or more modulating agents may further increase the fractional or overall abundance of CD3+ T cells, CD11c+ macrophages, dendritic cells, or a combination thereof. Lung resident T cells may further express CD69, CD40L, and/or CD103. The one or more modulating agents may further increase expression of IFNγ, TBX21, RORC, TNFSF8, IL-21R, ABCA1, ADAM19, AGO2, ANKRD11, ARAP2, ARID5B, ATP2A3, ATP2B4, BATF, BCL2L11, BCOR, BHLHE40, BIRC3, BTG1, C3, CBLB, CCDC6, CCDC88C, CCL5, CCND2, CCR5, CCR7, CD2, CD247, CD28, CD3D, CD6, CD84, CHD3, CORO1A, CPD, CYFIP2, DNAJC1, DOCK10, DUSP16, EIF4G3, ELK4, ERC1, ETS1, FAM107B, FOSL2, FOX03, FRMD4B, FURIN, FYB, GIMAP7, GPRIN3, GZMB, HERC1, HIPK2, HIVEP1, HOPX, HTATSF1, HUWE1, ICOS, IFITML IKZF1, IL1R1, IRF4, ITGA4, KAT6A, KMT2A, KMT2E, LAT, LAT2, LCK, LOC698693, LOC703029, LOC710951, LPIN1, LTA, LTB, LYST, MAF, MAP3K14, MAP4K4, MPHOSPH8, MPRIP, NCOA1, NCOA2, NCOA3, NEDD4L, NOTCH2, PCNX, PHIP, PIK3CD, PITPNM1, PITRM1, POLR1B, PPP1R16B, PRDM1, PRKCH, PRKCQ, PRRC2B, RASGRP1, RASSF5, RBL2, RCSD1, REST, REV3L, RGS1, RNF19A, RORA, SAMS1, SATB1, SEMA4D, SETD7, SH3KBP1, SLA, SLAMF1, SMARCA2, SOS1, SPOCK2, SPTAN1, SSH1, STK17B, STK4, SUZ12, TLE3, TNFAIP3, TNFRSF1B, TNFRSF8, TPR, TRAF1, UBE20, USE1, WHSC1L1, WNK1, YLPM1, ZBED2, ZBTB38, ZNF281, AKAP1, APOBEC3A, ARID1A, CMAH, CSK, DGKA, DPP4, ECE1, EPHB2, FAM53B, FGFR10P2, FOXO1, GIMAP8, HEG1, IFI27, LAIR1, LAMP3, LSP1, MAMU-A, MMP25, NDRG1, PDGFA, PLA2G2D, RTEL1, SSRP1, SYT11, TGFBI, TMEM176B, TRERF1, UBD, UBTF, ARHGEF6, CLSTN1, DUSP4, FBXW2, LAD1, LY75, MIIP, PAPSS2, SCML4, SIGLEC1, VDR, ZC3H4, GPR171, HECA, HIVEP3, ID2, OGFRL1, PARP1, PSIP1, RASA3, RFTN1, SERPINB9, SLAMF7, SLC39A14, TNFRSF9, ANTXR2, BMP2K, BRD9, CLDND1, EHD1, ETV3, GABPB1, IL2RA, MCOLN2, NAV1, NFKBIA, NSMCE1, PARP8, SPECC1, TMEM176A, TNFRSF25, or TNIP1 in a cell, or the fractional or total abundance of cells that express them. Applicants also provide methods of treating or preventing infection by MTB by administering a therapeutically effective amount of the pharmaceutical formulations described herein. Administration may be carried out by the intravenous, intradermal, intramuscular, or aerosol route; preferably by the intravenous route.

Administration route, and therefore, formulation, may be chosen based on the type of response desired. In one embodiment, the administration is via aerosol or intradermal administration, according to the response desired. For example, intradermal administration, as described in the examples herein, may generate a high IFN type I response in T cells, which may be desirable in particular instances.

Pharmaceutical Formulations

In certain example embodiments, the invention provides a pharmaceutical formulation for therapeutic or prophylactic treatment of an infection in a subject in need thereof, comprising one or more modulating agents, wherein the one or more modulating agents increase expression of IFNγ, IL-2, TNF, and/or IL-17 in systemic and/or lung resident T cells.

The term "in need of treatment" as used herein refers to a judgment made by a caregiver (e.g. physician, nurse, nurse practitioner, or individual in the case of humans; veterinarian in the case of animals, including non-human animals) that a subject requires or will benefit from treatment. This judgment is made based on a variety of factors that are in the realm of a caregiver's experience, but that include the knowledge that the subject is ill, or will be ill, as the result of a condition that is treatable by the compositions and therapeutic agents described herein.

The infection may be a bacterial or viral infection, or may be caused by other pathogens, as described further below. The pathogen may be an intracellular or extracellular pathogen, as described further below. In specific embodiments, the infection is an intracellular bacterial infection.

Formulations for Treatment of Infections

A "pharmaceutical composition" or "pharmaceutical formulation" refers to a composition that usually contains an excipient, such as a pharmaceutically acceptable carrier that is conventional in the art and that is suitable for administration to cells or to a subject. Pharmaceutically acceptable as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propyleneglycol or polyethylene glycol may be included. The composition may include one or more cell protective molecules, cell regenerative molecules, growth factors, anti-apoptotic factors or factors that regulate gene expression in the cells. Such substances may render the cells independent of their environment. Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, a suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Drug compounds include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, radiation sensitizers, chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro testosterone, cortisol).

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

Suitable analgesics include, but are not limited to, paracetamol/acetaminophen, nonsteroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupirtine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable anti-histamines include, but are not limited to, H1-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, ranitidine, and roxatidine), tritoqualine, catechin, cromoglicate, nedocromil, and p2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, abacavir/lamivudine/zidovudine, lamivudine/zidovudine, emtricitabine/tenofovir, emtricitabine/lopinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, abacavir, zidovudine, stavudine, emtricitabine, xalcitabine, telbivudine, simeprevir, boceprevir, telaprevir, lopinavir/ritonavir, fosamprenavir, darunavir, ritonavir, tipranavir, atazanavir, nelfinavir, amprenavir, indinavir, saquinavir, ribavirin, valacyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceftaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, ceftizoxime, and ceftazidime), glycopeptide antibiotics (e.g. vancomycin, dalbavancin, oritavancin, and telavancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erythromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfisoxazole), tetracyclines (e.g. doxycycline, demeclocycline, minocycline, doxycycline/salicylic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, Cytoxan, cyclophosphamide, decitabine, dexamethasone, docetaxel, hydroxyurea, dacarbazine, leuprolide, epirubicin, oxaliplatin, asparaginase, estramustine, cetuximab, vismodegib, asparaginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylate, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, arsenic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Suitable radiation sensitizers include, but are not limited to, 5-fluorouracil, platinum analogs (e.g. cisplatin, carboplatin, and oxaliplatin), gemcitabine, DNA topoisomerase I-targeting drugs (e.g. camptothecin derivatives (e.g. topotecan and irinotecan)), epidermal growth factor receptor blockade family agents (e.g. cetuximab, gefitinib), farnesyltransferase inhibitors (e.g., L-778-123), COX-2 inhibitors (e.g. rofecoxib, celecoxib, and etoricoxib), bFGF and VEGF targeting agents (e.g. bevacizumab and thalidomide), NBTXR3, Nimoral, trans sodium crocetinate, NVX-108, and combinations thereof. See also e.g., Kvols, L. K., J Nucl Med 2005; 46:187S-190S.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationicoranionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8(2000), Wang W. "Lyophilization and development of solid protein pharmaceuticals." Int. J. Pharm. 203(1-2):1-60(2000), Charman, WN "Lipids, lipophilic drugs, and oral drug delivery-some emerging concepts." J Pharm Sci. 89(8):967-78(2000), Powell et al. "Compendium of excipients for parenteral formulations" PDAJ Pharm Sci Technol. 52:238-311(1998) and the citations therein for additional information related to formulations, excipients and carriers well known to pharmaceutical chemists.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

In some embodiments, the pharmaceutical formulations described herein may be used for therapeutic or prophylactic treatment of an infection.

Types of Infections

Infectious diseases may be caused by a variety of microbes which include bacteria, fungi, protozoa, parasites, and viruses.

Pathogens may be extracellular or intracellular. In an embodiment, extracellular pathogens may be first identified by proliferation in an extracellular environment, for example, *Vibrio cholerae*, and do not have the capacity to survive intracellularly. Exemplary extracellular pathogens include *Staphylococcus aureus*, streptococci such as *Streptococcus pyogenes*, *Haemophilus influenzae*, *Mycoplasma* spp., *Pseudomonas aeruginosa*, *Escherichia coli* and *Vibrio cholerae*. Intracellular pathogens are also within the scope of the invention and include those that commonly cause granulomas such as *Mycobacterium tuberculosis*, *Listeria monocytogenes*, *Salmonella* spp., *Neisseria* spp., *Legionella pneumophila*, *Histoplasma capsulatum*, *Cryptococcus neoformans*, Bacterial diseases may include diseases caused by any one or more of (or any combination of) *Acinetobacter baumannii*, *Actinobacillus* sp., Actinomycetes, *Actinomyces* sp. (such as *Actinomyces israelii* and *Actinomyces naeslundii*), *Aeromonas* sp. (such as *Aeromonas hydrophila*, *Aeromonas veronii* biovar *sobria* (*Aeromonas sobria*), and *Aeromonas caviae*), *Anaplasma phagocytophilum*, *Anaplasma marginate Alcaligenes xylosoxidans*, *Acinetobacter baumannii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melitensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeium* and *Corynebacterium*), *Clostridium* sp. (such as *Clostridium perfringens*, *Clostridium difficile*, *Clostridium botulinum* and *Clostridium tetani*), Eikenella corrodens, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chaffeensis* and *Ehrlichia canis*), *Epidermophyton floccosum*, *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingae*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Mannheimia haemolytica*, *Microsporum canis*, *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium paratuberculosis*, *Mycobacterium intracellulare*, *Mycobacterium avium*, *Mycobacterium bovis*, and *Mycobacterium marinum*), *Mycoplasma* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, Pityrosporum orbiculare (*Malassezia furfur*), *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rick-* ettsia rickettsii, Rickettsia akari* and *Rickettsia prowazekii, Orientia tsutsugamushi* (formerly: *Rickettsia* tsutsugamushi) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella* cholerasuis and *Salmonella typhimurium*), *Serratia* sp. (such as *Serratia marcescens* and *Serratia liquefaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equisimilis*, Group D streptococci, *Streptococcus bovis*, Group F streptococci, and *Streptococcus anginosus* Group G streptococci), Spirillum minus, *Streptobacillus moniliformi, Treponema* sp. (such as *Treponema carateum, Treponema petenue, Treponema pallidum* and *Treponema endemicum, Trichophyton rubrum, T mentagrophytes, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metschnikovii, Vibrio damsela* and *Vibrio furnissii*), *Yersinia* sp. (such as *Yersinia enterocolitica, Yersinia pestis*, and *Yersinia pseudotuberculosis*) and *Xanthomonas maltophilia* among others.

Fungal diseases may include diseases caused by any one or more of (or any combination of) *Aspergillus, Blastomyces*, Candidiasis, Coccidioidomycosis, *Cryptococcus neoformans, Cryptococcus gattii*, sp. *Histoplasma* sp. (such as *Histoplasma capsulatum*), *Pneumocystis* sp. (such as *Pneumocystis jirovecii*), *Stachybotrys* (such as *Stachybotrys chartarum*), Mucormycosis, *Sporothrix*, fungal eye infections ringworm, *Exserohilum, Cladosporium*.

In certain example embodiments, the fungus is a yeast. Examples of yeast that can be detected in accordance with disclosed methods include without limitation one or more of (or any combination of), *Aspergillus* species (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), a *Geotrichum* species, a *Saccharomyces* species, a *Hansenula* species, a *Candida* species (such as *Candida albicans*), a *Kluyveromyces* species, a *Debaryomyces* species, a *Pichia* species, or combination thereof. In certain example embodiments, the fungus is a mold. Example molds include, but are not limited to, a *Penicillium* species, a *Cladosporium* species, a *Byssochlamys* species, or a combination thereof.

Protozoan diseases may include diseases caused by any one or more of (or any combination of) Euglenozoa, Heterolobosea, Diplomonadida, Amoebozoa, *Blastocystis*, and Apicomplexa. Example Euglenozoa include, but are not limited to, *Trypanosoma cruzi* (Chagas disease), *T. brucei gambiense, T. brucei rhodesiense, Leishmania braziliensis, L. infantum, L. mexicana, L. major, L. tropica*, and *L. donovani*. Example Heterolobosea include, but are not limited to, Naegleria *fowleri*. Example Diplomonads include, but are not limited to, *Giardia intestinalis* (*G. lamblia, G. duodenalis*). Example Amoebozoa include, but are not limited to, *Acanthamoeba castellanii, Balamuthia madrillaris, Entamoeba histolytica*. Example Blastocysts include, but are not limited to, *Blastocystis hominis*. Example Apicomplexa include, but are not limited to, *Babesia microti, Cryptosporidium parvum, Cyclospora cayetanensis, Plasmodium falciparum, P. vivax, P. ovale, P. malariae*, and *Toxoplasma gondii*.

Parasitic diseases may include, but are not necessarily limited to, diseases caused by any one or more of (or any combination of) *Onchocerca* species and a *Plasmodium* species. In specific embodiments, the disease cause by a parasitic infection is malaria.

Viral diseases may include diseases caused by any one or more of (or any combination of) Ebolavirus, measles virus, SARS-Coronavirus, SARS-Coronavirus-2, Chikungunya virus, hepatitis viruses, Marburg virus, yellow fever virus, MERS, Dengue virus, Lassa fever virus, influenza virus, rhabdovirus or HIV. A hepatitis virus may include hepatitis A, hepatitis B, or hepatitis C virus. An influenza virus may include, for example, influenza A or influenza B virus. An HIV may include HIV 1 or HIV 2. In certain example embodiments, the viral sequence may be from a human respiratory syncytial virus, Sudan ebola virus, Bundibugyo virus, Tai Forest ebola virus, Reston ebola virus, Achimota, *Aedes* flavivirus, Aguacate virus, Akabane virus, Alethinophid reptarenavirus, Allpahuayo mammarenavirus, Amapari mammarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islands virus, BK polyomavirus, Bagaza virus, Banna virus, Bat herpesvirus, Bat sapovirus, Bear Canon mammarenavirus, Beilong virus, Betacoronavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, Caliciviridae virus. California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, *Culex* flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flaviviridae virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E virus, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human parechovirus, Human picornavirus, Human smacovirus, Ikoma lyssavirus, Ilheus virus, Influenza A-C virus, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khuj and virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MSSI2.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Mojiang virus, Mokola virus, Monkeypox virus, Montana *myotis* leukoencephalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichinde mammarenavirus, Picornaviridae virus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Togaviridae virus, Torque teno *canis* virus, Torque teno douroucouli virus, Torque teno *felis* virus, Torque teno midi virus, Torque teno sus virus, Torque teno tamarin virus, Torque teno virus, Torque teno *zalophus* virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or *Zygosaccharomyces bailii* virus Z viral sequence. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS-Coronavirus, SARS-Coronavirus-2, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In certain example embodiments, the virus may be a retrovirus. Example retroviruses that may be detected using the embodiments disclosed herein include one or more of or any combination of viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus).

In some embodiments, the infectious disease comprises a chronic viral infection, such as HIV. In some embodiments, the infectious disease comprises a chronic bacterial infection such as tuberculosis (TB). In some embodiments, the infectious disease comprises a chronic parasitic infection such as malaria.

In specific embodiments, the pharmaceutical formulation may be used for treating or preventing an intracellular bacterial infection, such as a *Mycobacterium tuberculosis* (MTB) infection.

Modulating Agents

As further detailed herein, a modulating agent broadly encompasses any condition, substance or agent capable of modulating one or more phenotypic aspects of a cell or cell population as disclosed herein. Such conditions, substances or agents may be of physical, chemical, biochemical and/or biological nature. A candidate agent refers to any condition, substance or agent that is being examined for the ability to modulate one or more phenotypic aspects of a cell or cell population as disclosed herein in a method comprising applying the candidate agent to the cell or cell population (e.g., exposing the cell, cell population, or tissue to the candidate agent or contacting the cell, cell population, or tissue with the candidate agent) and observing whether the desired modulation takes place. In some instances, the cell population comprises immune cells, in some embodiments, the cell population comprises T cells or macrophages.

The term "modulate" includes up-regulation and down-regulation, e.g., enhancing or inhibiting a response.

As used herein, modulating, or to modulate, generally means either reducing or inhibiting the expression or activity of, or alternatively increasing the expression or activity of a target gene. In particular, modulating can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An increase or decrease refers to a statistically significant increase or decrease, respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. Modulating can also involve effecting a change (which can either be an increase or a decrease) in affinity, avidity, specificity and/or selectivity of a target or antigen, such as a receptor and ligand. Modulating can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved. Accordingly, a modulating agent in an amount sufficient to modify a mycobacteria infection in a cell or tissue would provide the agent in an amount to effect a change in the amount of infection compared to the amount of infection in the cell or tissue in the absence of modulating agent, or untreated. The amount of modulating agent will vary according to the pathway, gene, or gene product targeted, the host, the tissue or cell, and the amount or copy number of the mycobacteria infection.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

Agents may include any potential class of biologically active conditions, substances or agents, such as for instance antibodies, proteins, peptides, nucleic acids, oligonucleotides, small molecules, or combinations thereof.

The modulating agents may be protein binding agents. As used herein, an agent can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

The agents of the present invention may be modified, such that they acquire advantageous properties for therapeutic use (e.g., stability and specificity), but maintain their biological activity.

The properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents and allow for particular agents to be capable of crossing the blood-brain barrier.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimido-propionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide (e.g., neuromedin U receptor agonists or antagonists) via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or K(CO(CH2)2SH) residues at any position in a peptide. In certain embodiments, the neuromedin U receptor agonists described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid.

Substitutions of amino acids may be used to modify an agent of the present invention. The phrase "substitution of amino acids" as used herein encompasses substitution of amino acids that are the result of both conservative and non-conservative substitutions. Conservative substitutions are the replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met, and Gly. Non-conservative substitutions are the replacement, in a polypeptide, of an amino acid residue by another residue which is not biologically similar. For example, the replacement of an amino acid residue with another residue that has a substantially different charge, a substantially different hydrophobicity, or a substantially different spatial configuration.

Antibody is used interchangeably with the term immunoglobulin herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

An antigen-binding fragment refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term antibody encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or immunoglobulin class, as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, 1 gM antibodies exist in pentameric form, and IgA antibodies exist in monomeric, dimeric or multimeric form.

IgG subclass refers to the four subclasses of immunoglobulin class IgG-IgG1, IgG2, IgG3, and IgG4 that have been identified in humans and higher mammals by the heavy chains of the immunoglobulins, V1-γ4, respectively. The term single-chain immunoglobulin or single-chain antibody (used interchangeably herein) refers to a protein having a two-polypeptide chain structure consisting of a heavy and a light chain, said chains being stabilized, for example, by interchain peptide linkers, which has the ability to specifically bind antigen. The term domain refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The variable domains of an antibody heavy chain are referred to interchangeably as heavy chain constant regions, heavy chain constant domains, "VH" regions or "VH" domains).

A region can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

Conformation refers to the tertiary structure of a protein or polypeptide (e.g., an antibody, antibody chain, domain or region thereof). For example, light (or heavy) chain conformation can refer to the tertiary structure of a light (or heavy) chain variable region, and the antibody conformation or antibody fragment conformation refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from non-immunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1 \times 10^7 M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant cross reactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a blocking antibody or an antibody antagonist is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its downstream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The modulating agent may be receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein.

The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

By means of example but without limitation, agents can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA, etc. Such nucleic acid sequences include, for example, but are not limited to, nucleic acid sequence encoding proteins, for example that act as transcriptional repressors, antisense molecules, ribozymes, small inhibitory nucleic acid sequences, including, for example, but not limited to RNAi, shRNAi, siRNA, micro RNAi (mRNAi), antisense oligonucleotides, CRISPR guide RNA, for example that target a CRISPR enzyme to a specific DNA target sequence, etc. A protein and/or peptide or fragment thereof can be any protein of interest, for example, but is not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments, the agent is a small molecule having a chemical moiety. Agents can be known to have a desired activity and/or property, or can be selected from a library of diverse compounds. The modulating agents herein may be one or more genetic modification agents. The genetic modulating agents may manipulate nucleic acids (e.g., genomic DNA or mRNA).

In certain embodiments, the agents may be small molecules, antibodies, therapeutic antibodies, antibody fragments, antibody-like protein scaffolds, aptamers, proteins, genetic modifying agents or small molecules. The chemical entity or biological product is preferably, but not necessarily a low molecular weight compound, but may also be a larger compound, or any organic or inorganic molecule effective in the given situation, including modified and unmodified nucleic acids such as antisense nucleic acids, RNAi, such as siRNA or shRNA, CRISPR-Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA, etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, minibodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments the agent is a small molecule having a chemical moiety. Agents can be known to have a desired activity and/or property, or can be selected from a library of diverse compounds.

In some embodiments, the modulating agents may be exogenous genes or functional fragments thereof. When delivered to specific nuclei in multinucleated cells, the exogenous gene may express a product (e.g., protein or nucleic acid) that manipulates the function of the cells or treats a disease related to the function of the cells. For example, the exogenous gene may encode dystrophin or a functional fragment thereof.

In certain embodiments, an agent may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-a, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signaling molecules, such as tumour necrosis factor (TNF) and interferons (e.g., interferon-a, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as agents include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

In some embodiments, the one or more modulating agents are comprised in a Bacille Calmette-Guerin (BCG) vaccine. The vaccine may be administered intradermally, intramuscularly, intravenously, or by aerosol, as described further below. In specific embodiments, the vaccine is administered intravenously.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, oligodendrocytes).

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naïve T cells, activated T cells, memory T cells, resting Tcons, or Tcons that have differentiated toward, for example, the Th1 or Th2 lineages. In some embodiments, Teffs are a subset of non-Treg T cells. In some embodiments, Teffs are CD4+ Teffs or CD8+ Teffs, such as CD4+ helper T lymphocytes (e.g., Th0, Th1, Tfh, or Th17) and CD8+ cytotoxic T lymphocytes. As described further herein, cytotoxic T cells are CD8+ T lymphocytes. "Naïve Tcons" are CD4+ T cells that have differentiated in bone marrow, and successfully underwent positive and negative processes of central selection in the thymus, but have not yet been activated by exposure to an antigen. Naive Tcons are commonly characterized by surface expression of L-selectin (CD62L), absence of activation markers such as CD25, CD44 or CD69, and absence of memory markers such as CD45RO. Naive Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) Philos. Trans. R. Soc. Lond. Biol. Sci. 356:625-637). In tumors, exhausted cells can present hallmarks of anergy.

In specific embodiments, the one or more modulating agents described herein increases expression of IFNγ, IL-2, TNF, and/or IL-17 in systemic and/or lung T cells.

In some embodiments, the target genes may be those in the INF-γ signaling pathway and/or genes in the TGFβ signaling pathway. In certain examples, the target genes include INF-γ, INF-γ receptor 2, TGFβ1, TGFβ receptor 3, CCL5, and IL-23R. In certain examples, the target genes include IL-2RG, IFN-γ, IFI27, LAG3, TIGIT, CD8A, NKG7, CCL20, CCL3, and CCL5. In some embodiments, these genes may be modulated in Th1-Th17 cells.

In specific embodiments, the increase of expression of IFNγ, IL-2, TNF, and/or IL-17 occurs in lung T cells. The lung T cells may be lung resident T cells or T cells that were systemic and were recruited to the lung. In some embodiments, the lung cells are lung resident T cells. In other embodiments, the lung cells are T cells that are recruited to the lung.

In some embodiments, the T cells are CD4+ and/or CD8+ T cells. In some embodiments, the T cells are helper T cells, naive T cells, activated T cells, cytotoxic T cells, regulatory T cells, and/or memory T cells. In some embodiments, the T cells are gamma delta T cells, natural killer T cells, innate lymphoid cells. In some embodiments, the T helper cells may be Th1, Th2, Th17, or T follicular helper cells.

In some embodiments, the one or more modulating agents further increase the fractional or overall abundance of CD3+ T cells, CD11c+ macrophages, dendritic cells, or a combination thereof.

In specific embodiments, the lung resident T cells are CD4+ T cells that also express CD69. In further embodiments, the lung resident T cells also express CD40L. In further embodiments, the CD4+ T cells also express CD103.

In some embodiments, the lung resident T cells are CD8+ T cells. In some embodiments, the CD8+ T cells also express CD69. In further embodiments, the CD8+ T cells also express CD40L. In further embodiments, the CD8+ T cells also express CD103.

In some embodiments, the one or more modulating agents further increase the expression of one or more additional cell markers in a cell, such as including, but not necessarily limited to IFNγ, TBX21, RORC, TNFSF8, IL-21R, ABCA1, ADAM19, AGO2, ANKRD11, ARAP2, ARID5B, ATP2A3, ATP2B4, BATF, BCL2L11, BCOR, BHLHE40, BIRC3, BTG1, C3, CBLB, CCDC6, CCDC88C, CCL5, CCND2, CCR5, CCR7, CD2, CD247, CD28, CD3D, CD6, CD84, CHD3, CORO1A, CPD, CYFIP2, DNAJC1, DOCK10, DUSP16, EIF4G3, ELK4, ERC1, ETS1, FAM107B, FOSL2, FOXO3, FRMD4B, FURIN, FYB, GIMAP7, GPRIN3, GZMB, HERC1, HIPK2, HIVEP1, HOPX, HTATSF1, HUWE1, ICOS, IFITM1, IKZF1, IL1R1, IRF4, ITGA4, KAT6A, KMT2A, KMT2E, LAT, LAT2, LCK, LOC698693, LOC703029, LOC710951, LPIN1, LTA, LTB, LYST, MAF, MAP3K14, MAP4K4, MPHOSPH8, MPRIP, NCOA1, NCOA2, NCOA3, NEDD4L, NOTCH2, PCNX, PHIP, PIK3CD, PITPNM1, PITRM1, POLR1B, PPP1R16B, PRDM1, PRKCH, PRKCQ, PRRC2B, RASGRP1, RASSF5, RBL2, RCSD1, REST, REV3L, RGS1, RNF19A, RORA, SAMS1, SATB1, SEMA4D, SETD7, SH3KBP1, SLA, SLAMF1, SMARCA2, SOS1, SPOCK2, SPTAN1, SSH1, STK17B, STK4, SUZ12, TLE3, TNFAIP3, TNFRSF1B, TNFRSF8, TPR, TRAF1, UBE20, USE1, WHSC1L1, WNK1, YLPM1, ZBED2, ZBTB38, ZNF281, AKAP1, APOBEC3A, ARID1A, CMAH, CSK, DGKA, DPP4, ECE1, EPHB2, FAM53B, FGFR10P2, FOXO1, GIMAP8, HEG1, IFI27, LAIR1, LAMP3, LSP1, MAMU-A, MMP25, NDRG1, PDGFA, PLA2G2D, RTEL1, SSRP1, SYT11, TGFBI, TMEM176B, TRERF1, UBD, UBTF, ARHGEF6, CLSTN1, DUSP4, FBXW2, LAD1, LY75, MIIP, PAPSS2, SCML4, SIGLEC1, VDR, ZC3H4, GPR171, HECA, HIVEP3, ID2, OGFRL1, PARP1, PSIP1, RASA3, RFTN1, SERPINB9, SLAMF7, SLC39A14, TNFRSF9, ANTXR2, BMP2K, BRD9, CLDND1, EHD1, ETV3, GABPB1, IL2RA, MCOLN2, NAV1, NFKBIA, NSMCE1, PARP8, SPECC1, TMEM176A, TNFRSF25, or TNIP1 in a cell, or the fractional or total abundance of cells that express them. The fractional abundance of cells is a proportion of one particular cell type relative to all of the cells.

In some embodiments, the one or more additional cell markers may include, but are not necessarily limited to, CD3E, DENND3, FAM129A, GCN1, MAP3K5, RRP1B, SOS2, USP1, WHSC1, ARHGAP4, GZMH, IL27RA, NOTCH1, PRF1, SYNE3, ISY1, ATXN10, EMB, EVL, LBH, or SLCO4A1.

In some embodiments, the one or more modulating agents increases the fractional or absolute number of Vγ9+γδ T cells and MAIT cells.

γδ T cells are T cells that have a distinctive T-cell receptor (TCR) on their surface. Most T cells are αβ (alpha beta) T cells with TCR composed of two glycoprotein chains called α (alpha) and β (beta) TCR chains. In contrast, γδ T cells have a TCR that is made up of one γ (gamma) chain and one δ (delta) chain. This group of T cells is usually less common than αβ T cells, but are at their highest abundance in the gut mucosa, within a population of lymphocytes known as intraepithelial lymphocytes. γδ T cells straddle the innate and adaptive arms of the immune system and are involved in response to pathogens and tumors.

MAIT cells make up a subset of T cells in the immune system that display innate, effector-like qualities. In humans, MAIT cells are found in the blood, liver, lungs, and mucosa, defending against microbial activity and infection. They constitute a subset of αβ T lymphocytes characterized by a semi-invariant T cell receptor alpha (TCRα) chain. In humans, MAIT cells express high levels of CD161, IL-18 receptor, and chemokine receptors CCR5, CXCR6, and CCR6 on the cell surface. MAIT cells are thought to play a role in autoimmune diseases, such as multiple sclerosis, arthritis, and inflammatory bowel disease. In specific embodiments, the MAIT cells target cells infected by intracellular bacteria.

In some embodiments, the Vγ9+γδ T cells and MAIT cells are lung resident cells.

In some embodiments, the one or more modulating agents increases expression of TNF, which may include TNFβ or TNFα.

In some embodiments, the one or more modulating agents increases the ratio of T cells to macrophages, as further described in the examples.

In some embodiments, the one or more modulating agents modulates the microenvironment of a cell or cell mass. The cell mass may be a granuloma or a fibroma. In specific embodiments, the cell mass is a granuloma.

A granuloma is a structure formed during inflammation that is found in many diseases. It is a collection of immune cells known as macrophages. Granulomas form when the immune system attempts to wall off substances it perceives as foreign but is unable to eliminate. Such substances include infectious organisms including bacteria and fungi, as well as other materials such as foreign objects, keratin, and suture fragments.

All granulomas, regardless of cause, may contain additional cells and matrix. These include lymphocytes, neutrophils, eosinophils, multinucleated giant cells, fibroblasts and collagen (fibrosis). The additional cells are sometimes a clue to the cause of the granuloma.

In terms of the underlying cause, the difference between granulomas and other types of inflammation is that granulomas form in response to antigens that are resistant to "first-responder" inflammatory cells such as neutrophils and eosinophils. The antigen causing the formation of a granuloma is most often an infectious pathogen or a substance foreign to the body, but sometimes the offending antigen is unknown. Granulomas are seen in a wide variety of diseases, both infectious and non-infectious. Infections that are characterized by granulomas include tuberculosis, leprosy, schistosomiasis, histoplasmosis, cryptococcosis, coccidioidomycosis, blastomycosis, cat scratch disease, rheumatic fever, sarcoidosis, Crohn's disease, Aspiration pneumonia, Rheumatoid arthritis, Granuloma annulare, Foreign-body granuloma, childhood granulomatous periorificial dermatitis, and infections caused by *Listeria monocytogenes, Leishmania* spp., and *Pneumocystis* pneumonia.

Fibromas are benign tumors that are composed of fibrous or connective tissue. They can grow in all organs, arising from mesenchyme tissue. The term "fibroblastic" or "fibromatous" is used to describe tumors of the fibrous connective tissue. When the term fibroma is used without modifier, it is usually considered benign, with the term fibrosarcoma reserved for malignant tumors. Fibromas can be hard or soft. Hard fibromas consist of many fibers and few cells, for example in skin they are called dermatofibroma (fibroma simplex or modulus cutaneous). A special form of hard fibroma is the keloid, which derives from hyperplastic growth of scars. Soft fibromas (fibroma molle) or fibroma with a shaft (acrochordon, skin tag, fibroma pendulans) consists of many loosely connected cells and less fibroid tissue. It mostly appears at the neck, armpits or groin. Other types of fibroma include fibroma cavernosum or angiofibroma, which consists of many often dilated vessels—it is a vasoactive tumor occurring almost exclusively in adolescent males; cystic fibroma (fibroma cysticum), which has central softening or dilated lymphatic vessels; myxofibroma (fibroma myxomatosis), which is produced by liquefaction of the underlying soft tissue; cemento-ossifying fibroma, which is hard and fibrous, most frequently seen in the jaw or mouth, sometimes in connection with a fracture or another type of injury; chondromyxoid fibroma; desmoplastic fibroma; nonossifying fibroma; ossifying fibroma; nuchal fibroma; collagenous fibroma; fibroma of tendon sheath; perifollicular fibroma; pleomorphic fibroma; uterine fibroma; etc. Neurofibroma is a benign nerve-sheath tumor in the peripheral nervous system. Ovarian fibromas appear in the sex cord-stromal tumor group of ovarian neoplasms. Ovary fibromas are most frequent during middle age, and are rare in children.

Formulations for Modulating the Microenvironment of a Cell or Cell Mass

In some embodiments, the invention provides a pharmaceutical formulation comprising one or more modulating agents capable of modulating the microenvironment of a cell or cell mass by altering the relative expression and/or secretion of IFNγ, IL-2, TNF, and/or IL-17 in systemic and/or lung resident T cells and/or macrophages.

Microenvironment

A cell's microenvironment includes the extracellular matrix; similar or dissimilar cells that surround another cell; different cytokines, hormones, and reactive species; local physical properties of a cell; the mechanical forces that are produced by the movement of molecular motors or fluids inside a cell. The importance of each factor depends on the nature of the cell or tissue, and on the combination of these factors which ultimately will influence the behavior of the cells/tissue in the microenvironment.

The microenvironment of a cell mass is the cellular environment in which the cell mass exists, including surrounding blood vessels, immune cells, fibroblasts, bone marrow-derived inflammatory cells, lymphocytes, signaling molecules and the extracellular matrix. As used herein, immune cells may include any cells of the innate or adaptive immune system, such as, but not necessarily limited to, monocytes, macrophages, neutrophils, mast cells, eosinophils, basophils, dendritic cells, peripheral blood mononuclear cells, T cells, B cells, or natural killer cells, or a combination thereof.

In some embodiments, altering the expression and/or function of the target genes and proteins may modulate the microenvironment in a cell, cell mass, or tissue in a subject.

Microenvironment may refer to the sum total of cell-cell, cell-ECM, and cell-soluble factor interactions, in addition to geometric and physical properties of the surroundings, that are experienced by a cell. Cell-microenvironment interactions may make possible the levels of tissue specific behavior observed in every higher organism, where there may be billions of cells with identical genetic information that serve as constituents of the different tissues and organs. In order for each tissue or organ to operate successfully within the context of the organism, all cells must be integrated into an architectural and signaling framework such that each cell knows which commands to execute at any given time. Success at this daunting task leads to homeostasis, whereas failure results in a spectrum of dysfunctions, including cancer, other diseases, and aging. Microenvironment properties combine to exert control over the genome in both normal and diseased cells. Isolated cells are known to lose most functional differentiation when separated and placed in traditional cell cultures. However, the cellular identity is not lost permanently, as this can be achieved by controlling the microenvironment of the cells in culture, the cell can "remember" many of their original tissue specific traits. Metastable epigenetic states of cells also may be essential to help maintain the fidelity of phenotypes that are the result of dynamic and reciprocal interactions between cells and their microenvironments.

As will be clear to the skilled person, "modulating" or "modifying" can also involve effecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

The terms "high," "higher," "increased," "elevated," or "elevation" refer to increases above basal levels, e.g., as compared to a control. The terms "low," "lower," "reduced," "decreased" or "reduction" refer to decreases below basal levels, e.g., as compared to a control.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be a stored sample or previous sample measurement) with a known outcome; normal tissue, fluid, or cells isolated from a subject, such as a normal patient or the patient having a condition of interest. As such, relative expression refers to expression of a gene, gene signature, gene product or protein relative to a control or baseline expression level.

As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of a gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (be it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory, the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory, the presence of specific cells and cell subtypes are indicative of a particular response to treatment, such as including increased or decreased susceptibility to treatment. The signature may indicate the presence of one particular cell type. In one embodiment, the novel signatures that are used to detect multiple cell states or hierarchies that occur in subpopulations of cell masses are linked to a particular pathological condition (e.g. tumor), or linked to a particular outcome or progression of the disease (e.g. metastasis), or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different tumor cells or tumor cell (sub)populations, as well as comparing tumor cells or tumor cell (sub)populations with non-tumor cells or non-tumor cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute a (sub)population of cells of a particular cell type characterized by a specific cell state.

When referring to induction, or alternatively suppression of a particular signature, preferably what is meant is induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

In some embodiments, the cell mass is a granuloma, as described elsewhere herein. In some embodiments, the cell mass is a fibroma, as described elsewhere herein.

In some embodiments, the altered expression and/or secretion of IFNγ, IL-2, TNF, and/or IL-17 occurs in lung T cells, as described elsewhere herein. In some embodiments, the lung T cells are lung resident T cells. In some embodiments, the lung cells are T cells that are recruited to the lung.

In some embodiments, the T cells are CD4+ and/or CD8+ T cells. In some embodiments, the one or more modulating agents further increase the fractional or overall abundance of CD3+ T cells, CD11c+ macrophages, dendritic cells, or a combination thereof. In some embodiments, the lung resident T cells are CD4+ T cells that also express CD69. In some embodiments, the lung resident T cells also express CD40L. In some embodiments, the CD4+ T cells further express CD103. In some embodiments, the lung resident T cells are CD8+ T cells.

In some embodiments, the one or more modulating agents further increase the expression of one or more of IFNγ, TBX21, RORC, TNFSF8, IL-21R, ABCA1, ADAM19, AGO2, ANKRD11, ARAP2, ARID5B, ATP2A3, ATP2B4, BATF, BCL2L11, BCOR, BHLHE40, BIRC3, BTG1, C3, CBLB, CCDC6, CCDC88C, CCL5, CCND2, CCR5, CCR7, CD2, CD247, CD28, CD3D, CD6, CD84, CHD3, CORO1A, CPD, CYFIP2, DNAJC1, DOCK10, DUSP16, EIF4G3, ELK4, ERC1, ETS1, FAM107B, FOSL2, FOXO3, FRMD4B, FURIN, FYB, GIMAP7, GPRIN3, GZMB, HERC1, HIPK2, HIVEP1, HOPX, HTATSF1, HUWE1, ICOS, IFITM1, IKZF1, IL1R1, IRF4, ITGA4, KAT6A, KMT2A, KMT2E, LAT, LAT2, LCK, LOC698693, LOC703029, LOC710951, LPIN1, LTA, LTB, LYST, MAF, MAP3K14, MAP4K4, MPHOSPH8, MPRIP, NCOA1, NCOA2, NCOA3, NEDD4L, NOTCH2, PCNX, PHIP, PIK3CD, PITPNM1, PITRM1, POLR1B, PPP1R16B, PRDM1, PRKCH, PRKCQ, PRRC2B, RASGRP1, RASSF5, RBL2, RCSD1, REST, REV3L, RGS1, RNF19A, RORA, SAMS1, SATB1, SEMA4D, SETD7, SH3KBP1, SLA, SLAMF1, SMARCA2, SOS1, SPOCK2, SPTAN1, SSH1, STK17B, STK4, SUZ12, TLE3, TNFAIP3, TNFRSF1B, TNFRSF8, TPR, TRAF1, UBE2O, USE1, WHSC1L1, WNK1, YLPM1, ZBED2, ZBTB38, ZNF281, AKAP1, APOBEC3A, ARID1A, CMAH, CSK, DGKA, DPP4, ECE1, EPHB2, FAM53B, FGFR10P2, FOXO1, GIMAP8, HEG1, IFI27, LAIR1, LAMP3, LSP1, MAMU-A, MMP25, NDRG1, PDGFA, PLA2G2D, RTEL1, SSRP1, SYT11, TGFBI, TMEM176B, TRERF1, UBD, UBTF, ARHGEF6, CLSTN1, DUSP4, FBXW2, LAD1, LY75, MIIP, PAPSS2, SCML4, SIGLEC1, VDR, ZC3H4, GPR171, HECA, HIVEP3, ID2, OGFRL1, PARP1, PSIP1, RASA3, RFTN1, SERPINB9, SLAMF7, SLC39A14, TNFRSF9, ANTXR2, BMP2K, BRD9, CLDND1, EHD1, ETV3, GABPB1, IL2RA, MCOLN2, NAV1, NFKBIA, NSMCE1, PARP8, SPECC1, TMEM176A, TNFRSF25, or TNIP1 in a cell, or the fractional or total abundance of cells that express them.

In an embodiment, IFN-gamma is modulated by increased expression or activation of inducible costimulator (ICOS). See, e.g. Quiroga et al., J Immunol. 2006 May 15; 176(10): 5965-74; doi: 10.4049/jimmunol.176.10.5965. In an embodiment, IL-17 is enhanced, activated or increased. Exemplary pharmacologicals are known to increase IL-17 expression, including cyclosporin and methotrexate. Amatya et al., "IL-17 Signaling: The Yin and the Yang," Trends in Immunology, Volume 38, Issue 5, May 2017, Pages 310-322, doi: 10.1016/j.it.2017.01.006; see also, Kehlen et al., Clin Exp Immunol. 2002 March; 127(3):539-46; doi: 10.1046/j.1365-2249.2002.01782.x. Cytosolic adaptor molecule Act1 (also known as CIKS) can also be used for modulation of IL-17. See, e.g. Song et al., Cytokine, Volume 62, Issue 2, May 2013, Pages 175-182, doi: 10.1016/j.cyto.2013.03.014. Small molecule modulators of immune receptors can be found, for example, in ImmtorLig_DB, see, Chatterjee et al., Sci Rep 9, 3092 (2019). IL-2 may also be modulated with exemplary methods discussed in Spolski, R., Li, P. & Leonard, W. J. Biology and regulation of IL-2: from molecular mechanisms to human therapy. *Nat Rev Immunol* 18, 648-659 (2018), doi:10.1038/s41577-018-0046-y; Li, P. et al. STAT5-mediated chromatin interactions in superenhancers activate IL-2 highly inducible genes: functional dissection of the Il2ra gene locus. *Proc. Natl Acad. Sci. USA* 114, 12111-12119 (2017); Krieg, C., Letourneau, S., Pantaleo, G. & Boyman, O. Improved IL-2 immunotherapy by selective stimulation of IL-2 receptors on lymphocytes and endothelial cells. *Proc. Natl Acad. Sci. USA* 107, 11906-11911 (2010).

In embodiments, the one or more additional cell markers may include, but is not necessarily limited to, CD3E, DENND3, FAM129A, GCN1, MAP3K5, RRP1B, SOS2, USP1, WHSC1, ARHGAP4, GZMH, IL27RA, NOTCH1, PRF1, SYNE3, ISY1, ATXN10, EMB, EVL, LBH, or SLCO4A1.

In embodiments, the one or more modulating agents increases the fractional or absolute number of Vγ9+γδ T cells and MAIT cells, as described elsewhere herein. In some embodiments, the Vγ9+γδ T cells and MAIT cells are lung resident cells.

In embodiments, the TNF is TNFβ or TNFα.

In embodiments, the one or more modulating agents increases the ratio of T cells to macrophages, as described elsewhere herein.

In embodiments, the one or more modulating agents are comprised in a Bacille Calmette-Guerin (BCG) vaccine. In one embodiment, the modulating agents comprised in a BCG vaccine are administered intravenously.

In embodiments, the vaccine is administered intradermally, intramuscularly, intravenously, or by aerosol. In specific embodiments, the vaccine is administered intravenously.

In embodiments, the one or more modulating agents modulates the microenvironment of a cell mass. In some embodiments, the cell mass is a granuloma. In some embodiments, the cell mass is a fibroma.

Prophylactic and Therapeutic Methods of Treatment

In an embodiment, the invention provides methods of preventing or treating an infection in a subject comprising administering a therapeutically effective amount of any of the pharmaceutical formulations described herein to the subject.

In an embodiment, the methods and compositions disclosed herein are utilized to enhance, improve, and/or sustain an immune response, as described herein. In an embodiment, modulating agents as disclosed herein can be administered prior to, concurrently with, or subsequent to a vaccine. In an embodiment, the administration of the vaccine is intravenous administration. In an aspect, the vaccine is a live attenuated vaccine administered with a modulating agent enhancing or sustaining an immune response. In an embodiment, such methods may provide a sustained presence of antigen-responsive T cell responses. In one embodiment, the modulating agent is administered prior to, concurrently with, or subsequent to a BCG vaccine. In one embodiment, the BCG vaccine, and optionally the modulating agent, administration is intravenous.

Methods to enhance, improve and/or sustain immune response can be measured based on, for example, via reduction in CFU of Mtb from a benchmark control of administration without a modulating agent, via different route of administration (e.g. intravenously vs. intradermally) or varying dosages of the modulating agent and/or vaccine at one or a variety of timepoints. Measurement can be via imaging of, for example, lung tissue, cellular composition of one or more tissues as described in the examples, and/or measurement of antigen-responsive CD4 and CD8 T cells that express the marker of proliferation, Ki-67.

The infection may be caused by an intracellular or extracellular pathogen, as described above. The infection may be caused by one or more bacteria, viruses, parasites, fungi, or other pathogen. In specific embodiments, the infection is an intracellular infection caused by *Mycobacterium tuberculosis* (MTB).

In some embodiments, the pharmaceutical formulation comprises one or more modulating agents, wherein the one or more modulating agents increase expression of IFNγ, IL-2, TNF, and/or IL-17 in systemic and/or lung T cells, as described elsewhere herein. The modulating agents may be administered prior to, at the same time, or subsequent to administration with a vaccine as disclosed herein.

As used in this context, to "treat" means to cure, ameliorate, stabilize, prevent, or reduce the severity of at least one symptom or a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "in need of treatment" as used herein refers to a judgment made by a caregiver (e.g. physician, nurse, nurse practitioner, or individual in the case of humans; veterinarian in the case of animals, including non-human animals) that a subject requires or will benefit from treatment. This judgment is made based on a variety of factors that are in the realm of a caregiver's experience, but that include the knowledge that the subject is ill, or will be ill, as the result of a condition that is treatable by the compositions and therapeutic agents described herein.

Considerations for latent TB infection treatment can include the subject to be treated, including whether the subject has a suppressed or lowered immune system, and this may include HIV-infected persons, organ transplant recipients, young children, and other persons who are immunosuppressed (e.g. taking the equivalent of >15 mg/day of prednisone for 1 month or longer, or taking TNF-a antagonists). Other persons to consider for latent infection treatment can include persons with fibrotic changes on a chest radiograph consistent with old TB, recent contacts of an individual with TB, residents and employees of high-risk settings (e.g. nursing homes, homeless shelters, health care facilities), mycobacteriology laboratory personnel, persons from high-prevalence countries and injection drug users.

The terms "agent", "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As detailed herein, modulate broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to a statistically significant increase or decrease in the measured variable. The modulating agents can be used in an amount sufficient to modify an infection, a change in the amount or degree of infection as compared to in the absence of infection. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, e.g., by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of a cell, cell population, or tissue, or any other infected cell or tissue may be modulated without substantially altering other (unintended, undesired) phenotypic aspect(s).

Preferably, the therapeutic agent may be administered in a therapeutically effective amount of the active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

The amount of the agents which will be effective in the treatment of a particular disorder or condition will depend on the nature of the disorder or condition, and may be determined by standard clinical techniques known by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range of a drug lie within the range known in the art for a particular drug or biologic. Effective doses may be extrapolated from dose-response curves derived from in vitro or animal model test systems. Ultimately the attending physician will decide on the appropriate duration of therapy using compositions of the present invention. The dosage administered will be dependent upon the age, health and weight of the recipient, kind of concurrent treatment, if any, frequency of treatment and the nature of the effect desired.

In some embodiments, the method may further comprise administering the indicated one or more therapeutic agents to the subject. The administration of the one or more therapeutic agents according to the present invention may be carried out in any convenient manner, including by aerosol inhalation, injection, ingestion, transfusion, implantation or transplantation. The therapeutic agent(s) may be administered to a patient subcutaneously, intradermally, intratumorally, intranodally, intramedullary, intramuscularly, by intravenous or intralymphatic injection, or intraperitoneally. In one embodiment, the one or more formulations or therapeutic agents of the present invention are preferably administered by intravenous injection. Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies (e.g., anti-CGRP receptor or anti-CGRP antibodies) are administered in metered-dose propellant driven aerosols. Antibodies may be used as agonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

In an embodiment, the increase of expression of IFNγ, IL-2, TNF, and/or IL-17 effected by the one or more modulating agents occurs in lung T cells. In some embodiments, the lung T cells are lung resident T cells. Lung resident T cells do not recirculate in the blood and thus may not be represented in studies of the systemic immune response. In embodiments, the lung cells are T cells that are recruited to the lung. In some embodiments, the T cells are CD4+ and/or CD8+ T cells. In embodiments, the T cells are helper T cells, naïve T cells, activated T cells, cytotoxic T cells, regulatory T cells, and/or memory T cells. In some embodiments, the T cells are gamma delta T cells, natural killer T cells, innate lymphoid cells. In some embodiments, the T helper cells may be Th1, Th2, Th17, or T follicular helper cells.

In some embodiments, the one or more modulating agents further increase the fractional or overall abundance of CD3+ T cells, CD11c+ macrophages, dendritic cells, or a combination thereof. In some embodiments, the lung resident T cells are CD4+ T cells that also express CD69. In some embodiments, the lung resident T cells also express CD40L. In some embodiments, the CD4+ T cells further express CD103.

In some embodiments, the lung resident T cells are CD8+ T cells. Additional markers that have been associated with T cell residency in the lung, include, but are not necessarily limited to, CD103 (integrin αE); CD11a (ITGAL-1); CD49a (VLA-1α: α1 integrin); VLA-4: α4β1: integrin dimer composed of α4 (CD49d) subunit and β1 (CD29) subunit; CD69; CD101; CD44; and CD62L. CD103 combines with integrin β7 to form a αEβ7 heterodimer and is also involved in leukocyte retention and activation. CD11a combines with β2 to form LFA-1 and is involved in adhesion and co-stimulation. CD49a combines with integrin β1 subunit to form a α1β1 heterodimer and is also involved in adhesion. VLA-4 is involved in adhesion, cell migration, and activation. CD69 binds to and downregulates S1PR1 and is involved in lymphocyte tissue retention. CD101 function in T cell activation and proliferation. CD44 and CD62L both function in leukocyte rolling and homing.

In some embodiments, the one or more modulating agents further increase the expression of one or more of IFNγ, TBX21, RORC, TNFSF8, IL-21R, ABCA1, ADAM19, AGO2, ANKRD11, ARAP2, ARID5B, ATP2A3, ATP2B4, BATF, BCL2L11, BCOR, BHLHE40, BIRC3, BTG1, C3, CBLB, CCDC6, CCDC88C, CCL5, CCND2, CCR5, CCR7, CD2, CD247, CD28, CD3D, CD6, CD84, CHD3, CORO1A, CPD, CYFIP2, DNAJC1, DOCK10, DUSP16, EIF4G3, ELK4, ERC1, ETS1, FAM107B, FOSL2, FOXO3, FRMD4B, FURIN, FYB, GIMAP7, GPRIN3, GZMB, HERC1, HIPK2, HIVEP1, HOPX, HTATSF1, HUWE1, ICOS, IFITM1, IKZF1, IL1R1, IRF4, ITGA4, KAT6A, KMT2A, KMT2E, LAT, LAT2, LCK, LOC698693, LOC703029, LOC710951, LPIN1, LTA, LTB, LYST, MAF, MAP3K14, MAP4K4, MPHOSPH8, MPRIP, NCOA1, NCOA2, NCOA3, NEDD4L, NOTCH2, PCNX, PHIP, PIK3CD, PITPNM1, PITRM1, POLR1B, PPP1R16B, PRDM1, PRKCH, PRKCQ, PRRC2B, RASGRP1, RASSF5, RBL2, RCSD1, REST, REV3L, RGS1, RNF19A, RORA, SAMS1, SATB1, SEMA4D, SETD7, SH3KBP1, SLA, SLAMF1, SMARCA2, SOS1, SPOCK2, SPTAN1, SSH1, STK17B, STK4, SUZ12, TLE3, TNFAIP3, TNFRSF1B, TNFRSF8, TPR, TRAF1, UBE2O, USE1, WHSC1L1, WNK1, YLPM1, ZBED2, ZBTB38, ZNF281, AKAP1, APOBEC3A, ARID1A, CMAH, CSK, DGKA, DPP4, ECE1, EPHB2, FAM53B, FGFR10P2, FOXO1, GIMAP8, HEG1, IFI27, LAIR1, LAMP3, LSP1, MAMU-A, MMP25, NDRG1, PDGFA, PLA2G2D, RTEL1, SSRP1, SYT11, TGFBI, TMEM176B, TRERF1, UBD, UBTF, ARHGEF6, CLSTN1, DUSP4, FBXW2, LAD1, LY75, MIIP, PAPSS2, SCML4, SIGLEC1, VDR, ZC3H4, GPR171, HECA, HIVEP3, ID2, OGFRL1, PARP1, PSIP1, RASA3, RFTN1, SERPINB9, SLAMF7, SLC39A14, TNFRSF9, ANTXR2, BMP2K, BRD9, CLDND1, EHD1, ETV3, GABPB1, IL2RA, MCOLN2, NAV1, NFKBIA, NSMCE1, PARP8, SPECC1, TMEM176A, TNFRSF25, or TNIP1 in a cell, or the fractional or total abundance of cells that express them. In some embodiments, the one or more modulating agents increases the fractional or absolute number of Vγ9+ γδ T cells and MAIT cells. In some embodiments, the Vγ9+ γδ T cells and MAIT cells are lung resident cells.

In some embodiments, the one or more additional cell markers may include, but are not necessarily limited to, CD3E, DENND3, FAM129A, GCN1, MAP3K5, RRP1B, SOS2, USP1, WHSC1, ARHGAP4, GZMH, IL27RA, NOTCH1, PRF1, SYNE3, ISY1, ATXN10, EMB, EVL, LBH, or SLCO4A1.

In some embodiments, the TNF is TNFβ or TNFα.

In some embodiments, the one or more modulating agents increase the ratio of T cells to macrophages. In certain embodiments, known techniques can be used to determine modulating agents that increase the ratio of T cells to macrophages, as described in the examples. In an embodiment, ratio of macrophages to T cells in may be determined by scRNA-seq or flow cytometry.

In some embodiments, the one or more modulating agents are comprised in a Bacille Calmette-Guerin (BCG) vaccine.

In some embodiments, the vaccine is administered intradermally, intramuscularly, intravenously, or by aerosol. In specific embodiments, the vaccine is administered intravenously.

In some embodiments, the one or more modulating agents modulates the microenvironment of a cell mass. In some embodiments, the cell mass is a granuloma. In some embodiments, the cell mass is a fibroma, as described elsewhere herein.

In some embodiments, the present disclosure provides methods of treating or preventing diseases by modulating a microenvironment of a cell or cell mass. The methods may comprise administering one or more modulating agents to modulate the number and/or function of certain types of cells. In some examples, the methods comprise administrating an effective amount of one or more modulating agents that modulates mast cells, plasma cells, Th1-Th17 cells, and/or CD8+ T cells in the subject.

In some embodiments, the present disclosure provides cells or cell lines in which one or more genes is modulated, including via adoptive cell transfer. Such modulation includes expression of the one or more genes. The expression of the gene(s) by the modulation may be higher than a counterpart wildtype cell or cell line. Alternatively or additionally, the modulation may include suppression of the one or more genes. The suppression of the gene(s) by the modulation may cause lower expression of the genes compared to a counterpart wildtype cell or cell line. In some cases, the present disclosure provides mast cell or cell lines in which one or more genes is modulated. For examples, the mast cell or cell lines may express one or more target genes herein, e.g., expressing one or more of: IL-33, IL-1R1, and genes in the IL-13 signaling pathway. In some cases, the present disclosure provides Th1-Th17 cell or cell lines in which one or more genes is modulated. For examples, the Th1-Th17 cell or cell lines may express one or more target genes herein, e.g., INF-γ, INF-γ receptor 2, TGFβ1, TGFβ receptor 3, CCL5, and genes in the INF-γ and TGFβ signaling pathways.

Adoptive Cell Transfer

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and allow insertion of transgenes into desired loci.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many Mtb infection related cells present.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™ BD™ LSR II, and FACSCalibur™ (BD Biosciences, San Jose, Calif.).

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000-fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, a patient in need of a T cell therapy may be conditioned by a method as described in International Patent Publication No. WO2016191756 comprising administering to the patient a dose of cyclophosphamide between 200 mg/m$^2$/day and 2000 mg/m$^2$/day and a dose of fludarabine between 20 mg/m2/day and 900 mg/m$^2$/day.

In some embodiments, the modulation of genes or protein may be increasing the expression, activities, and/or stability of the genes or proteins. In certain embodiments, the modulation of genes or proteins may be decreasing the expression, activities, and/or stability of the genes or proteins.

Further embodiments are illustrated in the following Examples which are given for illustrative purposes only and are not intended to limit the scope of the invention.

EXAMPLES

Example 1—Experimental Design and Safety

Figure 2:
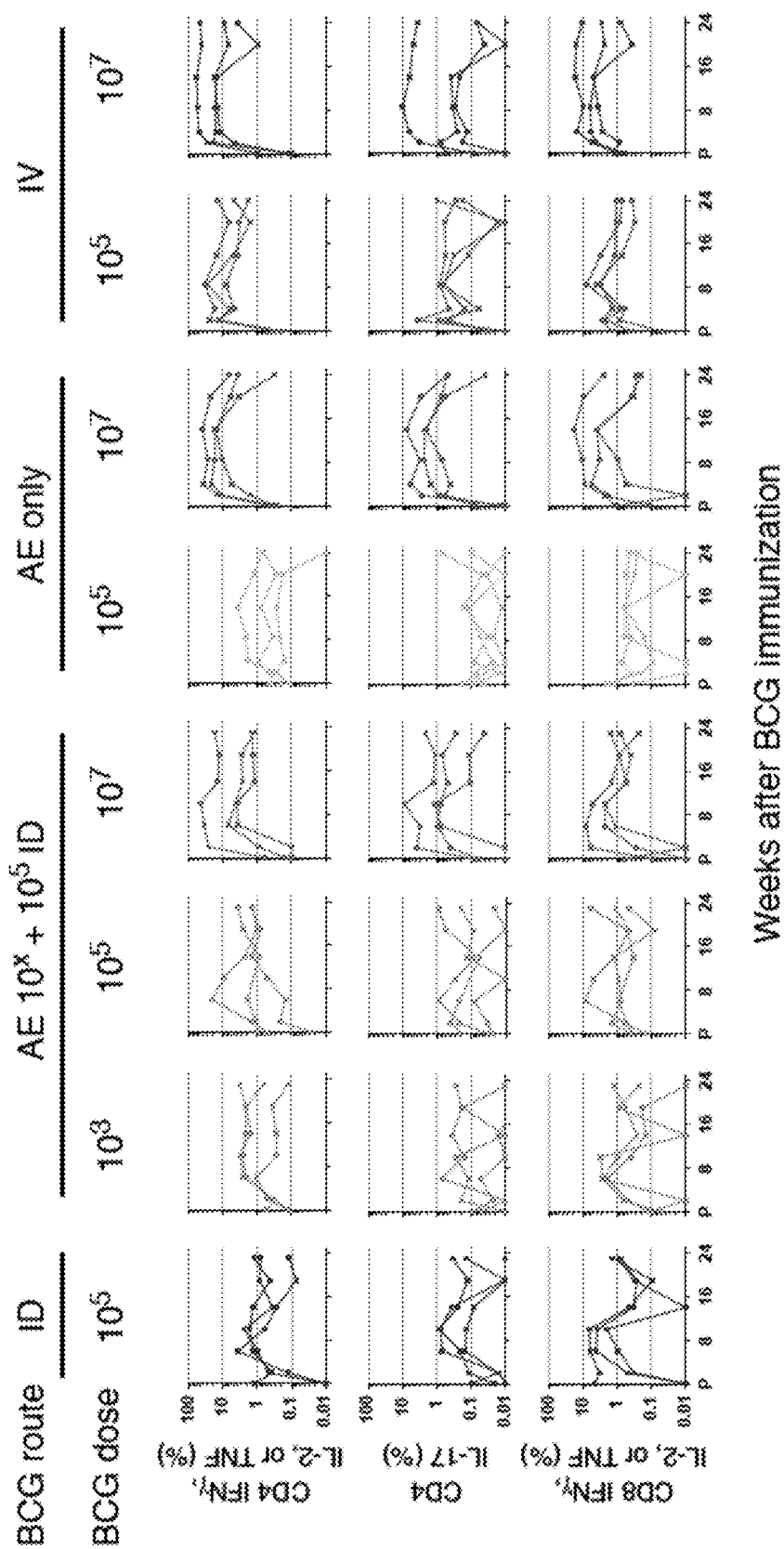
FIG. 2—Dose-finding pilot study in NHP. To determine a BCG dose and vaccination route that would elicit greater immune responses in the BAL compared to the standard human BCG vaccine ($5 \times 10^5$ CFU ID), 3 rhesus macaques per group (24 total animals, 22 male and 2 female; 6-9 years old) were immunized with BCG by different routes and nominal doses as follows: ID only ($1 \times 10^5$ CFU); AE ($1 \times 10^3$, $1 \times 10^5$, or $1 \times 10^7$ CFU) plus ID ($1 \times 10^5$ CFU)), $1 \times 10\times$ refers to the three doses shown for AE where x=3, 5, or 7; AE only ($5 \times 10^5$ or $5 \times 10^7$); IV only ($5 \times 10^5$ or $5 \times 10^7$ CFU). Actual BCG doses can be found in FIG. 3A (Pilot cohorts a-c). Prior to (Pre, P) and at various weeks after BCG immunization, BAL was harvested from each animal to perform in vitro T cell stimulation and flow cytometric cytokine analysis. Shown are the frequencies of memory CD4 T cells producing any combination of IFNγ, IL-2, or TNF (top), memory CD4 T cells producing IL-17 (with or without other cytokines; middle), and memory CD8 T cells producing IFNγ, IL-2, or TNF (bottom) in response to PPD stimulation for 3 individual animals in each vaccine group over time. Samples were analyzed as in methods and are presented on a log scale. No statistical comparisons were performed in this pilot study.
Figure 3B:
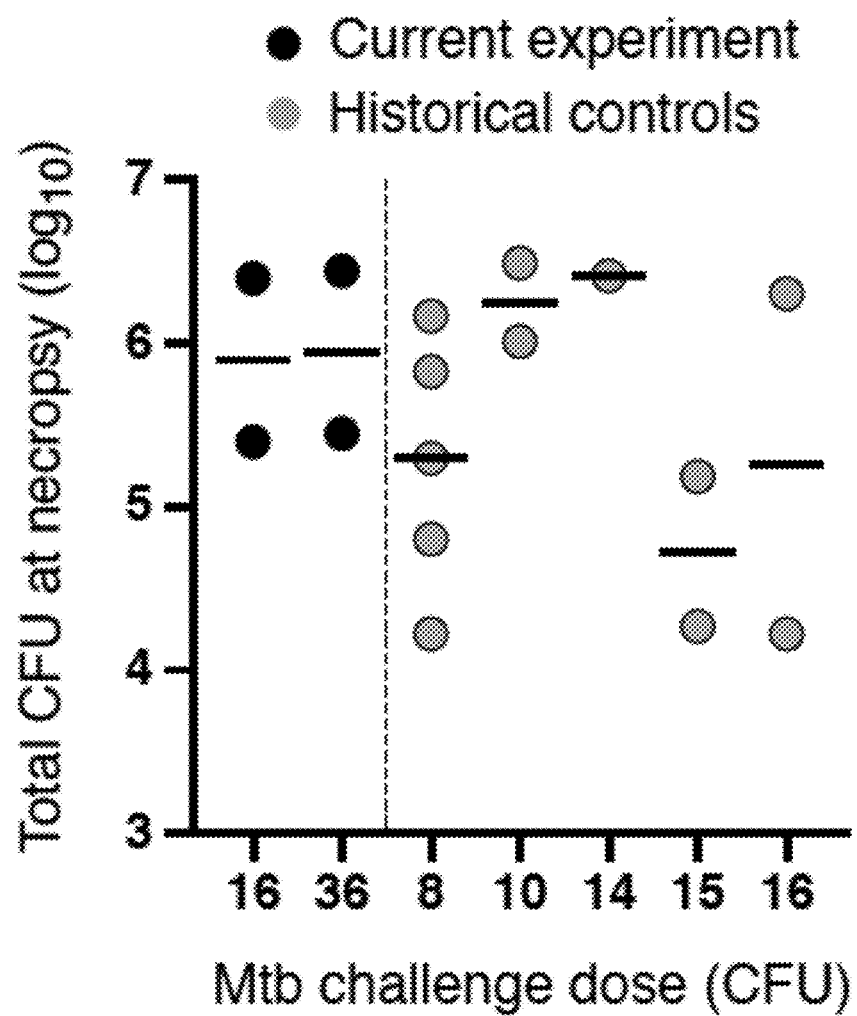

The central aim of this study was to assess how the route and dose of BCG vaccination influence systemic and tissue-resident immunity and protection following Mtb challenge. To test this, rhesus macaques were vaccinated with $5 \times 10^7$ CFU BCG (Danish) by ID (ID$_{high}$), AE, or IV routes, or with a combination of AE ($5 \times 10^7$ CFU) and ID ($5 \times 10^5$ CFU; AE/ID) (FIG. 1A). The immune responses and protective efficacy of these vaccine groups were compared to animals that received the standard human dose of ID BCG ($5 \times 10^5$ CFU, ID$_{low}$). A BCG dose of $5 \times 10^7$ CFU was selected for AE and IV vaccine groups based on a pilot study showing increased antigen-responsive T cell responses in bronchoalveolar lavage (BAL) compared to animals that received $5 \times 10^5$ CFU by these routes (FIG. 2). Following BCG immunization, blood and BAL immune responses were assessed over 24 weeks, after which NHP were challenged with a low dose of Mtb (FIG. 1B). Additional animals in each vaccine group were not challenged but instead euthanized 1 or 6 months after vaccination for extensive immune analysis of tissue responses (FIGS. 3A and 3B). To assess protection, unvaccinated and BCG-immunized animals were non-invasively monitored by PET CT scanning for 12 weeks following Mtb challenge (White et al. *J Vis Exp:JoVE* doi:10.3791/56375 (2017)). All animals underwent necropsy to quantify mycobacterial burden, granuloma formation and overall pathology (Maiello et al. *Infect Immun* 86:doi:10.1128/iai.00505-17 (2018)). A summary of all NHP used in the study and the doses of BCG and Mtb administered for vaccination and challenge is shown in FIGS. 3A and 3B.

To assess the safety of BCG vaccinations, a number of clinical parameters were measured (FIGS. 4A-4D). Post-vaccination changes were observed predominantly after IV BCG administration; all were transient. Specifically, there was a 1.6° F. increase in body temperature at day 1, which resolved by day 2; a two-fold increase in ALT/AST above the normal range of 20 IU/L, which resolved by day 28; and increased CRP up to a median of 400 µg/ml at day 2, which resolved by day 14. No clinical signals, such as lethargy, appetite suppression or weight loss, were observed up to time of Mtb challenge, 24 weeks later.

Figure 1E:
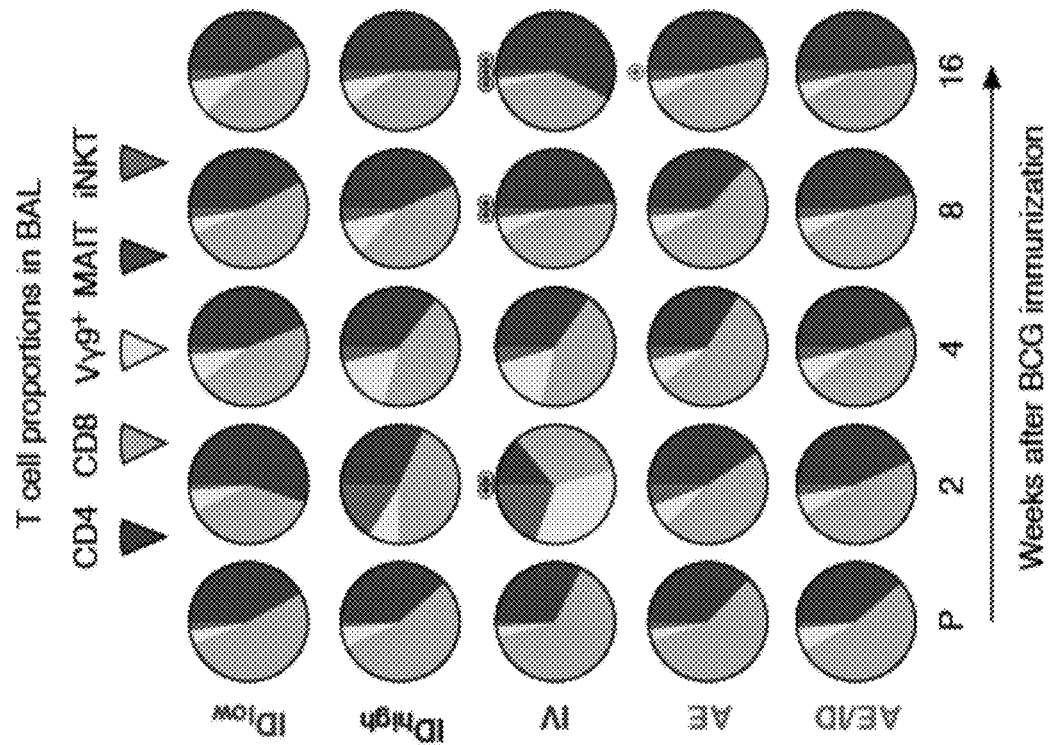
Figure 1D:
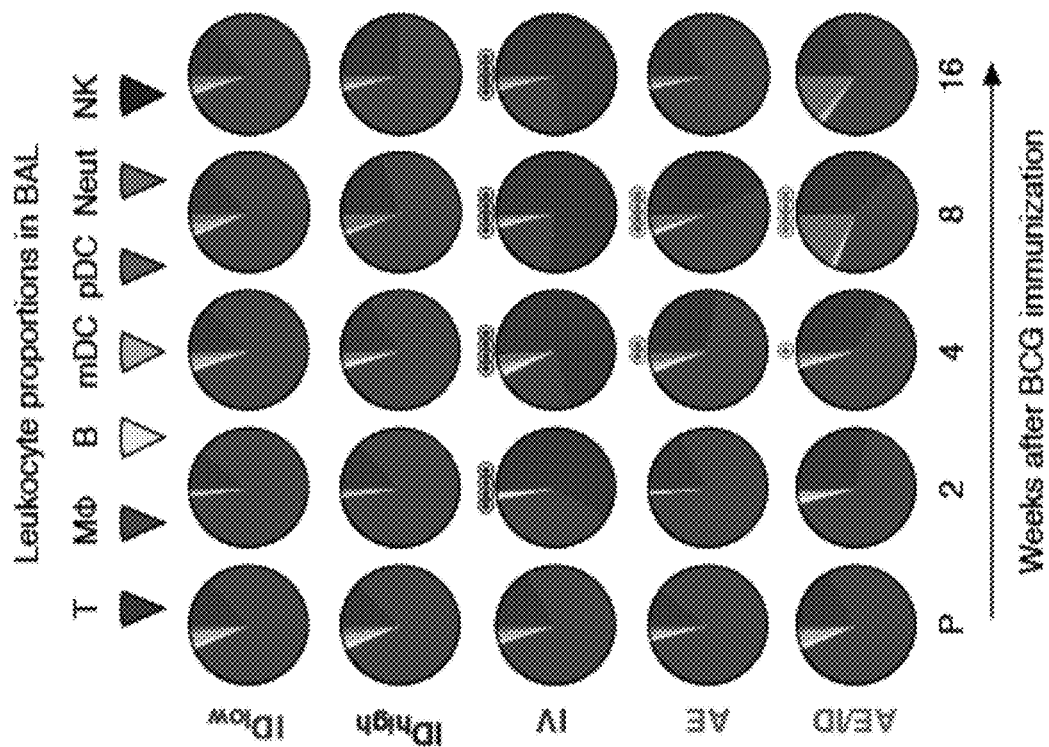

Example 2—Cellular Composition of Bronchoalveolar Lavage (BAL) and Blood after BCG Vaccination Since generating immune responses in the lung was a major focus of the study, Applicants first assessed whether the route of BCG vaccination altered the number or composition of leukocytes in BAL following vaccination. Only the IV BCG vaccinated group demonstrated significant changes in BAL cell numbers: a 5-10-fold increase in the number of total cells (FIG. 5A), accounted for largely by T cells (FIGS. 1C and 5B). This influx of T cells altered the cellular composition of BAL from ~75% macrophages and ~15% T cells prior to vaccination to ~65% T cells and ~30% macrophages, even 6 months after IV BCG (FIGS. 1D and 6A). To further delineate the composition of BAL T cells, Applicants assessed the proportions of CD4 and CD8 T cells, as well as non-classical T cells (γδ, MAIT, and iNKT) that may also have a role in protection against TB (Greene et al. *Mucos Immunol* 10:802-813 (2017); Joosten et al. *Vaccine* 37:3022-3030 (2019); Qaqish et al. *J Immunol* 198:4753-4763 (2017)). Two weeks after vaccination, there was a substantial but transient increase in the proportion of Vγ9$^+$ γδ T cells and MAIT cells following IV BCG, and a trend toward increased Vγ9$^+$ γδ T cells and MAIT cells following BCG ID$_{high}$ (FIGS. 1E and 6B). However, by 8 weeks the proportions of these non-classical T cells contracted to pre-vaccination levels.

Figures 7A, 7B:
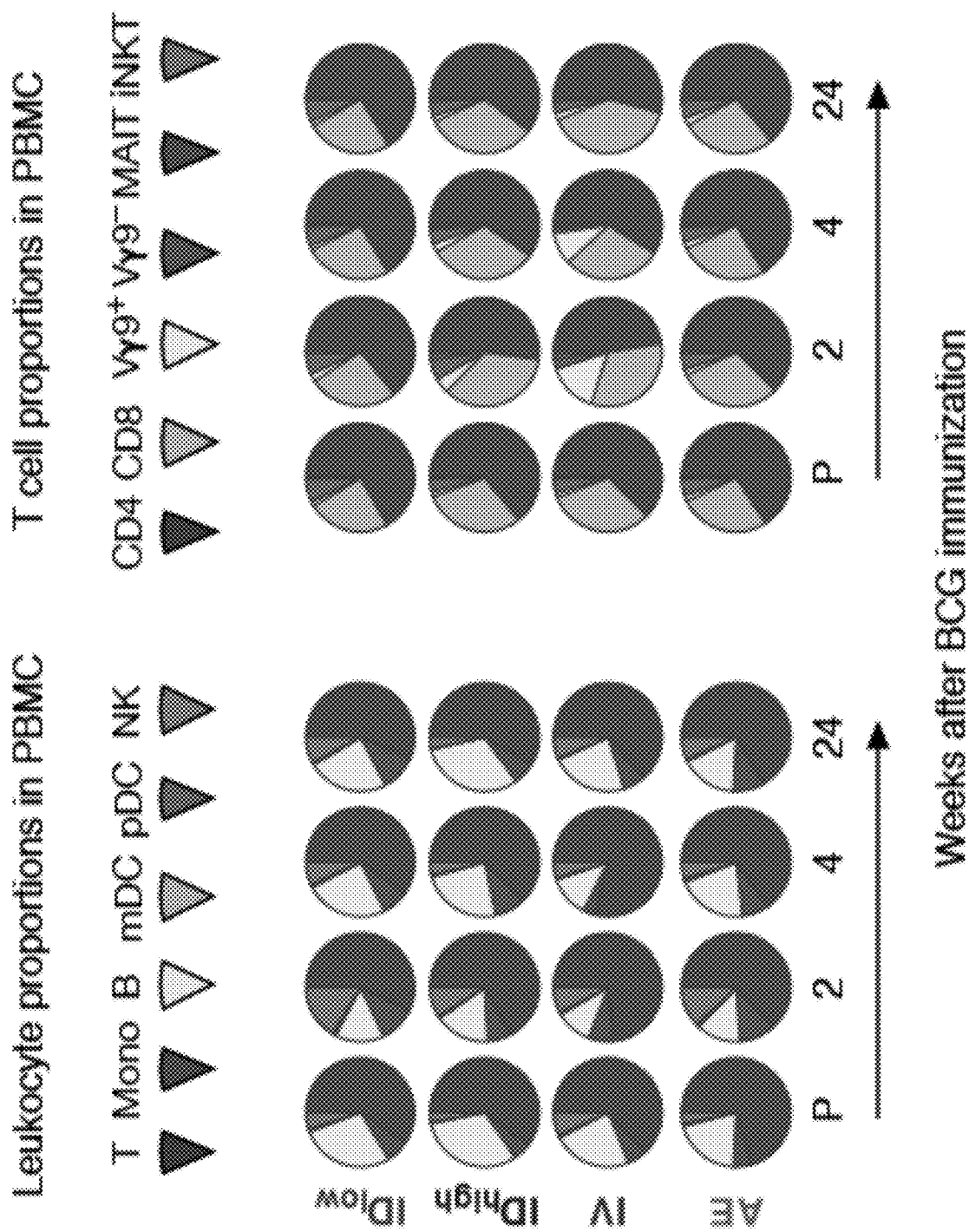
FIGS. 7A-7B—Proportions of leukocyte and T cell subsets in PBMC after BCG immunization. Pie charts showing proportions of indicated leukocytes (7A) or T cell subsets (7B) in PBMC for each vaccine group from pre (P) to 24 weeks after BCG immunization, identified using multi-parameter flow cytometry. Pie graphs represent the average proportions from 3 animals per vaccine group (cohort 4). T, T cells; Mono, monocytes; B, B cells; mDC, myeloid dendritic cells; pDC, plasmacytoid dendritic cells; NK, NK cells; CD4, CD4 T cells; CD8, CD8 T cells; Vγ9+/−, Vγ9+/− gamma delta T cells; MAIT, mucosal associated invariant T cells; iNKT, invariant natural killer T cells.

A similar analysis was performed to determine how the route of BCG immunization influenced the composition of leukocytes in blood (peripheral blood mononuclear cells, PBMC). IV BCG induced a transient increase in Vγ9$^+$ γδ T cells but not MAIT cells (FIG. 7B). The proportions of NK cells, which have recently been suggested to correlate with protection against TB in blood (Choudhury et al. *Nature* 560:644-648 (2018); Suliman et al. *J Immunol* 197:1100-1110 (2016)) were not altered after BCG vaccination in blood or BAL (FIGS. 7A and 1D). In addition, Applicants analyzed PBMC for potential effects on innate immunity following BCG vaccination. Studies in humans show that recent Mtb exposure or BCG vaccination leads to increased monocyte-derived cytokine production (TNF, IL-1β, or IL-6) from microbially-stimulated PBMC, a process termed "trained innate immunity," that leads to BCG growth inhibition by PBMC in vitro (Joosten et al. *J Clin Invest* 128:1837-1851 (2018); *J Innate Immun* 6:152-158 (2014)).

There was no increased production of these innate cytokines in stimulated PBMC after ID or IV BCG immunization (FIG. 8).

Overall, these data show that IV BCG immunization, in contrast to AE or ID, results in significant and sustained recruitment of T cells to the airways and substantially alters the ratio of T cells to macrophages.

Example 3—Antigen-Responsive Adaptive Immunity Following BCG Immunization

Figure 9A:
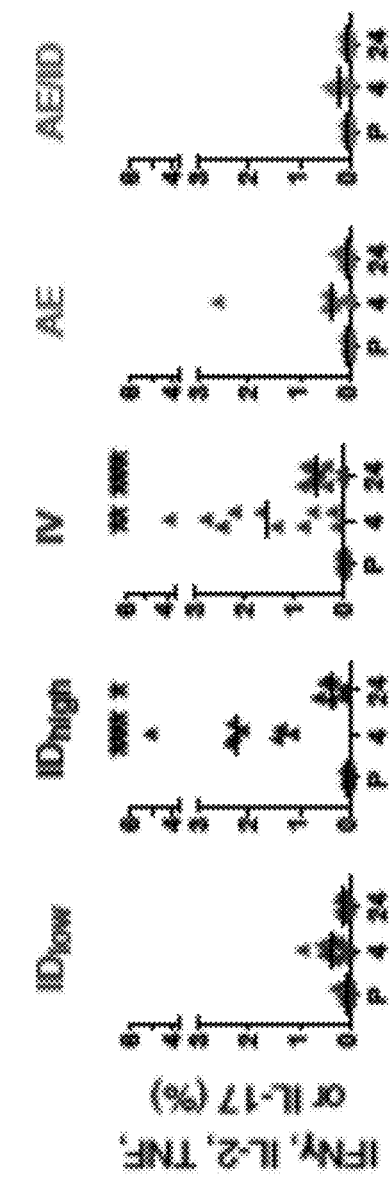
Figure 9B:
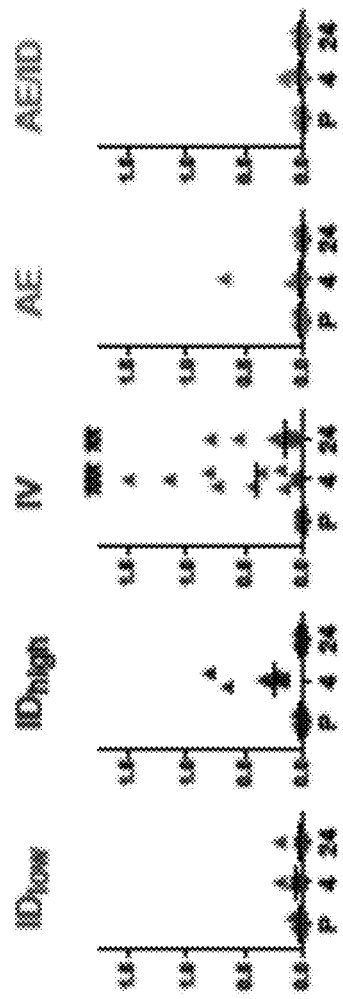
Figure 9C:
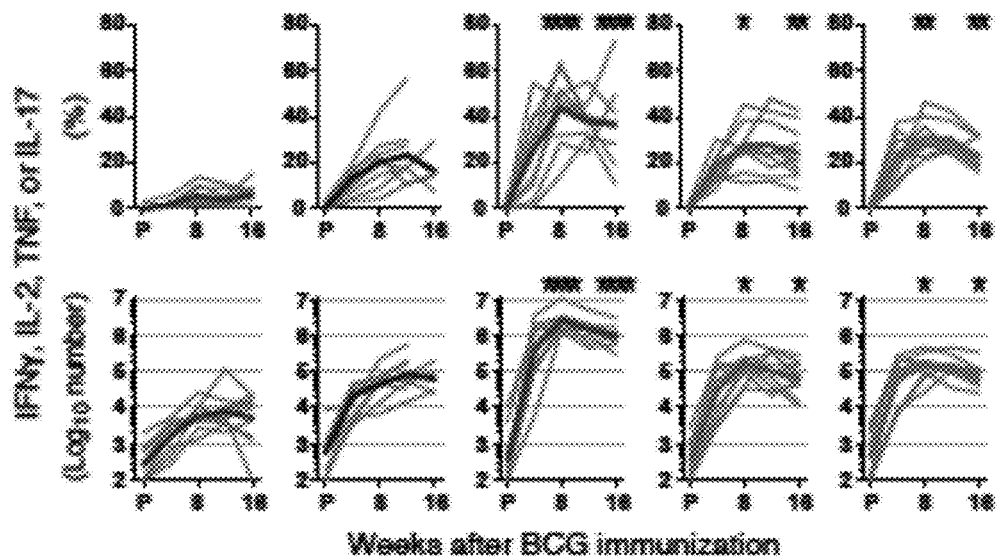
Figure 9D:
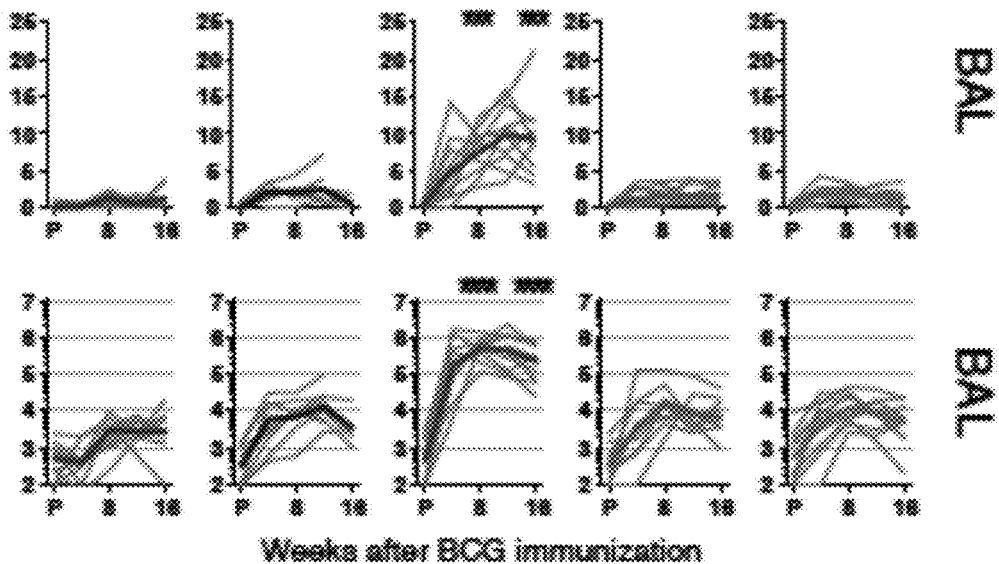
Figure 10A:
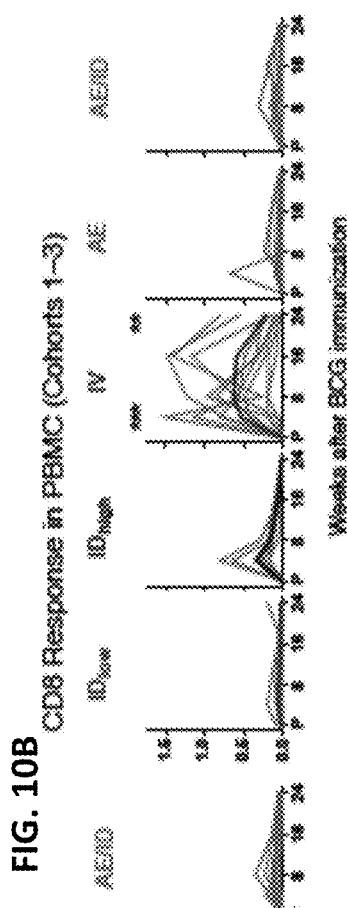
Figure 10C:
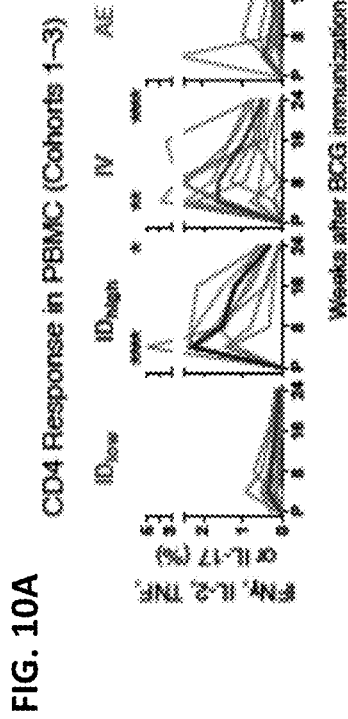
Figure 10B:
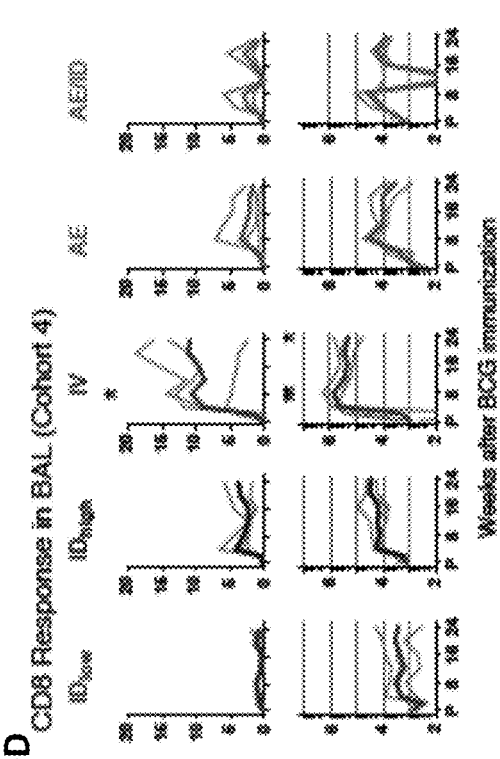
Figure 10D:
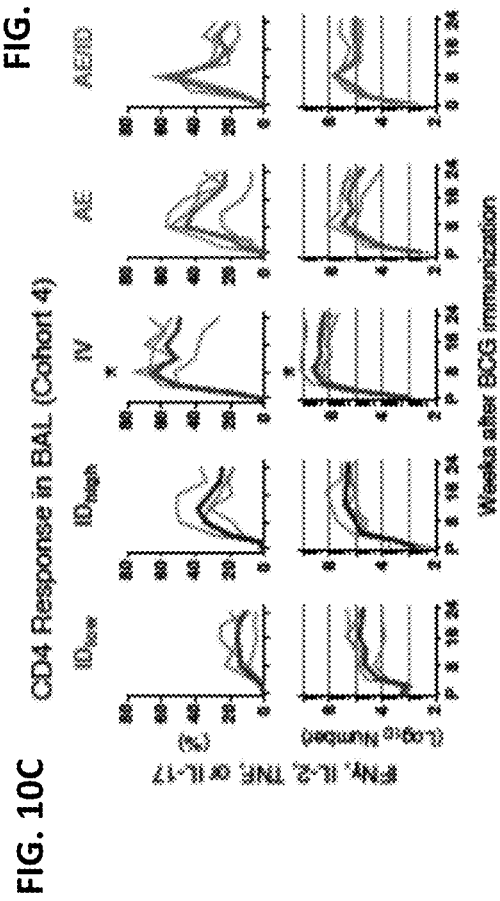

Applicants next evaluated how the route and dose of BCG influenced the antigen-responsive T cell responses. CD4 T cells are required for mediating protection against TB (Lin et al. *AIDS Res Hum Retroviruses* 28:1693-1702 (2012)) while CD8 T cells can also have a role in vaccine-elicited protection and control of TB following infection (Chen et al. *PLoS Pathogens* 5:e1000392 (2009)). The magnitude of mycobacterial antigen (e.g., PPD)-responsive CD4 and CD8 T cells was assessed in PBMC and BAL by determining the frequency or number of CD4 and CD8 T cells producing any of the canonical cytokines (IFNγ, IL-2, TNF, or IL-17) shown to be associated with protection against TB (Khader et al. *Nat Immunol* 8:369-377 (2007); Gideon et al. *PLoS Pathogens* 11:e1004603 (2015)) (FIGS. 9A-9D and 10A-10J). At the peak of the response in PBMC (week 4 post-BCG), antigen-responsive cytokine-producing CD4 T cells were higher in NHP immunized with $ID_{high}$ or IV BCG compared to $ID_{low}$ BCG; such responses declined over time but remained elevated compared to $ID_{low}$ animals at the time of challenge (week 24 post-BCG; FIGS. 9A and 10A, 10G). Similarly, CD8 responses in PBMC of IV-immunized NHP were greater than $ID_{low}$ animals at both time points (FIGS. 9B and 10B, 10H). Antigen-responsive T cells in BAL were highest at 8 weeks post-BCG and, in contrast to kinetics of PBMC, were largely maintained until the time of challenge (FIGS. 9C, 9D, 10C, and 10D). $ID_{high}$ or AE BCG elicited 10-fold more PPD-responding CD4 T cells in BAL than $ID_{low}$ BCG, with 20-30% of CD4 T cells responding to Mtb antigens. IV BCG elicited 100-fold more antigen-responsive CD4 T cells than $ID_{low}$ BCG, with ~40% of cells responding to PPD. Furthermore, only IV BCG induced a significant increase in the frequency and number of antigen-responsive CD8 T cells compared to $ID_{low}$ BCG; these persisted in BAL for at least 16 weeks (FIGS. 9D and 10D). Central (Tcm) and transitional (Ttm) memory cells comprised the majority of peak CD4 T cell responses in PBMC across all vaccine groups, whereas Ttm cells were predominant in BAL (FIGS. 10E, 10F). Of note, IV BCG-vaccinated animals had the largest proportion of Ttm in PBMC and effector (Tem) memory cells in BAL.

While the magnitude of the total Mtb antigen-responsive T cell cytokine responses is one important parameter for immune protection, the composition of the cytokine responses at the single-cell level, or "quality" of the response, can reveal distinct functional differences that associate with protection against Mtb and other pathogens (Darrah et al. *Nat Med* 13:843-850 (2007); Lewinsohn et al. *Frontiers Immunol* 8:1262 (2017)). Here, the quality was defined by the relative proportion of antigen-stimulated cells producing every combination of IFNγ, IL-2, and TNF, with or without IL-17. Amongst vaccine groups, there were no differences in the quality of CD4 T cell responses nor CD8 T cell responses in PBMC (FIGS. 11A-11D) or BAL (FIGS. 9E and 12A-12D), despite the striking differences in the magnitude of these responses. Of note, ~90% of the CD4 T cell responses were comprised of Th1 cytokines with <10% also producing IL-17; most IL-17 producing CD4 T cells co-expressed Th1 cytokines (FIG. 9E, pie charts).

Figures 11A, 11B:
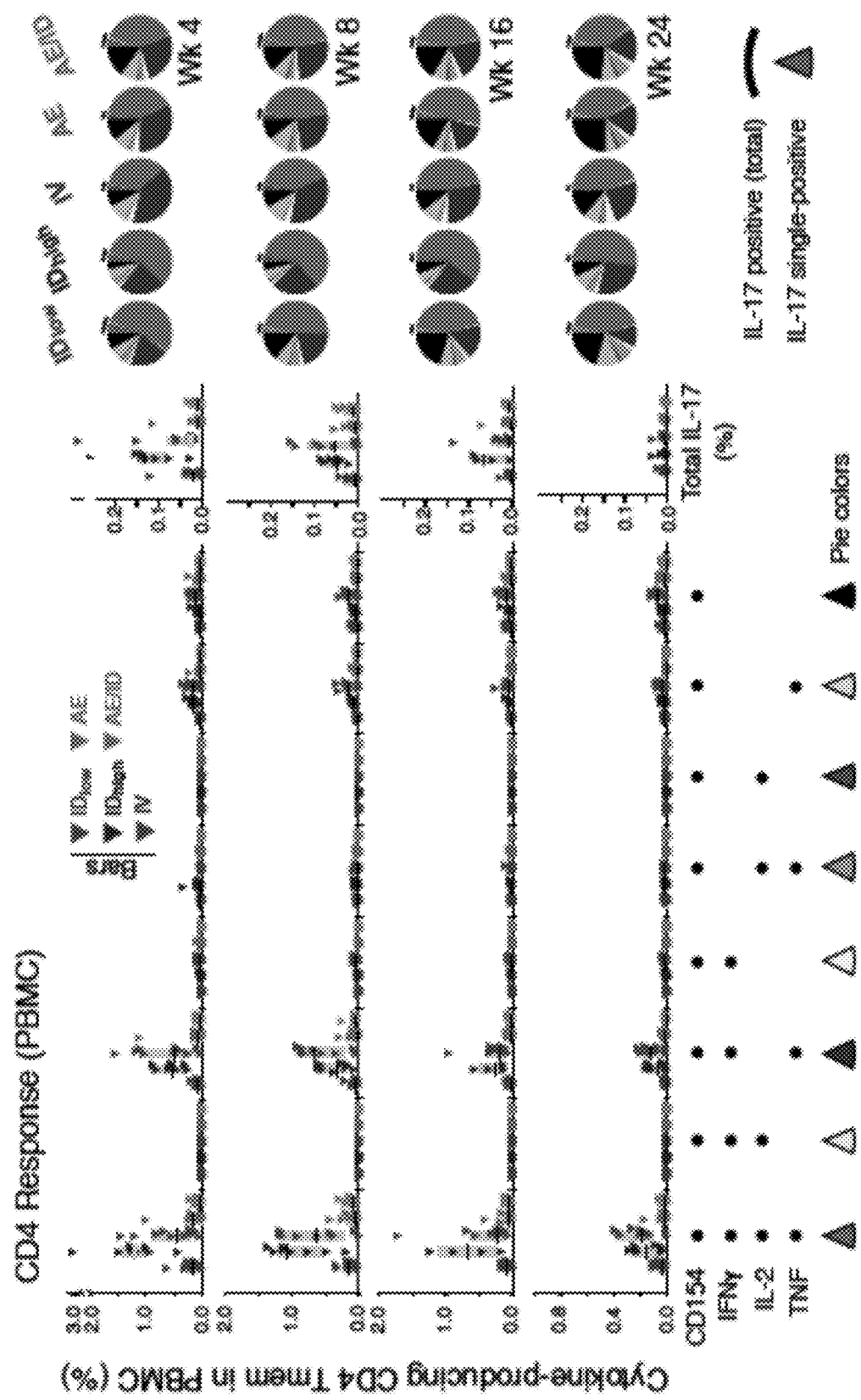
FIGS. 11A-11D—Quality of T cell responses in PBMC after BCG immunization. (11A) The frequency of PPD-responsive CD4 memory T cells in PBMC expressing CD154 and any combination of IFNγ, IL-2, or TNF, or the frequency of total IL-17 production, for animals in each vaccine group (challenge cohorts 1-3) at 4, 8, 16 and 24 weeks after BCG immunization. (11B) The proportions of total cytokine production comprising each cytokine combination as shown in (11A), averaged for animals in each group at each time point. Individual animal responses are shown with interquartile range (bar) and median (horizontal line). Note that the proportion of the response producing IL-17 (with or without other cytokines) is indicated with a black arc and CD4 T cells that express CD154 only are the black pie section. (11C) The frequency of PPD-responsive CD8 memory T cells in PBMC expressing any combination of IFNγ, IL-2, or TNF in PBMC after BCG immunization. (11D) Proportion of total cytokine response comprising each individual cytokine combination for vaccine groups that measurable CD8 T cell responses.
Figures 11C, 11D:
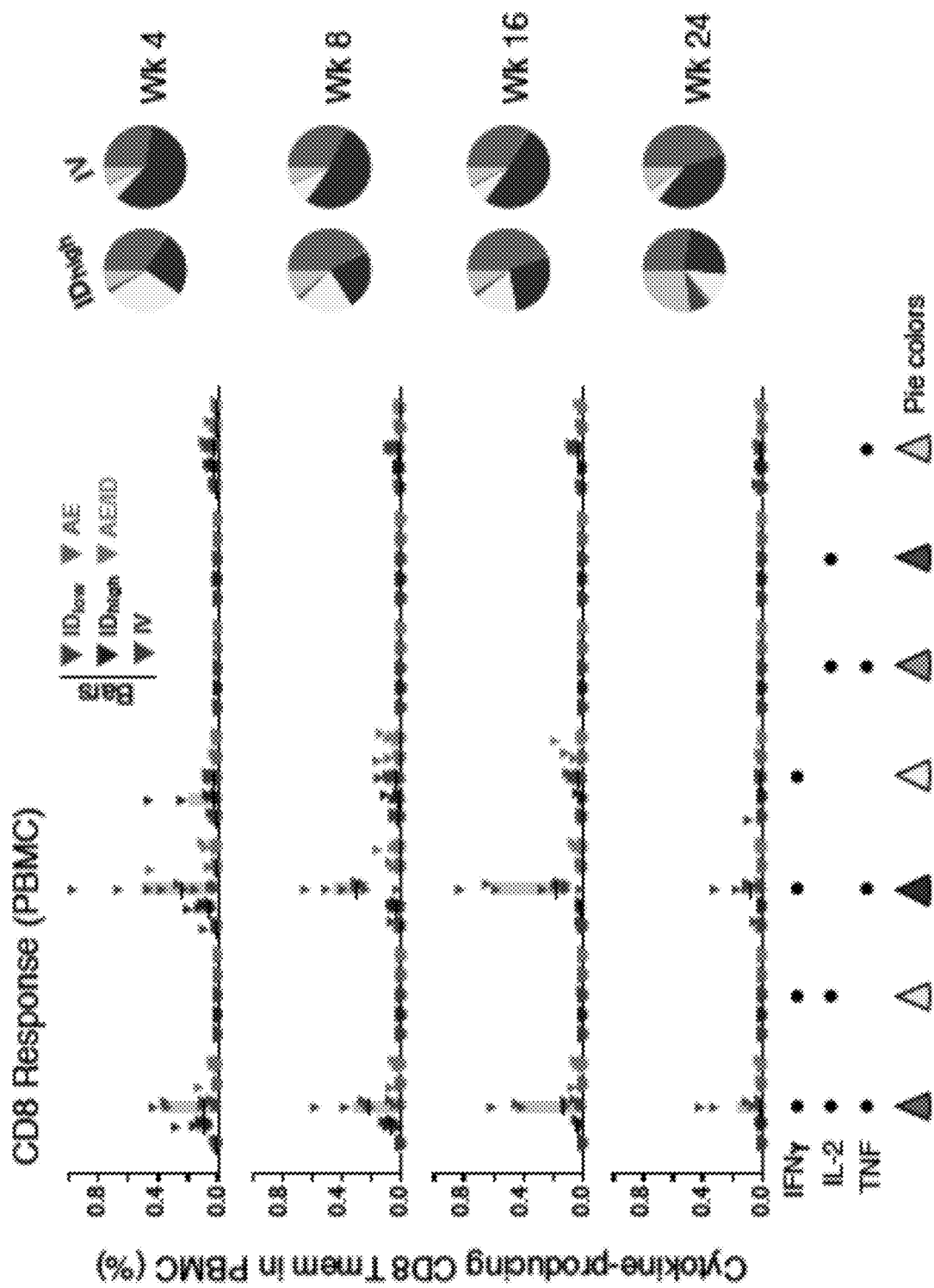
Figures 12A, 12B:
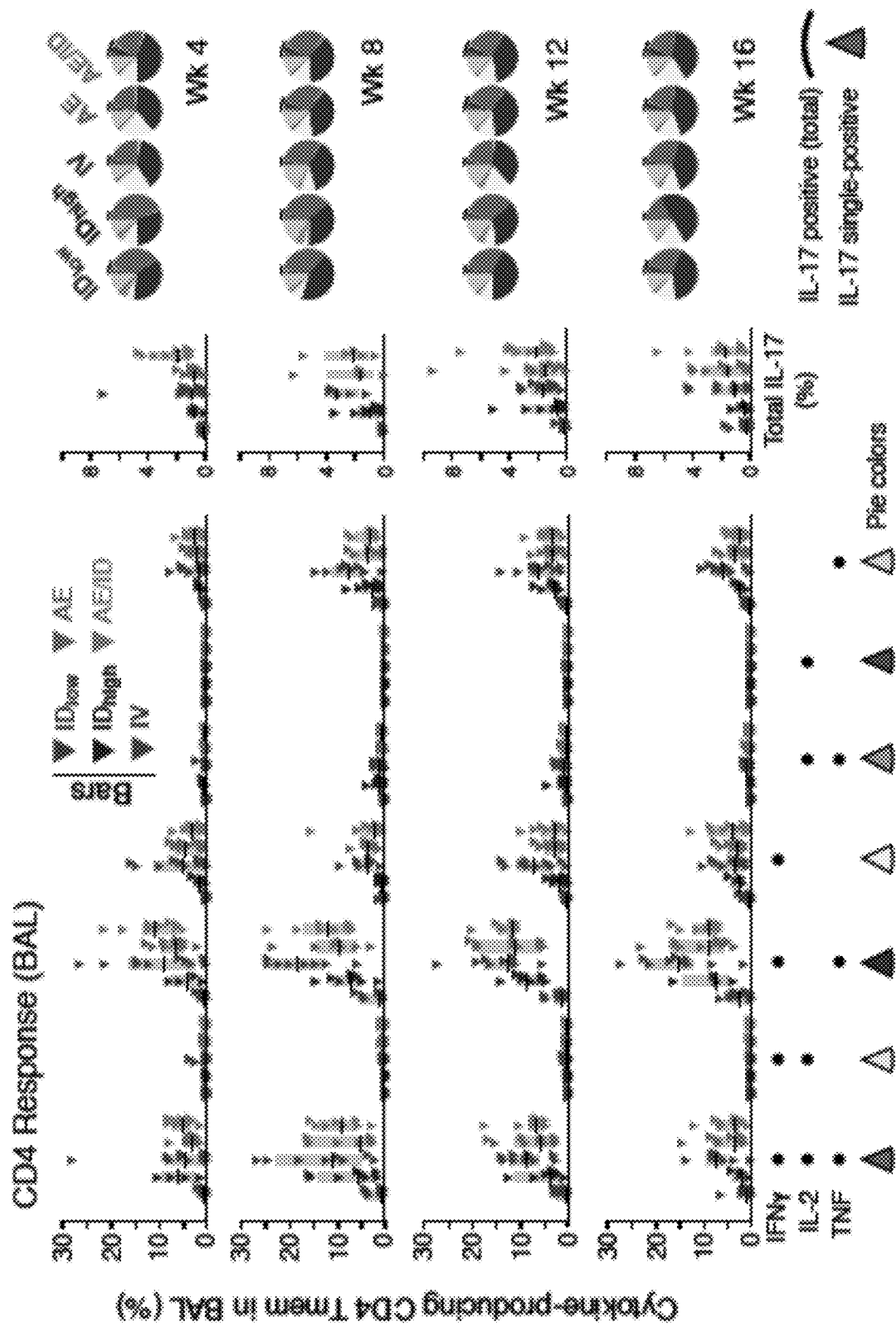
FIGS. 12A-12D—Quality of T cell responses in BAL after BCG immunization. (12A) The frequency of PPD-responsive CD4 memory T cells in BAL expressing any combination of IFNγ, IL-2, or TNF, or the frequency of total IL-17 production, for animals in each vaccine group (challenge cohorts 1-3) at 4, 8, 12 and 16 weeks after BCG immunization (BAL was not sampled within 8 weeks of Mtb challenge). Individual animal responses are shown with interquartile range (bar) and median (horizontal line). (12B) The proportion of total cytokine production comprising each cytokine combination as shown in (12A) averaged for animals in each group at each time point. Note that the proportion of the response producing IL-17 (with or without other cytokines) is indicated with a black arc and IL-17-single positive cells are represented by the grey pie section. CD154 expression was not measured in the BAL. (12C, 12D) The frequency and proportion CD8 T cell responses following PPD stimulation is as described above.
Figures 12C, 12D:
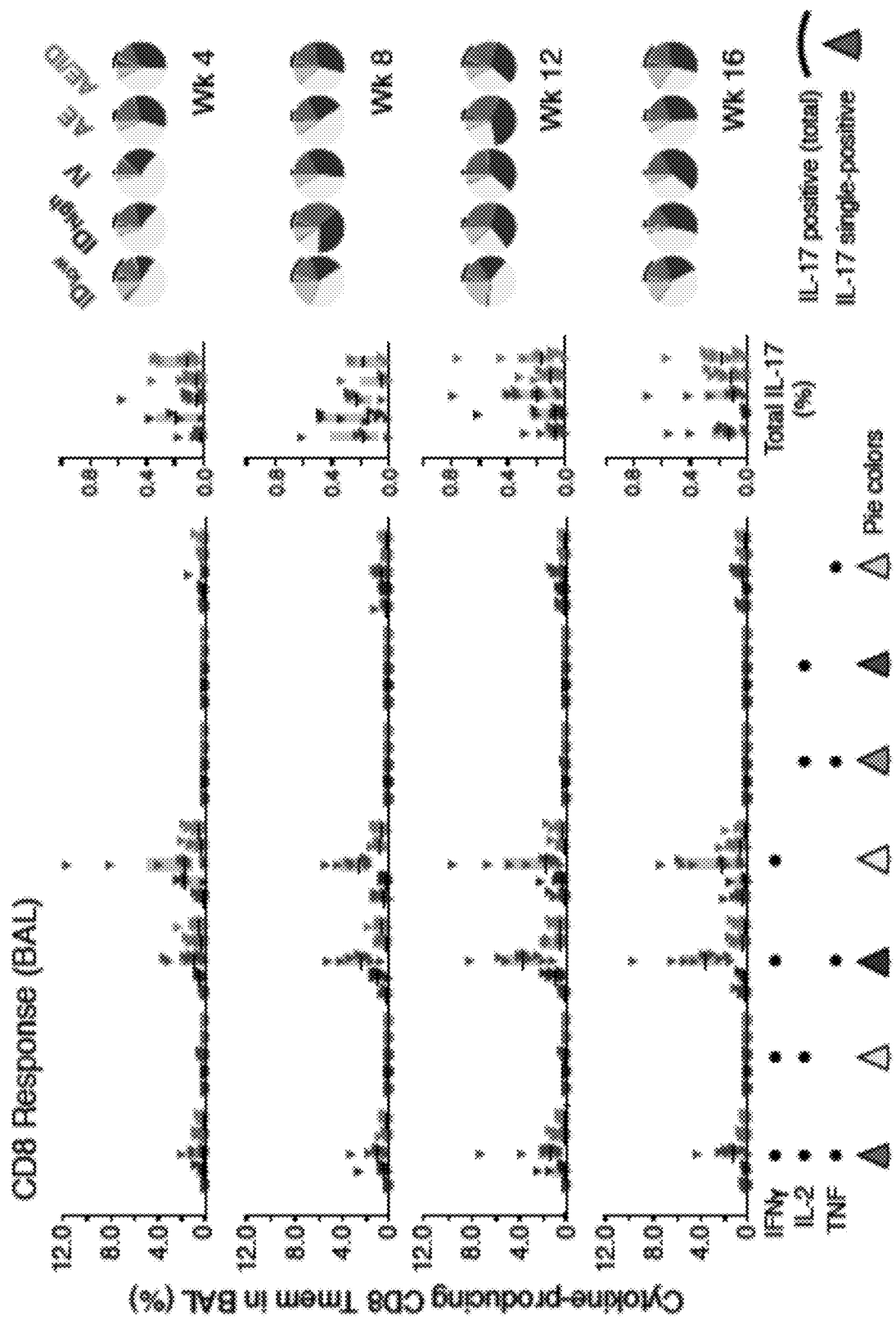

In addition to the canonical cytokines associated with protection against TB, there is evidence for a CD4-dependent, IFNγ-independent mechanism of protection against TB (Orr et al. *J Infect Dis* 212:495-504 (2015); Sakai et al. *PLoS Pathogens* 12:e1005667 (2016)). To assess whether there were antigen-responsive cells other than those producing Th1 or Th17 cytokines, stimulated PBMC were stained for CD154 (CD40L), a sensitive marker for detection of all antigen-stimulated CD4 T cells (Chattopadhyay *Nat Protocol* 1:1-6 (2006)). Indeed, ~10% of PPD-responsive cells in PBMC from all vaccine groups did not produce IFNγ, IL-2, TNF or IL-17 (FIGS. 11A, 11B). These data suggest that there may be additional underlying qualitative and potentially functional differences amongst T cells from the various vaccine groups not measured by the canonical cytokines most commonly used to assess BCG-elicited immunity.

Figure 13B:
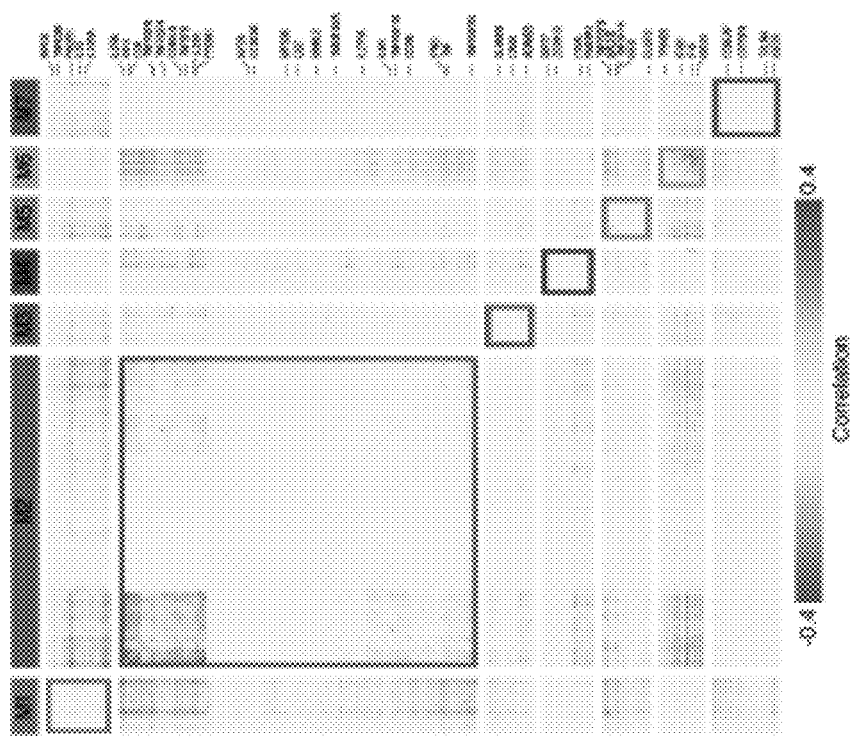
FIGS. 13A-13D—Identification of gene modules and distribution of module scores. (13A) Uniform Manifold Approximation and Projection (UMAP) plots of BAL cells collected at weeks 13 and 25 (162,490 total cells) after BCG immunization shaded by time point (top left), PPD stimulation condition (top right), and cell type (week 13, bottom left; week 25, bottom right). (13B) Gene-gene correlation heatmap showing significant gene modules (M1-M7; top) identified among week 13 stimulated BAL T cells with select genes (right) highlighted. (13C) t-Distributed Stochastic Neighbor Embedding (t-SNE) plots of stimulated BAL T cells from week 13 (left) and week 25 (right) shaded by vaccine group (top), T cell subtypes (middle) and module 2-positivity (bottom). (13D) Histograms of the distribution of module 2 scores by vaccine group and animal. Dashed line (placed at two standard deviations above the mean score in the naive controls) indicates the threshold used to call cells as positive for the module. Percent module 2 positive are shown for each NHP.
Figure 13A:
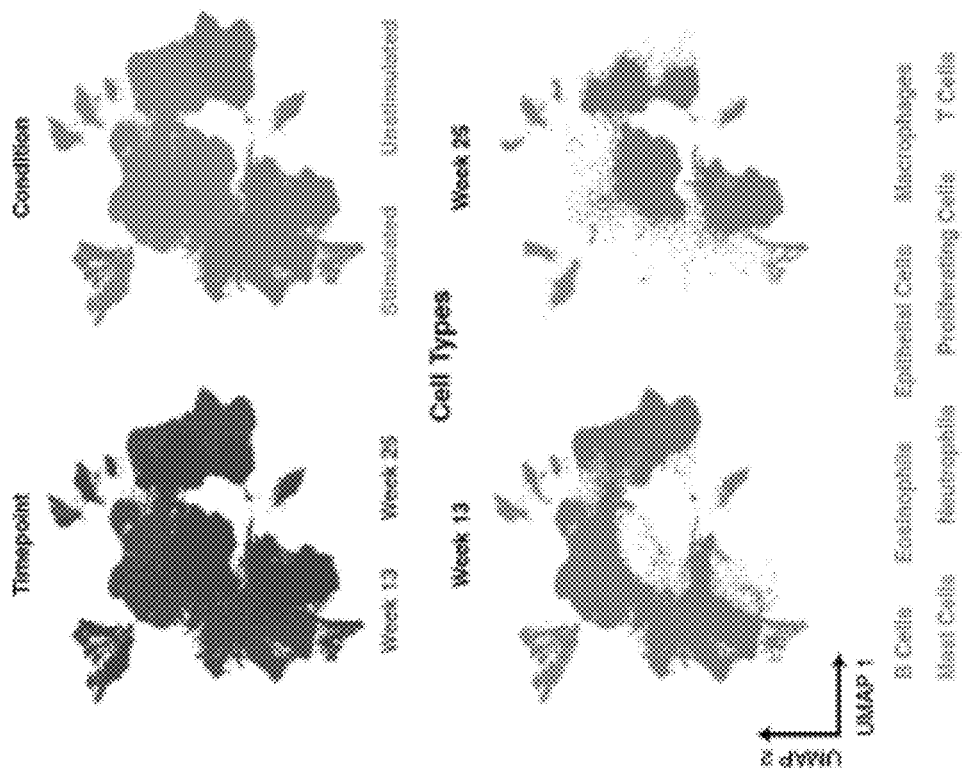
Figure 13D:
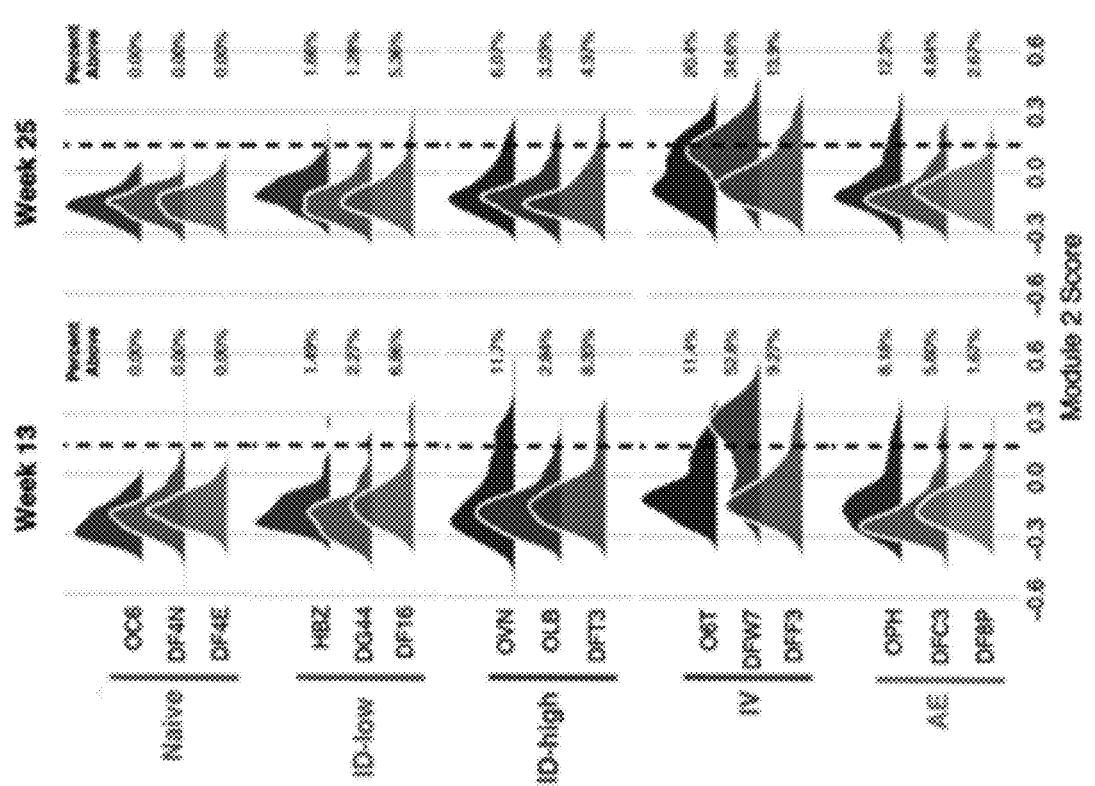
Figure 13C:
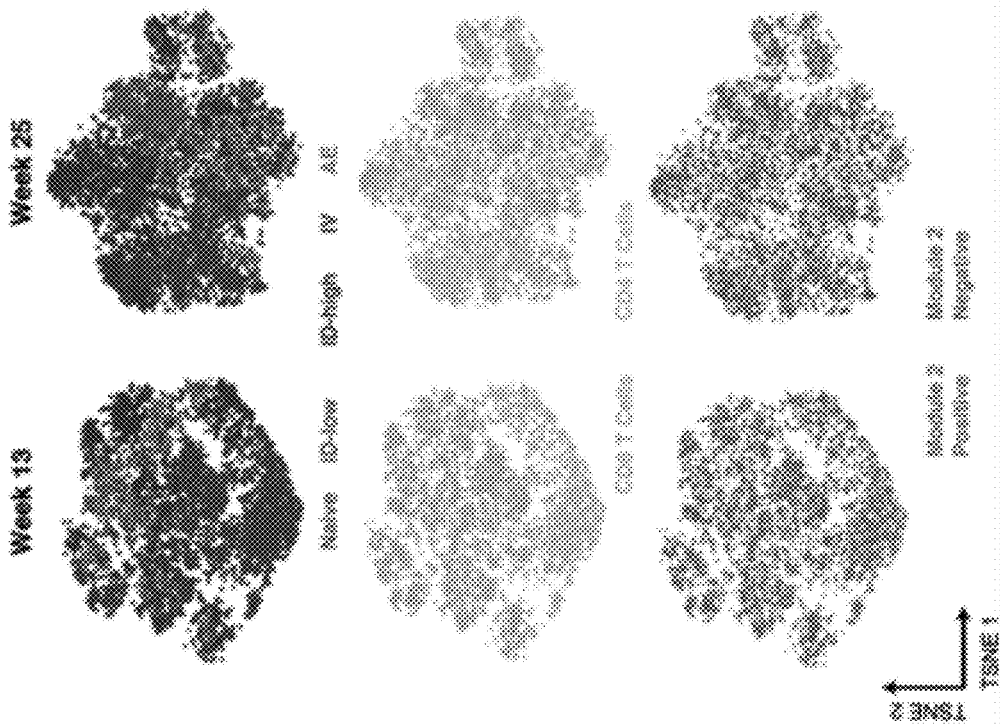
Figures 14A, 14B:
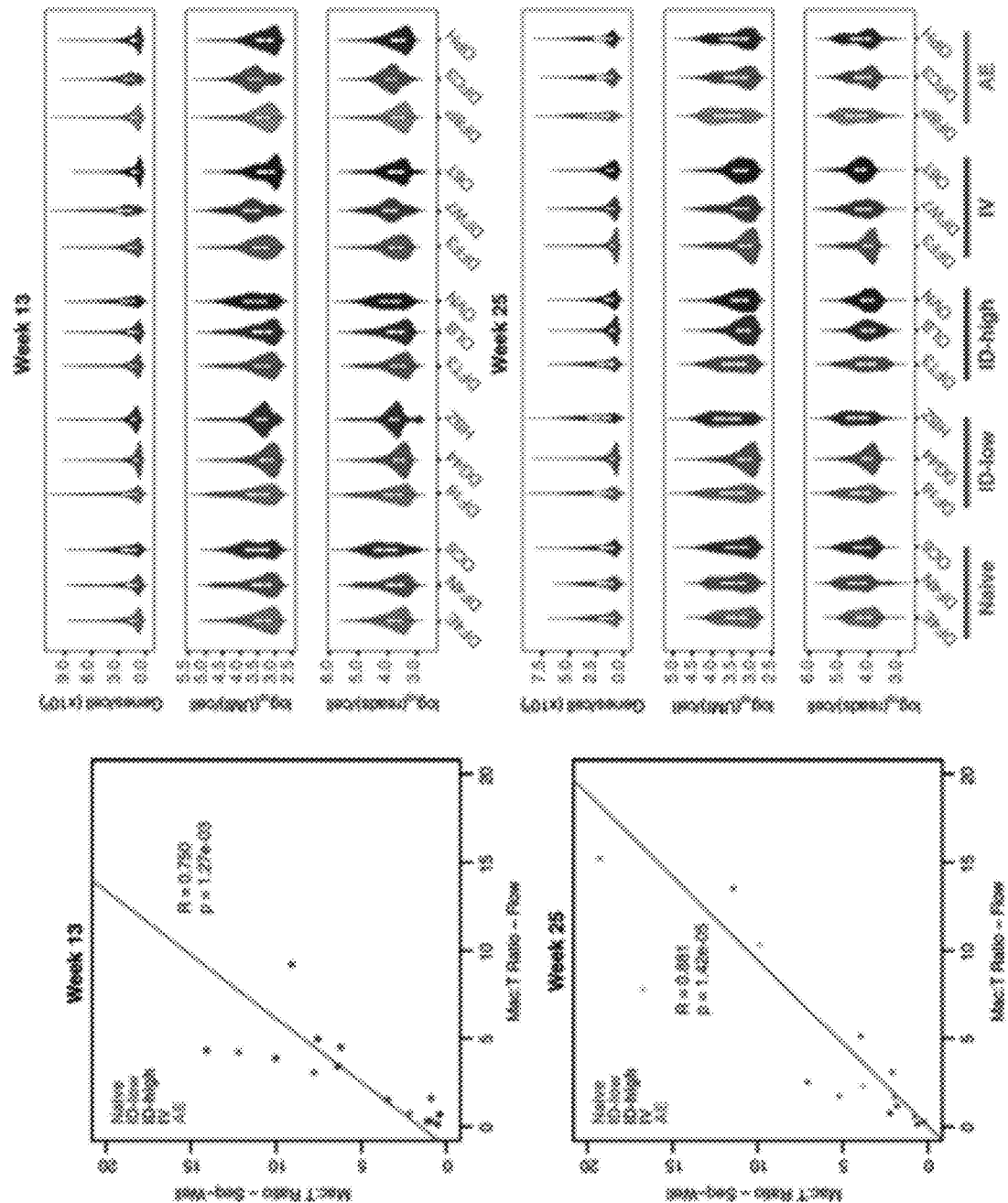
FIGS. 14A-14C—Data quality metrics for single-cell mRNA sequencing (Seq-Well). (14A) Scatterplots showing the relationship between the ratios of macrophages (Mac) to T cells (T) in BAL measured by flow cytometry and Seq-Well at week 13 (top) and week 25 (bottom) after BCG immunization. Data points are individual animals, shaded by vaccine. At both time points, a significant correlation was observed between the ratio of macrophages to T cells in BAL between flow cytometric analysis (FIG. 6A) and single-cell RNA sequencing (Week 13: R=0.75, P=1.27× 10−3; Week 24: R=0.881 P=1.42×10−5) (14B) For the Seq-Well analysis, number of genes, unique molecular identifiers (UMI), and reads per cell (unstimulated and stimulated cells combined) for each animal at weeks 13 (top) and 25 (bottom) after quality filtering (Methods). (14C) Stacked bar graphs showing the cellular composition of BAL (percent of each indicated cell type in all cells combined) for each animal in each vaccine group at weeks 13 (top) and 25 (bottom) after BCG immunization. Macrophages and T cells are depicted by M and T, respectively.
Figure 14C:
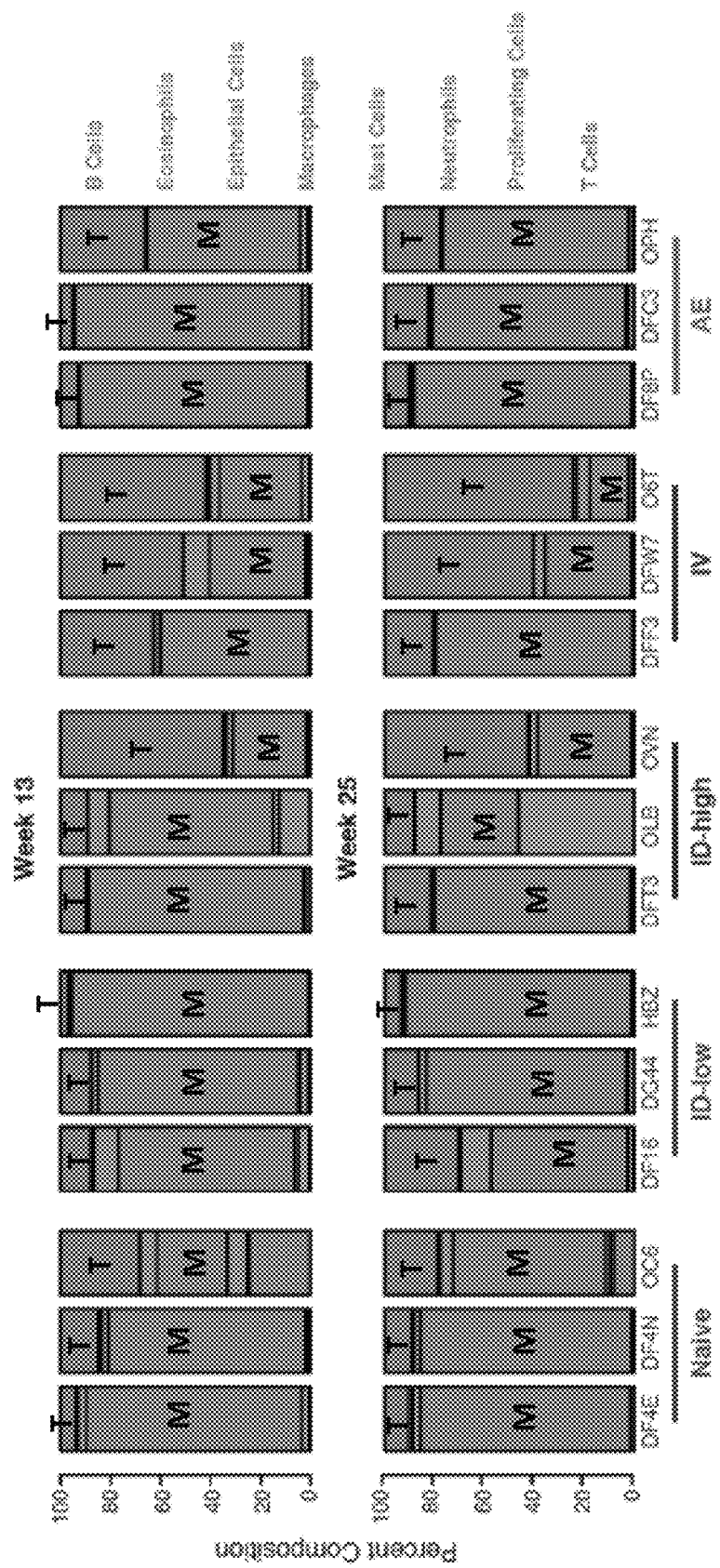

To expand the qualitative analysis of BAL T cell responses between vaccine groups with an orthogonal approach at the single cell level, Seq-Well—a high-throughput single-cell mRNA sequencing (scRNA-Seq) platform (Gierahn et al. 14:395-398 92017)) was used to comprehensively examine phenotypic and transcriptional states amongst T cells that might underlie protective vaccine responses (FIGS. 9F-9H, 13A-13D, and 14A-14C). 160,000 single-cell transcriptomes derived from unstimulated and PPD-stimulated total BAL cells from 15 NHP (3 per vaccine group, cohort 4) at week 13 (peak of BAL response) and week 25 (time of challenge) were profiled (FIG. 13A). Across all animals, the ratio of macrophages to T cells in BAL determined by scRNA-seq was well-correlated with that determined by flow cytometry (FIGS. 14A, 14C).

Correlated patterns of gene expression within unstimulated and PPD187 stimulated T cells were examined to uncover groups of genes whose coordinated activity differed by vaccine group and thus might associate with protection (FIG. 13B). A total of 7 significant stimulation-inducible T cell modules were identified at week 13 after vaccination and used to generate expression scores across all T cells at both time points after BCG immunization. A stimulation-inducible module of gene expression, module 2, was identified to be enriched for memory T cell functionality (Methods) that was primarily expressed in a population of CD4 T cells from BAL of IV BCG-immunized NHP (FIGS. 9F, 9G, and 13C, 13D). Indeed, the CD4 T cells enriched for module 2 were detected at week 13 and persisted through week 25 (FIGS. 9F, 9G, 13E, and 13D). Differential gene expression analysis was performed to compare T cells positive for module 2 to those negative for this module (FIG. 9H). This analysis showed enrichment for expression of many genes among module 2-positive T cells, some of which have been previously associated with protection against TB including IFNγ, TBX21, RORC, TNFSF8 (Sallin et al. *Nat Microbial* 3:1198-1205 (2018)) and Il-21R (Booty et al. *Scientific Rep* 6:36720 (2016)).

Figure 15A:
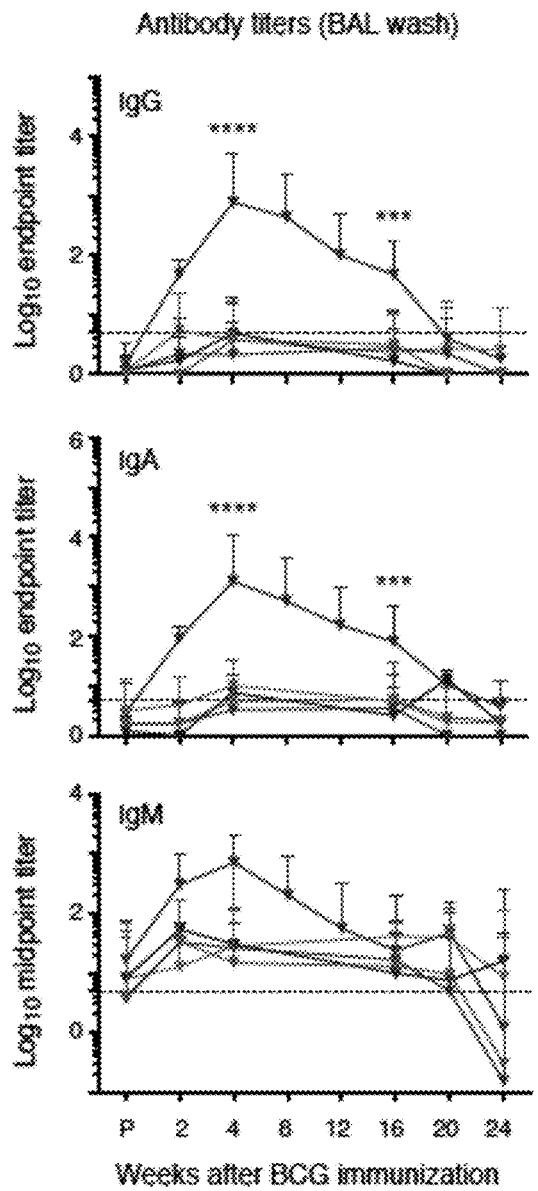
FIGS. 15A-15B—Humoral immune response in BAL and plasma after BCG immunization. Mtb whole cell lysate (WCL)-specific IgG, IgA, and IgM antibody titers were measured from individual animals (cohorts 1-4) at various time points pre-(P) and post-BCG immunization. Shown are endpoint titers for IgG and IgA and midpoint titers for IgM (where end point was not reached) (15A) Antibody titers in 10-fold concentrated BAL fluid (n=11-13 animals per group except at weeks 2, 20, and 24 where only 3 animals per group (cohort 4) were sampled). (15B) Antibody titers in plasma (n=11-13 animals per group). Shown are geometric means and standard deviations; dashed line indicates assay limit of detection. A Kruskal-Wallis test was used followed by Dunn's multiple comparison test comparing all vaccine groups to $ID_{low}$ at weeks 4, 16 and 24 (BAL) or weeks 4 and 24 (plasma). * P<0.05,  P<0.01, * P<0.001, **** P<0.0001 (color-coded by vaccine group).
Figure 15B:
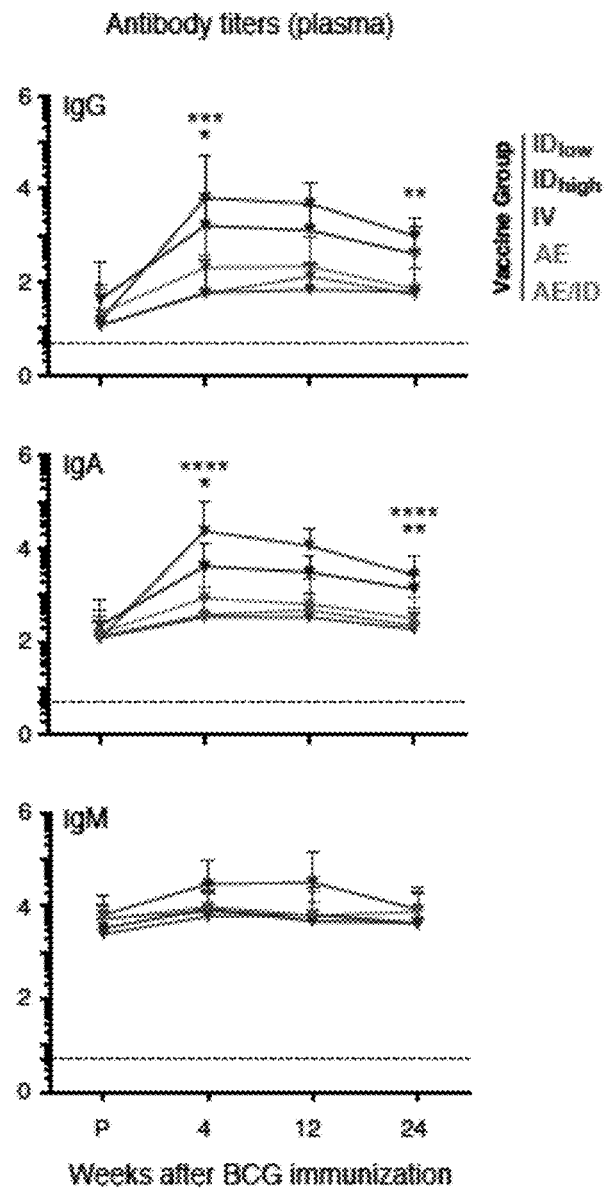

To complete the analysis of adaptive immunity, Mtb whole cell lysate (WCL)-responsive antibody responses were assessed in BAL and plasma following BCG immunization (FIGS. 15A, 15B). In concentrated BAL wash fluid, antigen-responsive IgG, IgA and IgM were detected only in IV BCG-immunized NHP, and returned to pre-vaccination levels by the time of challenge. In plasma, both $ID_{high}$ and IV BCG elicited elevated IgG and IgA antibody responses compared to $ID_{low}$ BCG.

Example 4—*M. tuberculosis* Challenge Outcome

Figure 16A:
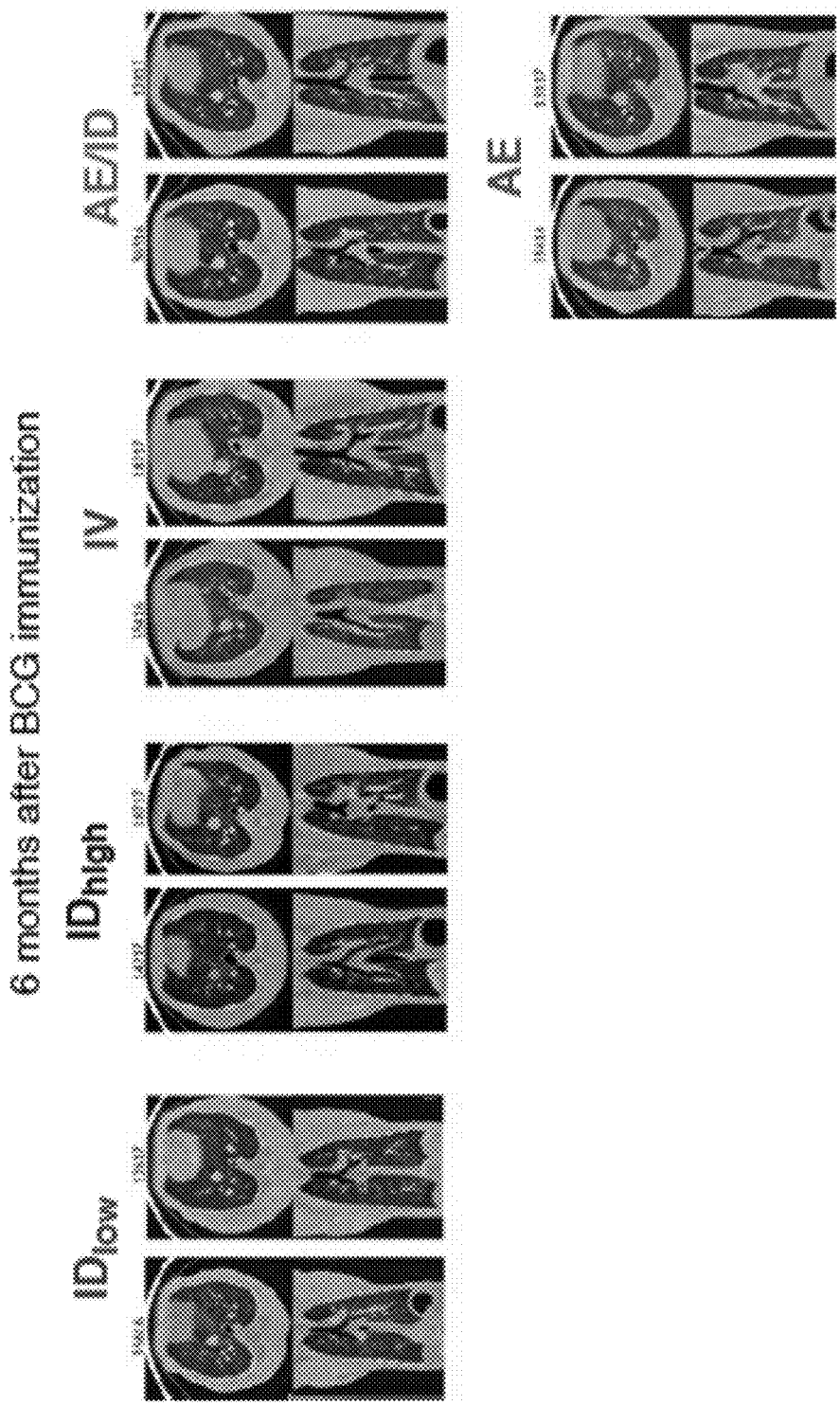
FIGS. 16A-16B—PET CT scans after BCG immunization. (16A) Axial (top) and coronal (bottom) PET CT scans of 2 representative animals from each vaccine group 6 months after BCG, prior to Mtb infection. (16B) Serial FDG PET CT scans of representative animals at 2 and 4 weeks after BCG vaccination by indicated routes; 2 animals per vaccine group. Shading indicate metabolism with brighter areas representing increased FDG retention. Scale represents SUV values. Darker arrows indicate highly metabolically active LN, white arrow indicates a highly active spleen, and "H" is written over the heart.
Figures 17A, 17B:
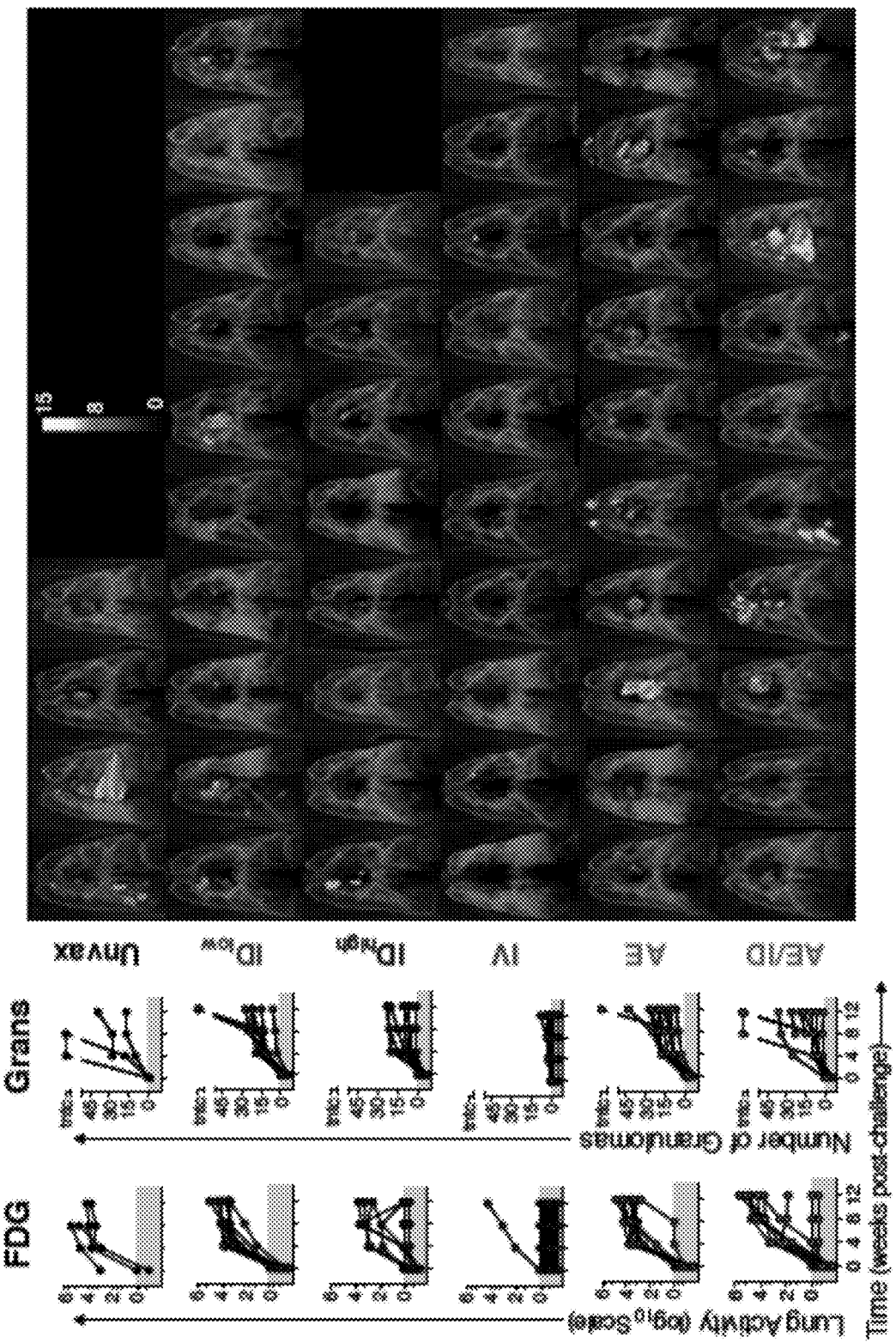
FIGS. 17A-17D—Reduced lung inflammation and granulomas in IV BCG-immunized NHP following Mtb challenge. (17A) Lung inflammation as measured by total FDG activity and number of lung granulomas (Grans) over the course of infection as measured by serial PET CT scans. Each line shows one animal over time; three animals (two unvax and one $ID_{low}$) did not meet study end point. (17B) Three-dimensional volume renderings of PET CT scans of each animal at time of necropsy; vaccine group is on left. Warm colors indicate inflammation, with brighter areas representing increased FDG retention. For these images, PET was limited to thoracic cavity; standardized uptake value (SUV) scale bar is shown in top right. (17C) Lung inflammation as measured by total FDG activity and (17D) Number of lung granulomas by PET CT scan at time of necropsy. Horizontal bars represent the median. Kruskal-Wallis tests were used and reported P values represent Dunn's multiple comparison test comparing each group to $ID_{low}$. Tntc: too numerous to count. All data points within the grey areas are zero.
Figure 17D:
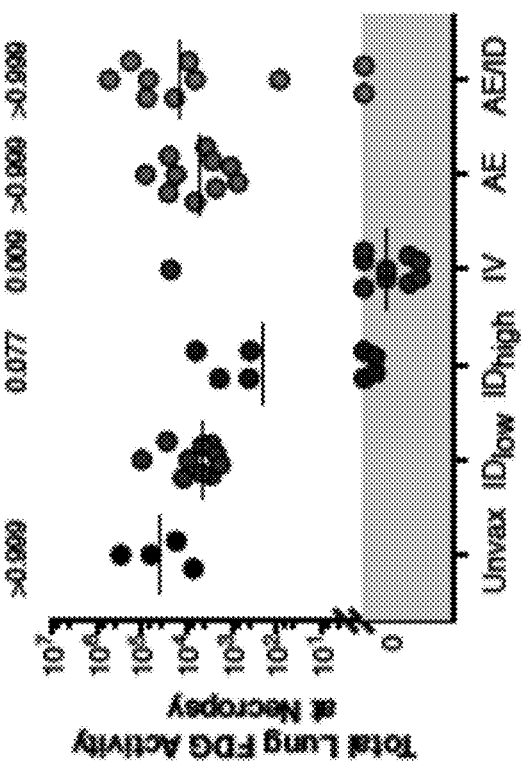
Figure 17C:
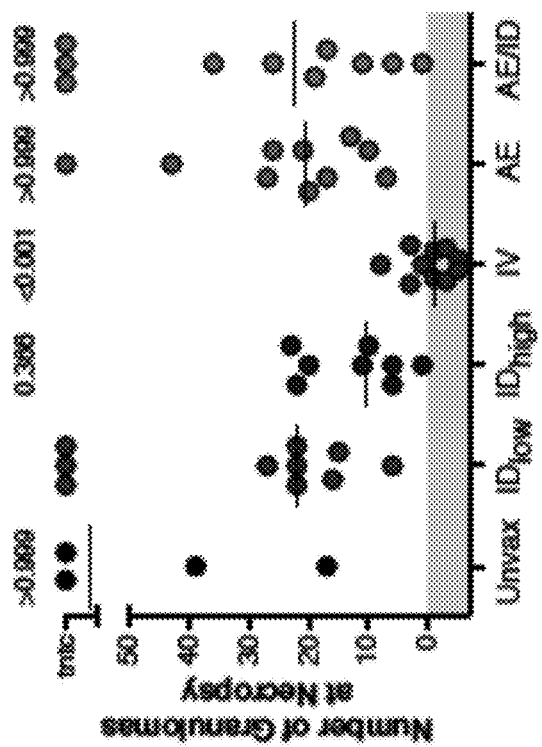

Six months after BCG immunization, animals were challenged in 3 separate cohorts with a nominal dose of 10 CFU of the highly pathogenic Mtb Erdman strain via bronchoscope, with a defined study end point of 12 weeks post-challenge (FIGS. 1B, 3A, and 3B). Infection and disease were tracked serially using $^{18}$F-fluorodeoxyglucose (FDG) positron emission tomography-computed tomography (PET CT), a sensitive and non-invasive technique to monitor disease progression in NHP (White et al. *J Vis Exp:JoVE* doi:10.3791/56375 (2017); Maiello et al. *Infect Immun* 86:doi:10.1128/iai.00505-17 (2018)). Total FDG activity in lungs, a measure of cellular metabolism that correlates with total thoracic bacterial burden after Mtb infection (Maiello et al. *Infect Immun* 86:doi:10.1128/iai.00505-17 (2018); Darrah et al. *njp Vaccines* 4 (21):doi:10.1038/s41541-019-0113-9 (2019)), was negative in all animals prior to Mtb challenge (FIG. 16A) but was elevated 4 weeks after infection in unvaccinated NHP and remained elevated throughout the study (FIG. 17A). Three-dimensional reconstructions of the PET CT scans of all Mtb-challenged NHP just prior to necropsy are shown in FIG. 3b. Two of the 4 unvaccinated NHP and 1 of the 10 $ID_{low}$ BCG-immunized NHP reached the humane end point and were necropsied prior to 12 weeks post-challenge. All $ID_{low}$ BCG-immunized animals had elevated FDG activity in lungs over 12 weeks. In the AE group, 9 of 10 NHP showed elevated FDG activity throughout infection, with the tenth animal having high FDG activity by 12 weeks post-infection. Two NHP in the AE/ID group showed no FDG activity in lungs up to 12 weeks. Interestingly, 2 of the 8 NHP in the $ID_{high}$ BCG vaccine group had no FDG activity throughout the infection, and 2 showed increased inflammation that returned to baseline by 12 weeks post-infection, suggesting partial albeit not significant protection. In striking contrast to all other vaccine groups, 9 of 10 NHP in the IV BCG group had no FDG activity in the lungs throughout the 12-week challenge phase (Fisher's exact $P<10^{-4}$ compared to $ID^{low}$ BCG; FIGS. 17A-17C).

PET CT was also used to track granuloma formation. It was previously shown that each granuloma is initiated by a single Mtb *bacillus* (Lin et al. *Nat Med* 20:75-79 (2014)) and thus quantifying granulomas provides a useful measure of infection establishment and early dissemination. Increasing numbers of granulomas is correlated with development of active TB (Maiello et al. *Infect Immun* 86:doi:10.1128/iai.00505-17 (2018)). By 4 weeks post-infection there was a wide range of numbers of granulomas in unvaccinated NHP and granulomas were observed in all animals in the $ID_{low}$, $ID_{high}$, AE, and AE/ID BCG groups (FIG. 17A). In contrast, IV BCG-immunized NHP had fewer granulomas compared to $ID_{low}$ BCG (P<0.001), and 6 of 10 IV BCG-immunized animals had no detectable granulomas throughout infection (FIGS. 17A, 17B, 17D).

Detailed necropsies were performed on all animals at the study end point, 12 weeks after infection (FIGS. 18A-18F). IV BCG-immunized NHP had lower gross pathology scores (Maiello et al. *Infect Immun* 86:doi:10.1128/iai.00505-17 (2018)) compared to $ID_{low}$ BCG (P=0.002), while the median of the scores from the other groups were similar to $ID_{low}$ BCG (FIG. 18A). The extrapulmonary disease score accounts for the presence of Mtb-related pathology and growth from sites outside the thoracic cavity (Maiello et al. *Infect Immun* 86:doi:10.1128/iai.00505-17 (2018)). There was no extrapulmonary disease in any of the IV BCG vaccinated animals, whereas the other groups had variable extrapulmonary involvement (FIG. 18B).

The primary measure of vaccine-elicited protection was bacterial burden at necropsy. All granulomas and other lung pathologies, all thoracic lymph nodes (LN), and peripheral LN were matched to the final PET CT scan and harvested for quantification of Mtb. In addition, random sampling of uninvolved lung equaling 50% of each of the 7 lung lobes, 3-5 granulomas (if present) from spleen and liver, ~30% of uninvolved spleen and liver, and any additional pathologies were processed for bacterial burden. Collectively, this analysis provides a comprehensive measure of bacterial burden (Maiello et al. *Infect Immun* 86:doi:10.1128/iai.00505-17 (2018)). The median total thoracic bacterial burden (CFU) for $ID_{low}$ BCG (5.1+1.3 IQR $\log_{10}$) was only slightly lower than that of the unvaccinated NHP (5.9+1.0 IQR $\log_{10}$), consistent with $ID_{low}$ BCG having minimal protective effect in this susceptible rhesus macaque model (FIG. 18C). In striking contrast, the median total thoracic CFU in IV BCG-immunized NHP was 0+1.2 IQR $\log_{10}$—a 100,000-fold reduction compared to $ID_{low}$ BCG (P=0.006). Remarkably, 6 of the 10 IV BCG-immunized animals had no detectable Mtb in any tissue measured, while another 3 animals had <45 total CFU, all contained within a single granuloma in each animal. Only 1 of the IV BCG NHP was not protected and had CFU similar to $ID_{low}$ BCG-vaccinated animals (FIG. 18C). The $ID_{high}$, AE and AE/ID groups had similar median bacterial burdens compared to $ID_{low}$ BCG, indicating no protection by this outcome measure. The total thoracic bacterial burden can be separated into lung (FIG. 18D) and thoracic lymph node (FIG. 18E) CFU. Only the IV BCG group was lower compared to the benchmark $ID_{low}$ BCG (lung, P=0.006; LN, P=0.001). Nine of the 10 IV BCG-immunized animals had no LN that were positive for Mtb (FIG. 18E).

Protection can be defined as having fewer than a given number of total thoracic Mtb CFU. By this criterion, protection was highly significant (Fisher's exact $P<10^{-4}$) at any given threshold less than 10,000 CFU (FIG. 18F). Notably, the IV BCG group showed 90% protection (95% CI: 60-98%) at a threshold as low as 50 CFU. Thus, BCG IV confers an unprecedented degree of protection in a stringent NHP model of TB disease.

Example 5—Immune Responses after Mtb Challenge

Figure 18G:
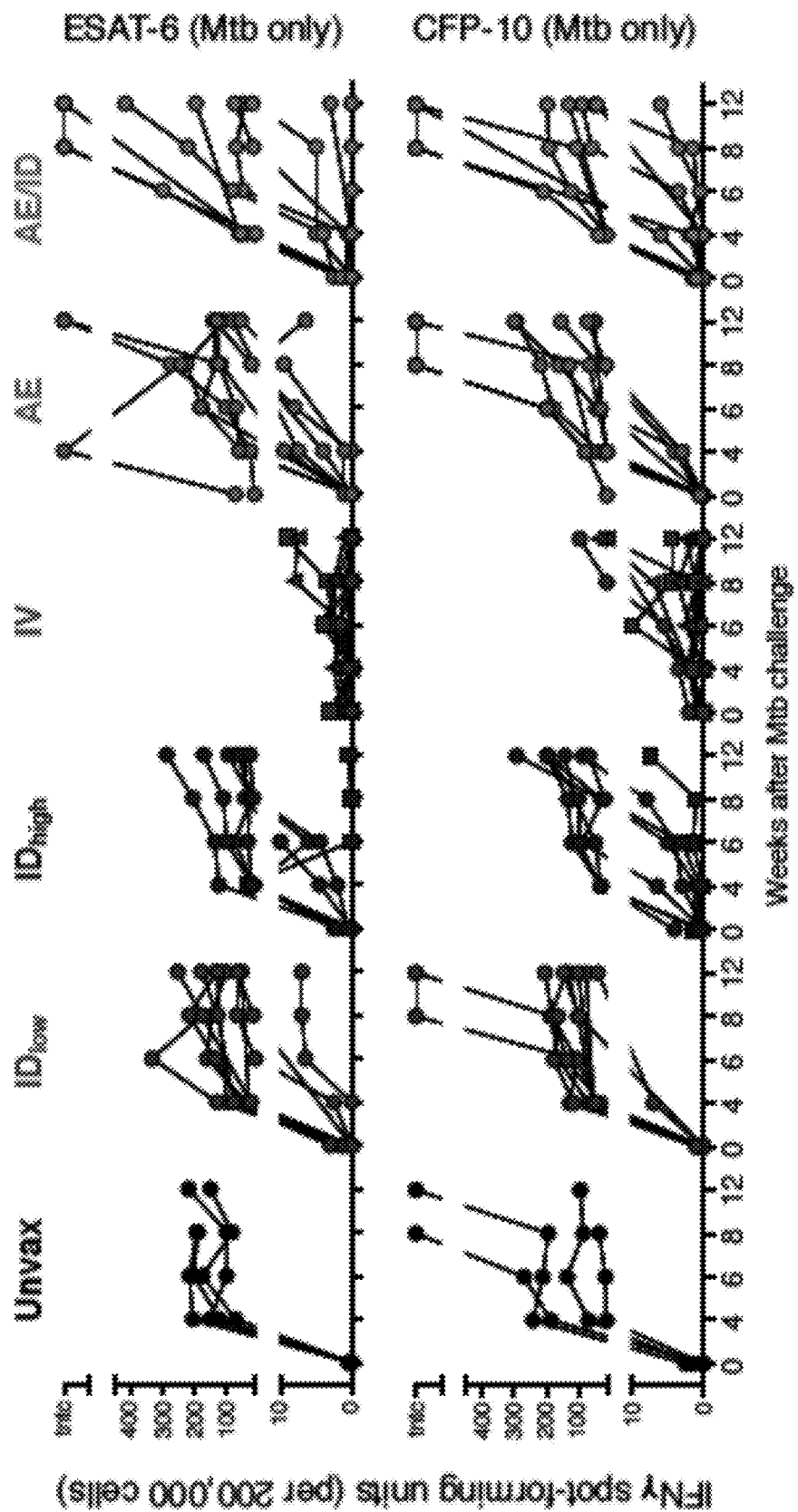
Figure 19A:
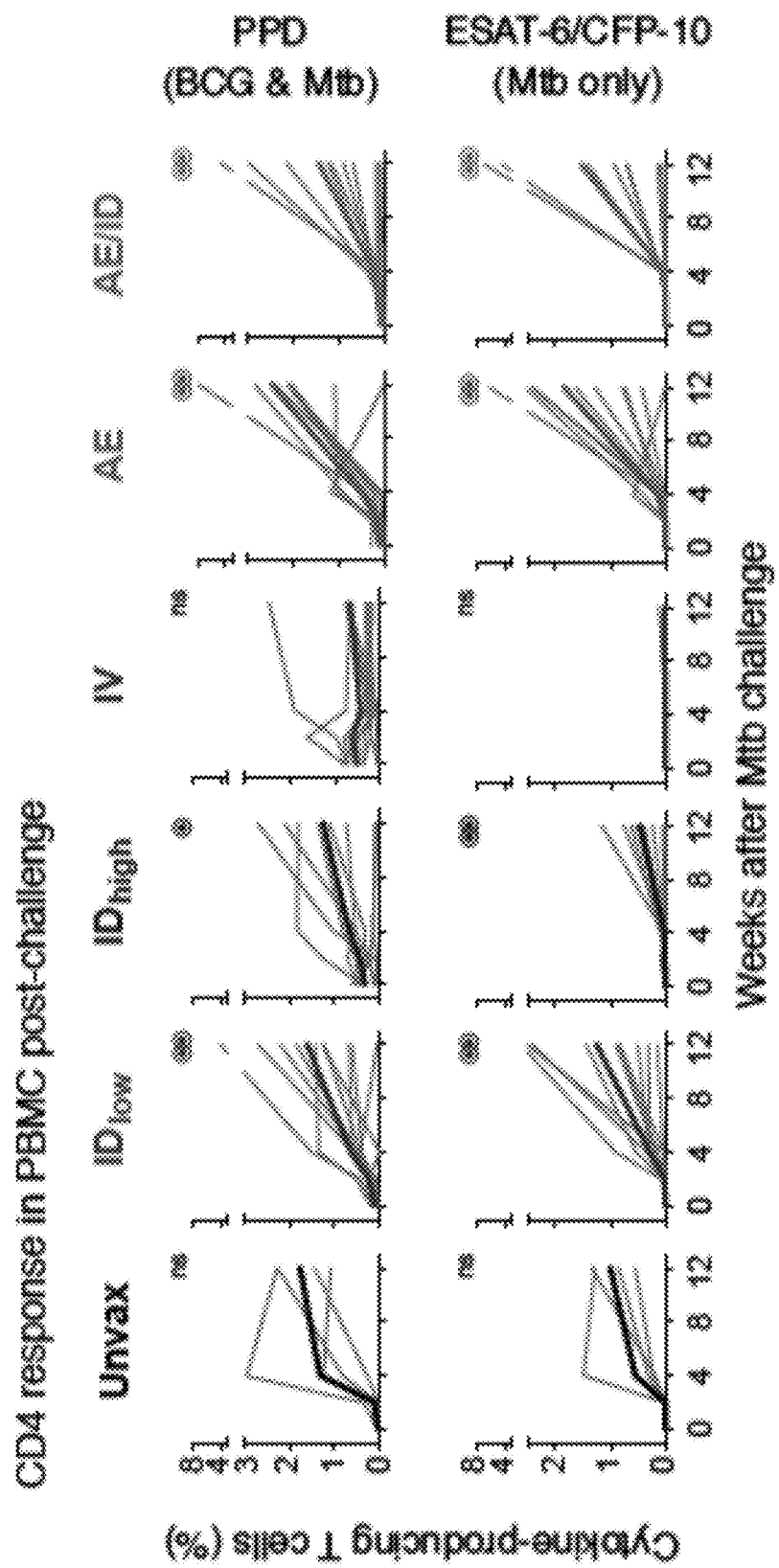

In vaccine efficacy studies, measuring immune responses after challenge provides data as to whether vaccine-elicited responses are boosted (anamnestic), and if primary (de novo) responses are generated to the infectious challenge. In this regard, measurement of T cell responses against ESAT-6 and CFP-10, proteins expressed in Mtb but not BCG, can be used to specifically detect primary Mtb infection, even in BCG-immunized animals. Peripheral T cell responses to these Mtb-specific antigens, as well as antigens expressed by both BCG and Mtb (e.g., PPD), were assessed by IFNγ ELISpot and flow cytometry after Mtb challenge (FIGS. 18G, 19A, and 19B). After infection, the majority of animals in AE or ID vaccine groups developed CFP-10 or ESAT-6 ELISpot responses, reflecting a primary response to Mtb. In striking contrast, ESAT-6 and CFP-10 ELISpot responses in the IV BCG group were lower at every time point after Mtb challenge compared to the $ID_{low}$ group (FIG. 18G). Similar results were obtained using flow cytometry to individually assess cytokine-producing CD4 and CD8 T cell responses (IFNγ, IL-2, TNF, or IL-17) to PPD or ESAT-6/CFP-10 from PBMC after infection (FIGS. 19A, 19B).

Antibody responses to Mtb antigens were also assessed post-challenge. Similar to the cell data, there were no anamnestic antibody responses in the plasma of IV BCG-immunized NHP following Mtb infection, although IgG and IgA responses increased in ID$_{low}$, AE, and AE/ID BCG-immunized NHP as well as in unvaccinated, infected animals (FIG. 19C). Taken together, these immune data suggest that in the majority of IV BCG-vaccinated NHP, there is rapid elimination of Mtb upon challenge that restricts the generation of detectable primary or anamnestic adaptive responses to Mtb.

Example 6—Detection of BCG and Immune Responses in Tissues after Immunization

Figure 16B:
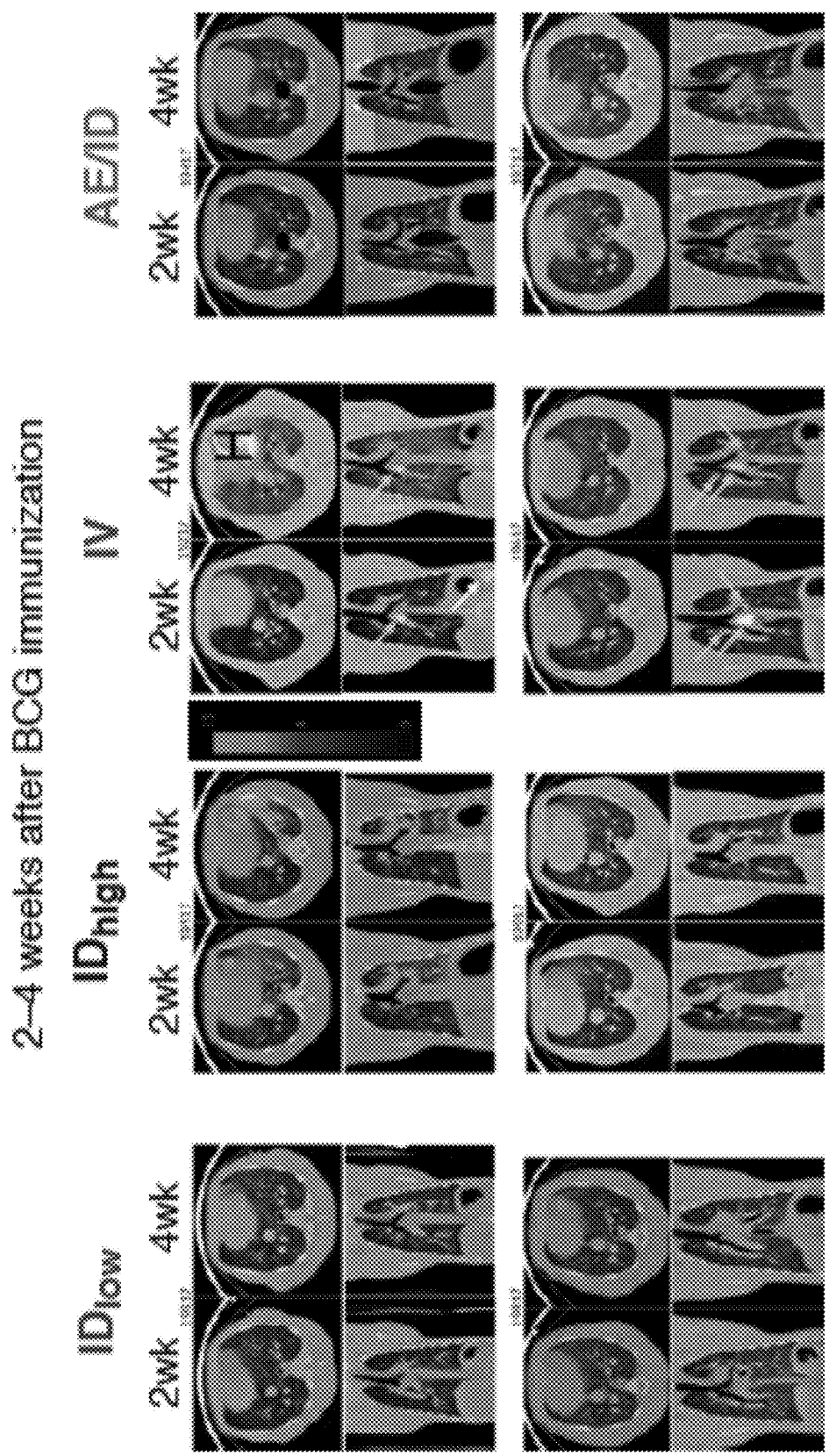

Based on the striking level of protection conferred by IV BCG compared to the other vaccine routes, Applicants expanded the analyses to assess cellular immune responses in all tissues to provide insight into the potential mechanisms of protection and sites of T cell priming. As BCG is a live, attenuated vaccine, the route of delivery might alter the tissue distribution of BCG which could influence the priming of T cell responses in such sites (Olsen et al. *Scand J Immunol* 60:273-277 (2004). To assess this, NHP were euthanized 1 month after BCG vaccination to quantify BCG CFU (FIG. 20A) and assess CD4 and CD8 T cell responses in primary and secondary lymphoid organs, peripheral and lung LN and lung parenchyma (FIGS. 20B, 20C). BCG was detected at the skin site(s) of injection and draining axillary LN in many of the ID BCG-vaccinated NHP, but not in the lung lobes (FIG. 20A). In AE or AE/ID BCG-vaccinated animals, BCG was detected primarily in the lung lobes and BAL. In striking contrast, BCG was detected in the spleen of all 4 IV BCG-vaccinated NHP, as well as in the lung lobes, BAL and in various peripheral and lung LN. Indeed, PET CT scans at 2 and 4 weeks after BCG vaccination showed increased metabolism (FDG uptake) localized to the lung LN, lung lobes and spleen elicited by the IV but not other routes (FIG. 16B).

To determine how the tissue distribution of BCG corresponded with the detection of T cell responses at the same site, antigen-responsive CD4 and CD8 T cells were quantified (FIG. 20B, 20C). In IV BCG-immunized NHP, CD4 responses were significantly increased in the spleen and lung compared to ID$_{low}$-immunized NHP, consistent with the contemporaneous localization of BCG. Moreover, CD4 T cell responses were observed in systemic sites such as PBMC, bone marrow and peripheral LN. CD8 responses were largely confined to the lung lobes and spleen after IV BCG. Following ID$_{high}$ BCG, CD4 T cell responses were detected in spleen, bone marrow and axillary LN draining the sites of immunization, but were limited in lung lobes and lung LN. AE or AE/ID immunized animals had detectable CD4 responses confined to the lung and BAL. These data indicate compartmentalization of BCG detection and T cell immunity by the route of vaccination, highlighting the systemic distribution of immune responses after IV BCG versus the more limited and localized responses following the ID and AE routes.

Figure 5A:
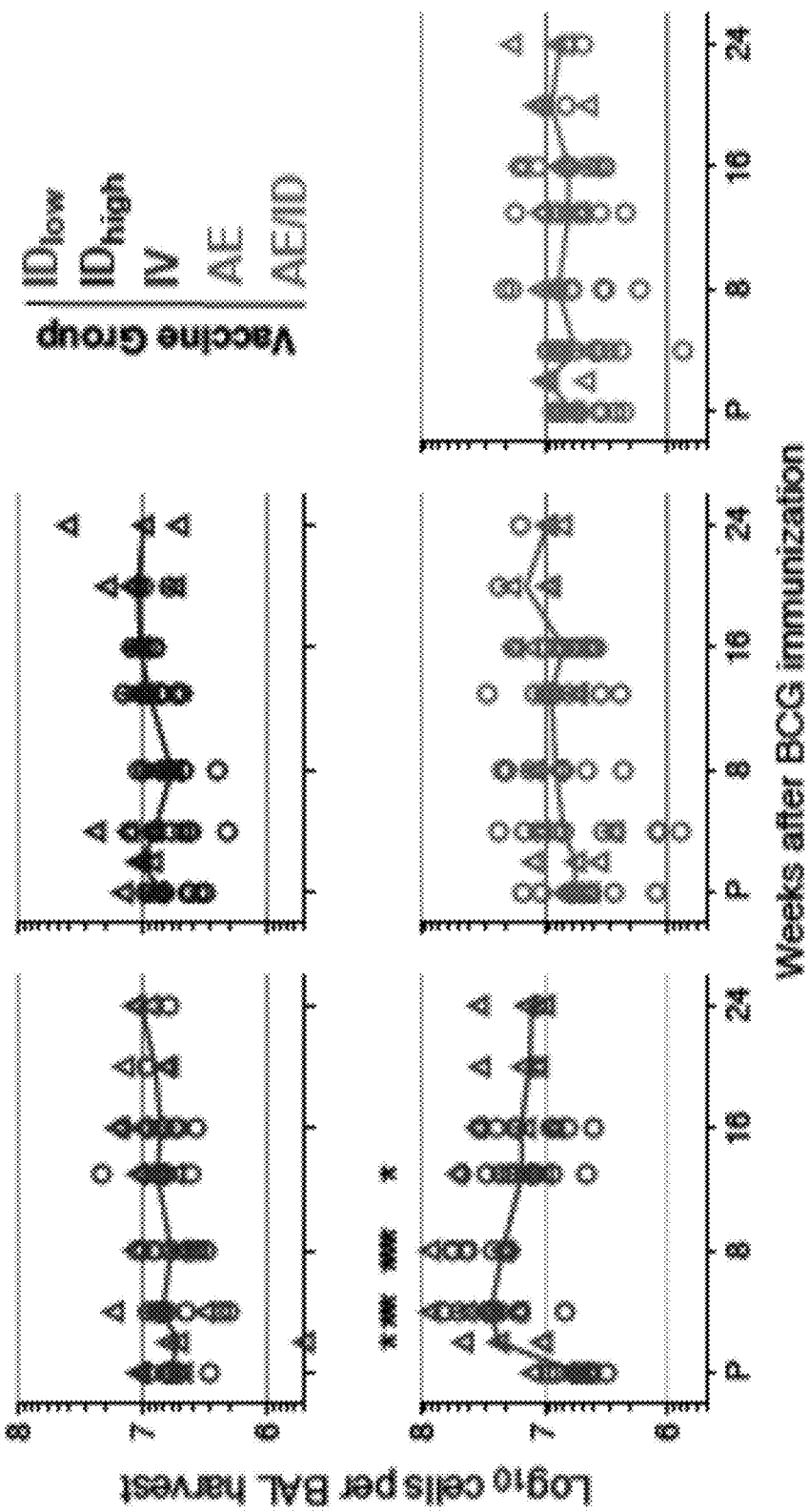
FIGS. 5A-5B—Cell counts in the BAL after BCG immunization. (5A) Total number of viable, nucleated cells isolated from the BAL harvests of BCG-immunized NHP (cohorts 1-4) at multiple time points pre-vaccination (P) and post-BCG, as determined by ethidium bromide/acridine dual-fluorescence automated counting. Circles represent individual animals from challenge cohorts (1-3) that were not lavaged after week 16 (per protocol); triangles are animals from cohort 4 that were used for immunological measurements only and sampled through week 24 after BCG. Line represents the median for each group over time. (5B) Number of cells of indicated leukocyte population in the BAL of BCG-immunized NHP 8 weeks after immunization, as determined by flow cytometry (identified as in FIG. 26). For each subset, the frequency of live cells was multiplied by the number of viable nucleated cells harvested from the BAL. Data points are individual animals and horizontal lines represent the geometric means that were used to generate FIG. 1C. T, T cells; B, B cells; mDC, myeloid dendritic cells; pDC, plasmacytoid dendritic cells; Neut, neutrophils; NK, NK cells; CD4, CD4 T cells; CD8, CD8 T cells; Vγ9+, Vγ9+ gamma delta T cells; MAIT, mucosal associated invariant T cells; iNKT, invariant natural killer T cells. Kruskal-Wallis tests were run and reported P values represent Dunn's multiple comparison test comparing each vaccine group to $ID_{low}$. * P<0.05,  P<0.01, * P<0.001, **** P<0.0001.
Figure 5B:
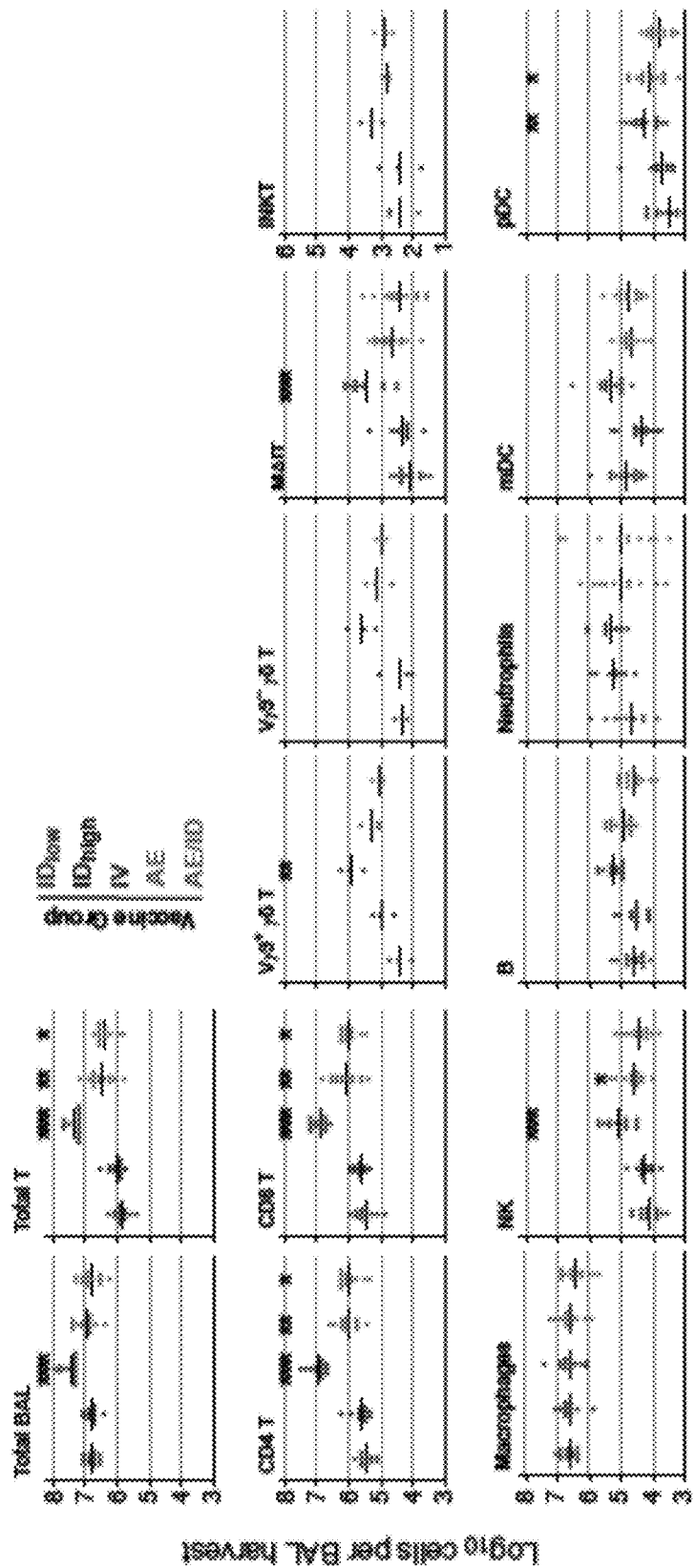
Figures 6A, 6B:
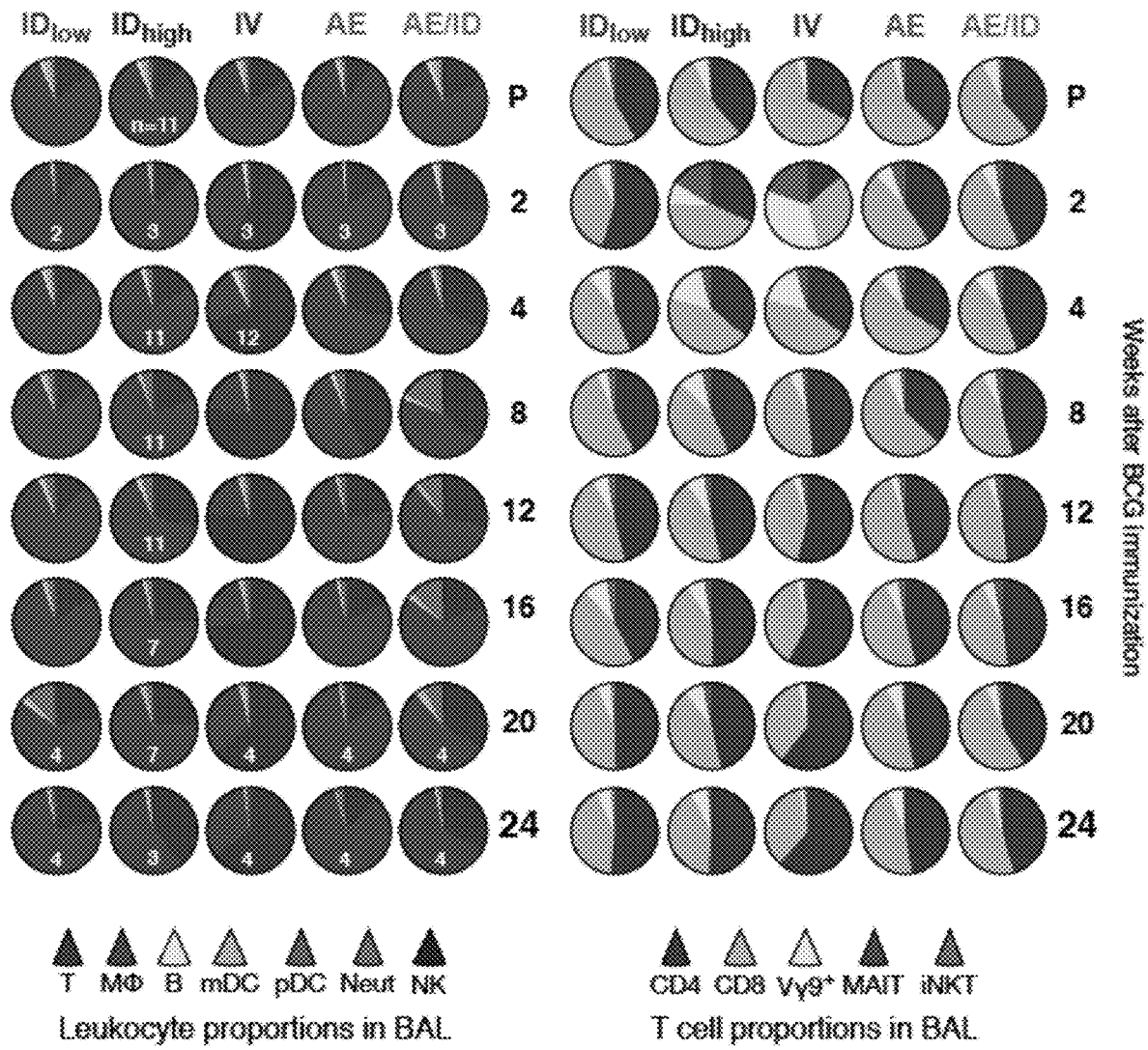
FIGS. 6A-6B—Proportions of leukocyte and T cell subsets in BAL after BCG immunization. Pie charts comprising proportions of indicated leukocytes (6A) or CD3+ T cell subsets (6B) in BAL for each vaccine group from pre-(P) to 24 weeks post-BCG immunization, as in FIGS. 1D, 1E. Cells were identified using multi-parameter flow cytometry as described in Methods and in FIG. 26. Pie graphs represent the average proportions from 13 animals per vaccine group except where indicated (white numbers, leukocyte pie graphs; number of animals in T cell graphs is the same). T, T cells; Mf, macrophages; B, B cells; mDC, myeloid dendritic cells; pDC, plasmacytoid dendritic cells; Neut, neutrophils; NK, NK cells; CD4, CD4 T cells; CD8, CD8 T cells; Vγ9+, Vγ9+ gamma delta T cells; MAIT, mucosal associated invariant T cells; iNKT, invariant natural killer T cells.
Figure 20E:
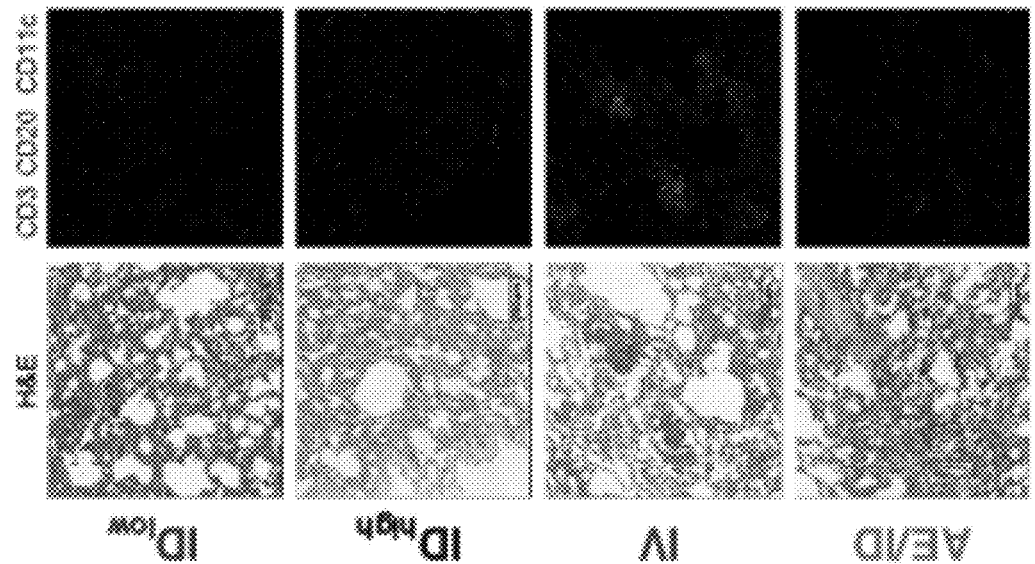
Figure 20D:
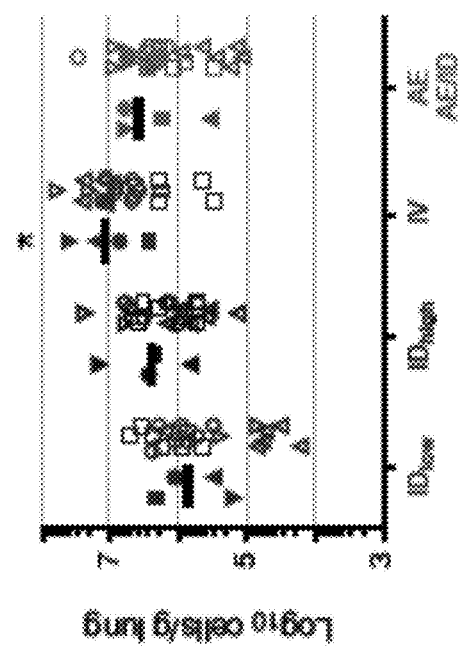
Figure 20F:
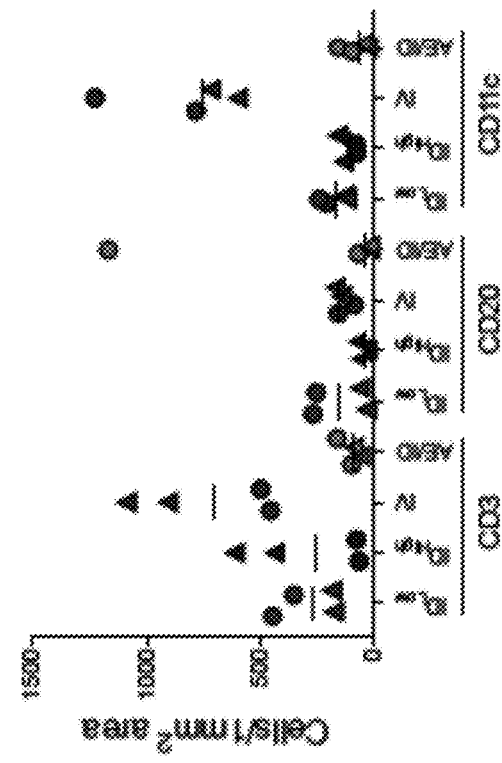
Figure 21E:
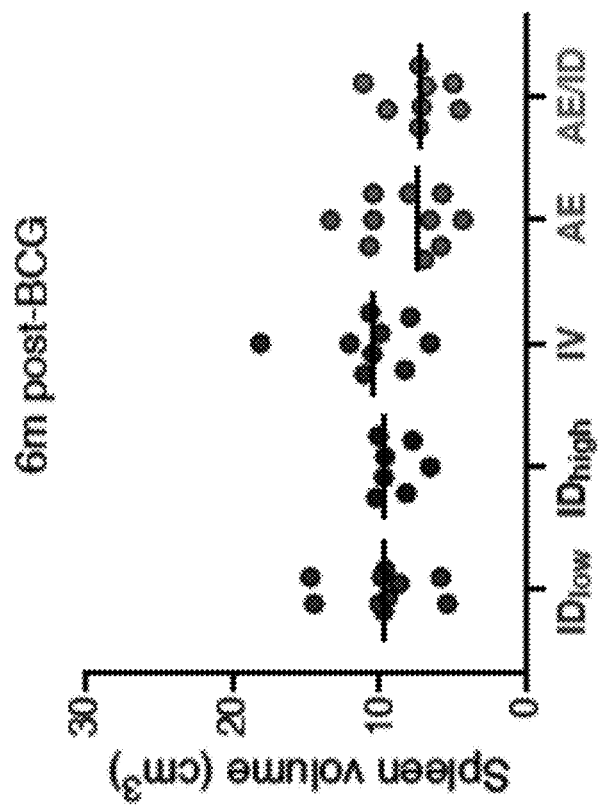
Figure 21D:
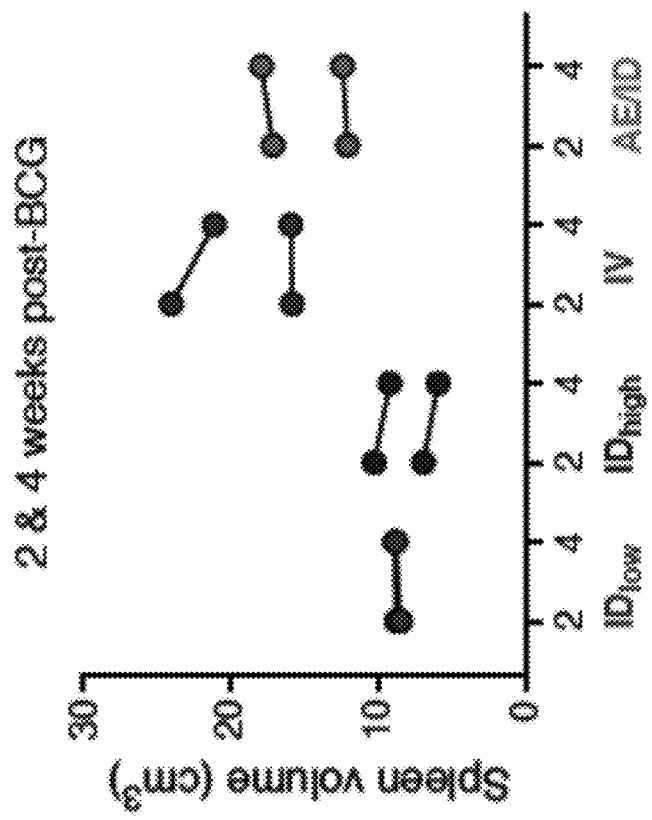

Upon examination of the lungs at necropsy, cell counts from lung tissue were increased in IV BCG animals compared to ID$_{low}$ (FIG. 20D), consistent with the BAL cell counts at the same time point (FIG. 5A). Immunofluorescence staining of lung tissue revealed elevated numbers of CD3+ T cells and CD11c+ macrophages or dendritic cells at 1-month post-BCG, which clustered into "microgranulomas" in animals that received IV BCG but not by other routes (FIGS. 20E, 20F). These clusters are histologically distinct from bronchus-associated lymphoid tissue (BALT). BALT has been associated with protection in NHP after AE delivery of an attenuated Mtb vaccine (Kaushal et al. *Nat Commun* 6:8533 (2015)) although here, BALT was observed sporadically in lung tissue sections from all vaccinated animals. Of note, thoracic LN of the IV BCG animals were enlarged (P=0.001 compared to ID$_{low}$ BCG) (FIG. 21A); similar changes were not observed in other groups. Histologic assessment of lung tissue and thoracic LN revealed non-necrotizing granulomas to a greater extent in IV BCG animals than the other groups, and lymphoid follicular hyperplasia, often with active germinal centers, only in the IV BCG group (FIGS. 21B, 21C). Spleen volume was also measured by CT scan after BCG administration (FIGS. 21D, 21E). At 2 and 4 weeks after vaccination, animals given IV BCG had ~2-fold larger spleens than those given ID BCG, with AE/ID BCG animals also displaying modestly enlarged spleens (FIG. 21D).

A similar analysis of tissue T cell responses, lung cell counts, immunohistochemistry, and PET CT scans was performed 6 months after BCG vaccination. IV BCG-immunized NHP maintained increased frequencies of antigen-responsive T cells in the spleen, BAL and lung lobes (FIGS. 22A, 22B); however, the increased numbers of total cells, T cells, and macrophages/dendritic cells observed at 1 month were not detected at 6 months post-BCG (FIGS. 22C-22E). Moreover, there were no remaining histopathological differences or detectable FDG uptake by PET CT in lung tissue in any vaccine group (FIGS. 22D and 16A), and no differences in spleen volume across vaccine groups (FIG. 21E). Spleens at 6 months after BCG vaccination were similar in size to those of ID BCG animals at 4 weeks after BCG. While the BCG burden was not assessed in animals at this time point, no CFU (BCG or Mtb) were detected in the majority of IV BCG-immunized, Mtb-challenged animals 9 months after vaccination (FIG. 18C). As an immunologic indicator of BCG persistence in vivo, the expression of Ki-67, a marker of cell proliferation, in PBMC over the course of immunization was determined. In IV BCG-immunized NHP, >60% of antigen-responsive CD4 T cells in blood were Ki-67+ at 2 and 4 weeks after BCG, but were at baseline 6 months later (FIGS. 10G-10J). Collectively, these data suggest that BCG is cleared between 1 and 9 months following IV vaccination.

Example 7—Detection of T Cells in Lung Tissue after BCG Vaccination

Figures 23A, 23B, 23C:
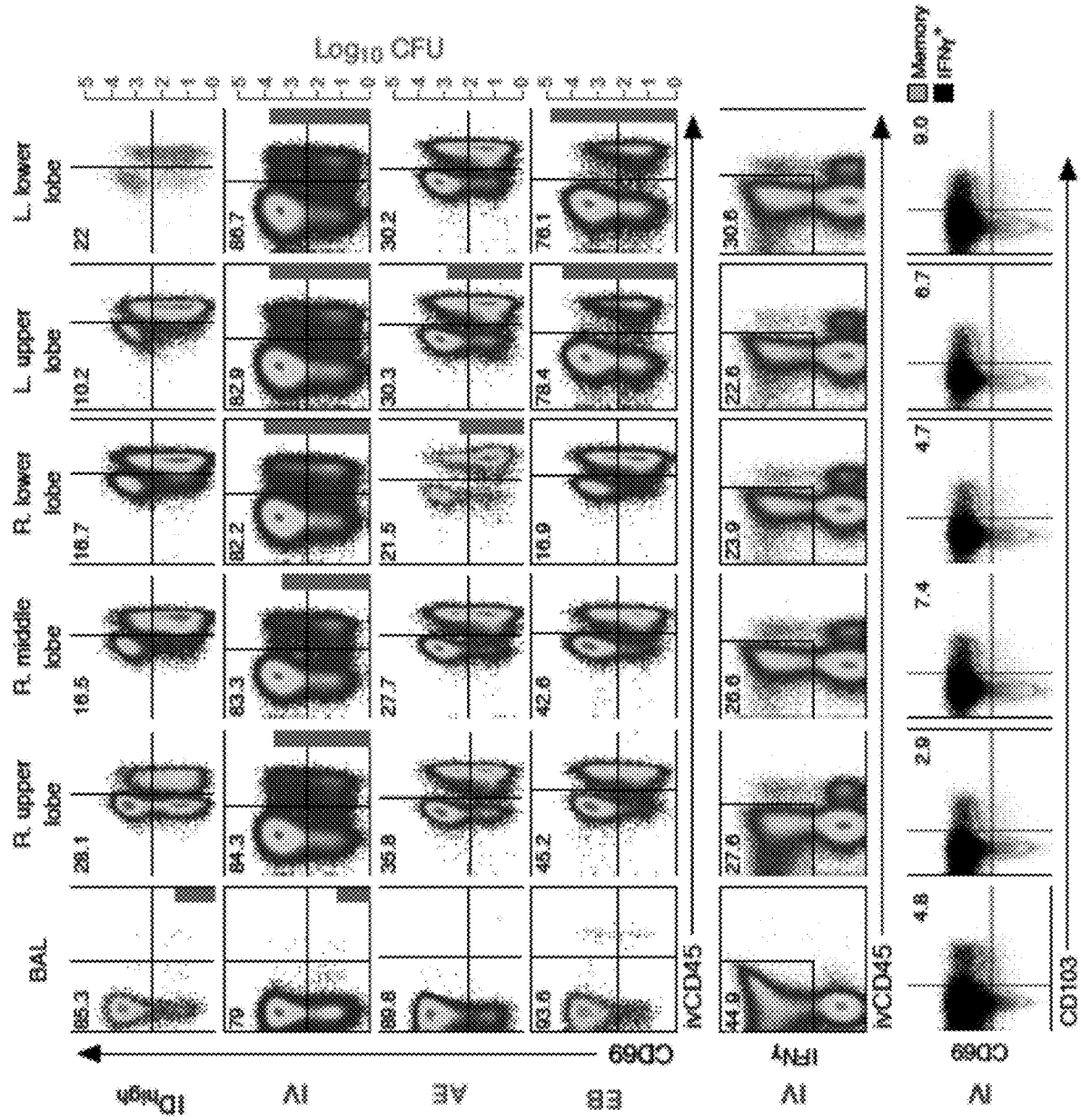
FIGS. 23A-23D—Detection of CD4 T cells in lung tissue and correlates of protection following IV BCG. (23A) To delineate tissue-versus blood-derived T cells in the lung 1 month after BCG vaccination, immunized NHP were injected intravenously prior to euthanasia with a fluorochrome-conjugated anti-CD45 antibody (ivCD45), labelling all leukocytes in the vasculature. Vaccine conditions included 5×10⁷ CFU of BCG administered ID, IV or AE, or instilled endobronchially (EB) into the left lung lobes (cohort 6, FIG. 3A). At necropsy, each tissue was plated for BCG CFU quantification. Cells isolated from BAL and each lung lobe were stained immediately ex vivo for surface marker expression or stimulated with Mtb WCL and stained for intracellular cytokine expression, and then analyzed by flow cytometry. Shown are plots of CD4 T cells derived from the BAL and individual lung lobes from one animal in each vaccine group. The percent of ivCD45− CD4 T cells expressing the tissue-residency/activation marker CD69 is shown for each animal; BCG CFU (if detected) are indicated by a bar on plot (scale on far right). (23B) The percent of WCL-responsive (IFNγ+) CD4 T cells in the lung tissue (ivCD45−) following IV BCG. (23C) IFNγ production (dark shading) as identified in (23B) is overlaid on total CD4 memory T cells (light shading); percentages indicate the proportion of IFNγ+ T cells expressing CD69 and CD103. (23D) Relationships between peak T cell responses in BAL or PBMC and total CFU at necropsy. Linear regressions of CD4 and CD8 T cell counts in BAL (left) and CD4 and CD8 T cell frequencies in PBMC (right) on total CFU. Each dot represents an individual animal; lines represent linear fit for each vaccine route. Dotted lines represent linear fit for all vaccine routes combined (with 95% confidence interval shaded).
Figure 24A:
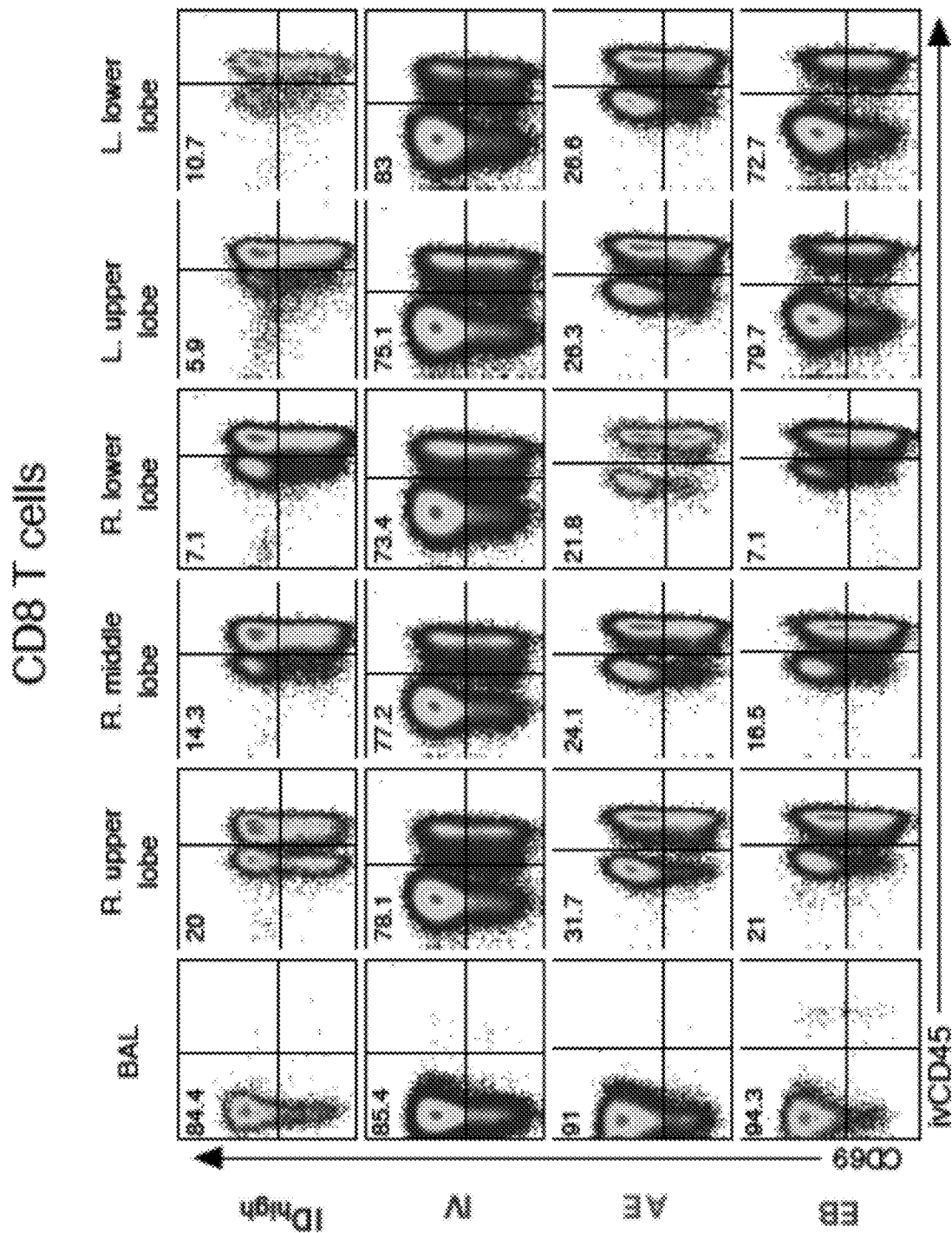
FIGS. 24A-24C—Detection of CD8 T cells in lung tissue following IV BCG. (24A) To delineate tissue-versus blood-derived T cells in the lung 1 month after BCG vaccination, immunized NHP were injected intravenously prior to euthanasia with a fluorochrome-conjugated anti-CD45 antibody (ivCD45), labelling all leukocytes in the vasculature. Vaccine conditions included 5×10⁷ CFU of BCG administered ID, IV or AE, or instilled endobronchially (EB) into the left lung lobes (cohort 6, FIG. 3A). Cells isolated from BAL and each lung lobe were stained ex vivo for surface marker expression or stimulated with Mtb WCL and stained for intracellular cytokine expression, and then analyzed by flow cytometry. Shown are plots of CD8 T cells derived from the BAL and individual lung lobes from the same animal in each vaccine group as in FIG. 23A. (24A) The percent of ivCD45−CD8 T cells expressing the tissue residency/activation marker CD69 is shown for each animal. (24B) The percent of WCL-responsive (IFNγ+) CD8 T cells in the lung tissue (ivCD45−) following IV BCG. (24C) IFNγ production (black) as identified in (24B) is overlaid on total CD8 memory T cells (grey); percentages indicate the proportion of IFNγ+ CD8 T cells expressing CD69 and CD103.

The immunohistochemical analysis of lung sections revealed the presence of increased CD3+ T cells in the lung tissue 1 month after IV BCG. To extend the analysis and substantiate whether T cells isolated from lung lobes after IV BCG (FIGS. 20B, 20C) were tissue resident T cells (Trm), fluorescently-labeled anti-CD45 antibody was injected intravenously into two immunized NHP per vaccine group just prior to necropsy, a technique shown to delineate tissue-derived (ivCD45−) or vasculature-derived (ivCD45+) leukocytes in mice and NHP (Anderson et al. *Nat Prot* 9:209-222 (2014); Kauffman et al. *Muc Immunol* 11:462-473 (2018)). Ex vivo phenotypic analysis of CD69 expression (a marker of Trm and/or recent T cell activation) in combination with ivCD45 staining revealed that >80% of CD4 T cells (FIG. 23A) isolated from all lung lobes of IV BCG-immunized animals were derived from the lung parenchyma (CD69+ivCD45−). Of note, >10$^3$ CFU BCG were cultured from every lung lobe in this animal. In contrast, ID$_{high}$ and AE BCG vaccination resulted in 16%-35% CD69+ivCD45− CD4 T cells in the lung lobes with few or undetectable BCG (ID$_{high}$: 0 lobes with detectable BCG; AE: 2 lobes with 10$^2$-10$^3$ CFU). T cells from BAL in all animals were uniformly CD69+ivCD45−. Similar proportions of lung tissue- and lung vasculature-derived cells were observed in the CD8 T cell compartment of the same animals (FIG. 24A).

Figures 24B, 24C:
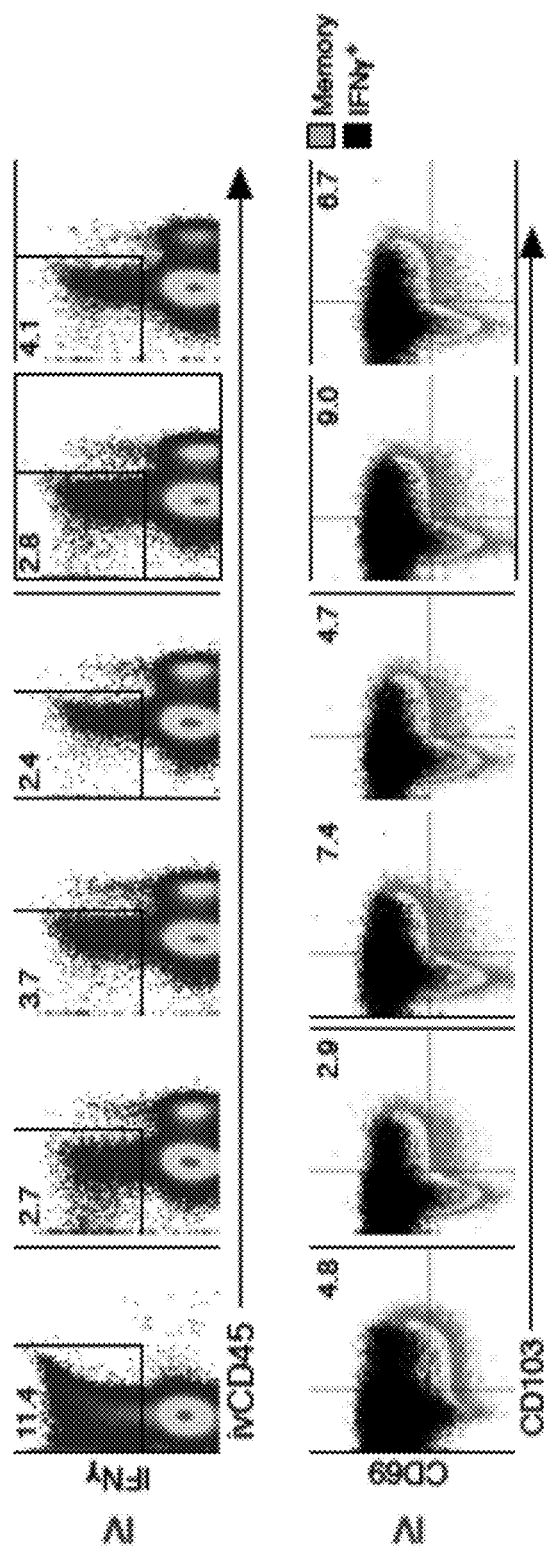
Figures 25A, 25B:
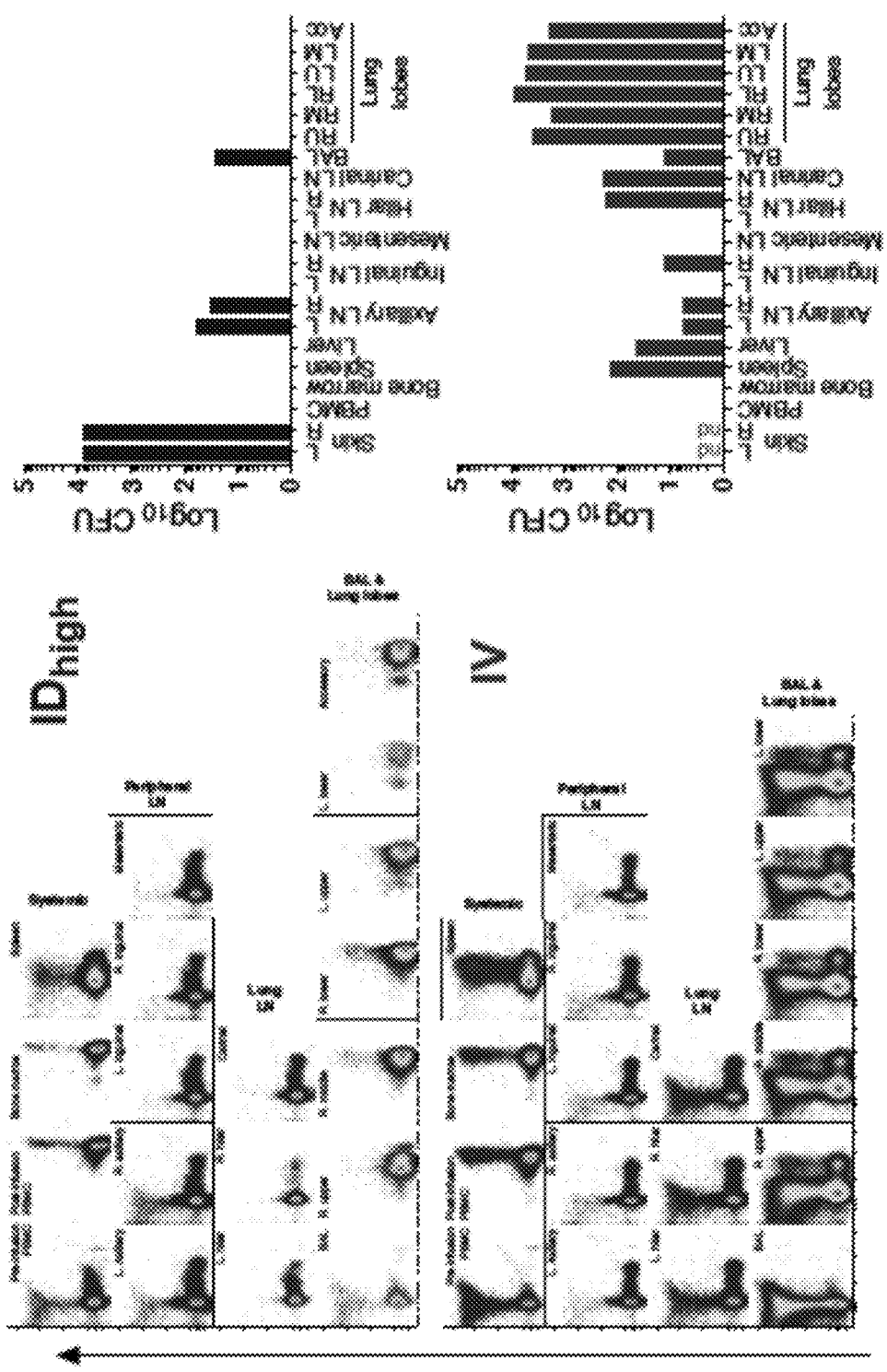
FIGS. 25A-25D—Discrimination between blood- and tissue-derived T cell responses in NHP 1 month after BCG immunization. NHP were immunized with 5×10⁷ CFU BCG ($ID_{high}$ (25A), IV (25B), AE (25C), EB (25D); cohort 6); BCG CFU and antigen-responsive T cells were measured in various tissues 1 month later. Prior to euthanasia, a fluorochrome-conjugated anti-CD45 antibody was injected intravenously (ivCD45) such that circulating (1465 intravascular) leukocytes were uniformly stained (ivCD45+) while leukocytes in the tissue remain protected from staining (ivCD45−). Following Mtb WCL-stimulation and intracellular cytokine staining, CD4 T cells were analyzed to determine if IFNγ secretion in each tissue was derived from the intravascular compartment (ivCD45+), the tissue compartment (ivCD45−), or both. FACS plots show memory CD4 T cells in all tissues collected from 1 of 2 NHP per vaccine group, organized by type/location (systemic, peripheral LN, lung LN, BAL and lung lobes). The BAL and lung responses from the IV BCG animal, shown in the bottom row of (25B) is reproduced from FIG. 23B. Pre-infusion PBMC indicates PBMC isolated from whole blood collected just prior to anti-CD45 injection. Bars show the number of BCG CFU in each respective tissue for each animal (color coded by vaccine), if detected.
Figures 25C, 25D:
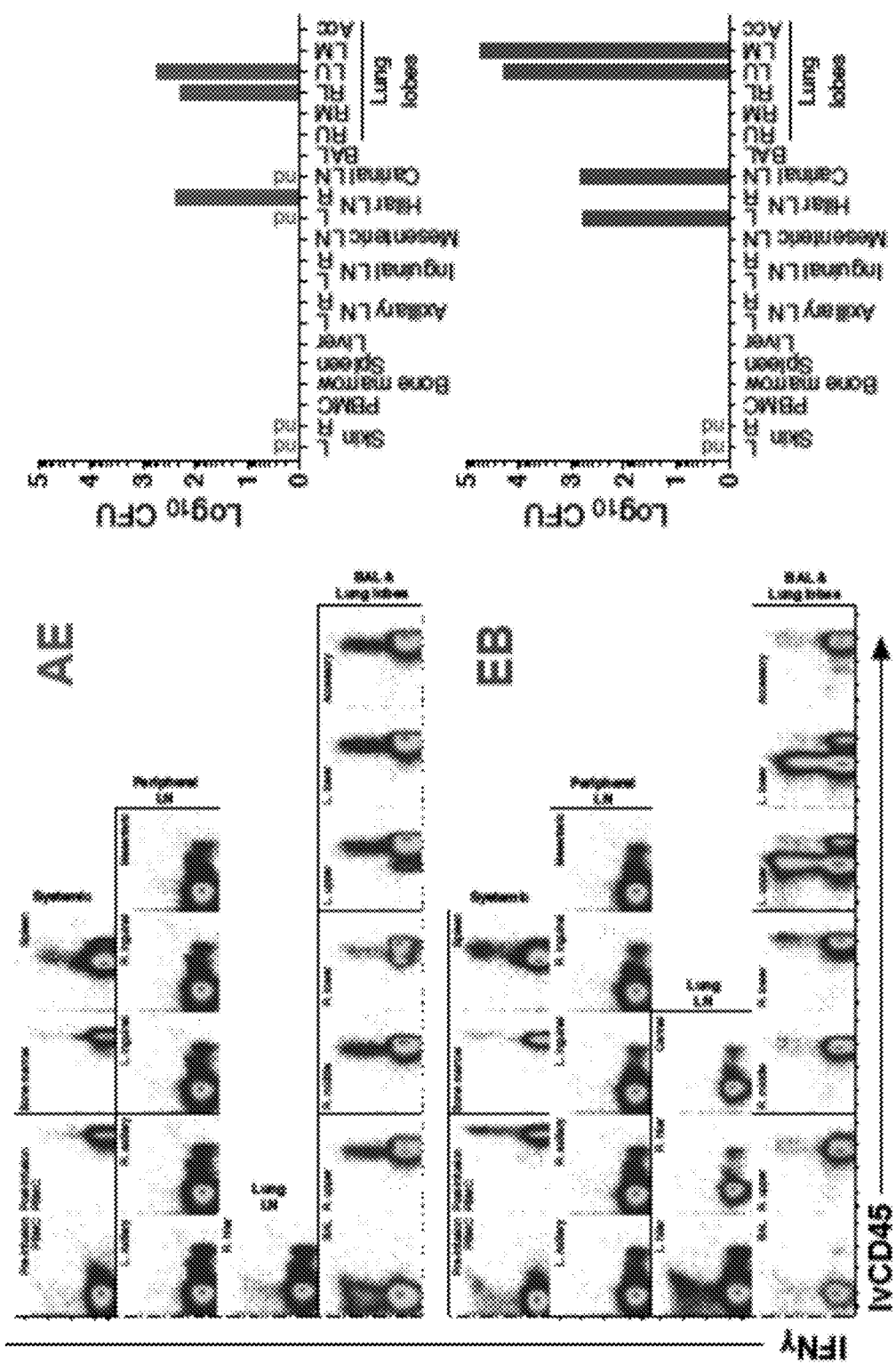
Figure 26:
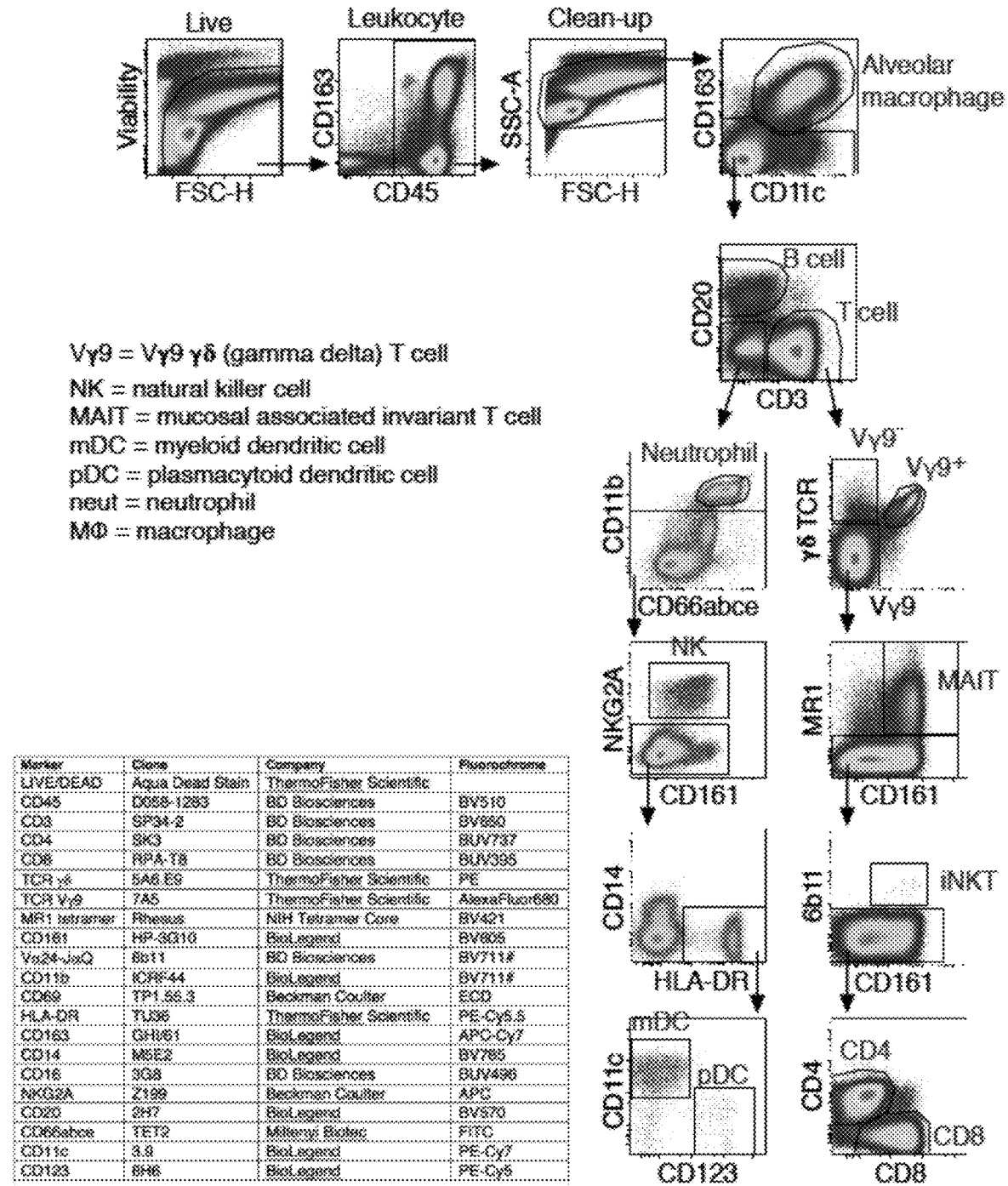
FIG. 26—Gating strategy to analyze cellular composition of BAL and PBMC after BCG. The gating strategy shown was used to determine the frequencies of leukocyte populations in the BAL and PBMC before and after BCG vaccination, as in FIGS. 1C-1E, 5B, and 7A-7B. Unstimulated cells were stained for viability and then surface-stained with remaining antibodies listed. A generous "live" gate was applied to include auto-fluorescent alveolar macrophages. CD45+ leukocytes were gated first, followed by CD163+ CD11c+ alveolar macrophages. From non-macrophages, CD20+ B cells, CD3+ T cells, and non-B, non-T cells were gated. T cells were further delineated as Vγ9+γd+ or Vγ9−γδ+ T cells, CD161+MR1+ MAIT cells, CD161+6b11+ iNKT cells (observed rarely in NHP BAL), and CD4+ or CD8+ T cells. Neutrophils (CD66abce+CD11b+) and NK cells (NKG2A+) were gated from non-B, non-T cells. HLA-DR+ cells were then gated as either CD11c+ myeloid dendritic cells (mDC) or plasmacytoid dendritic cells (pDC). In some samples, CD66abce alone was used to define neutrophils and Applicants cannot rule out eosinophil contamination. #indicates different markers conjugated to the same fluorochrome but used at different time points.
Figure 28A:
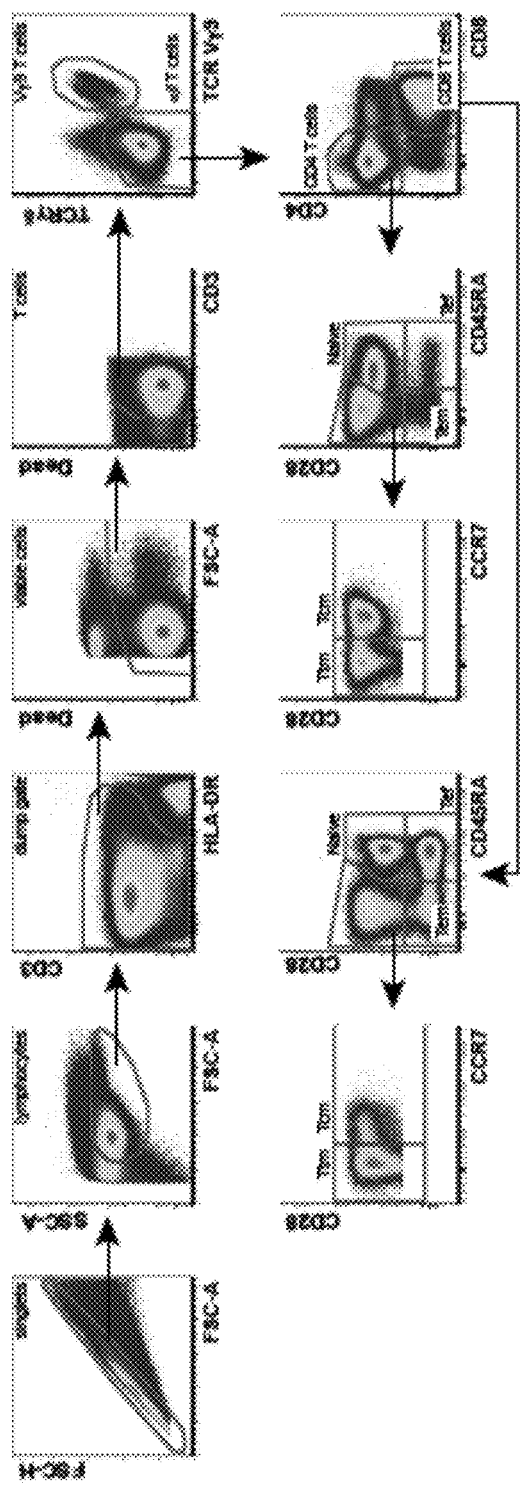
Figure 28B:
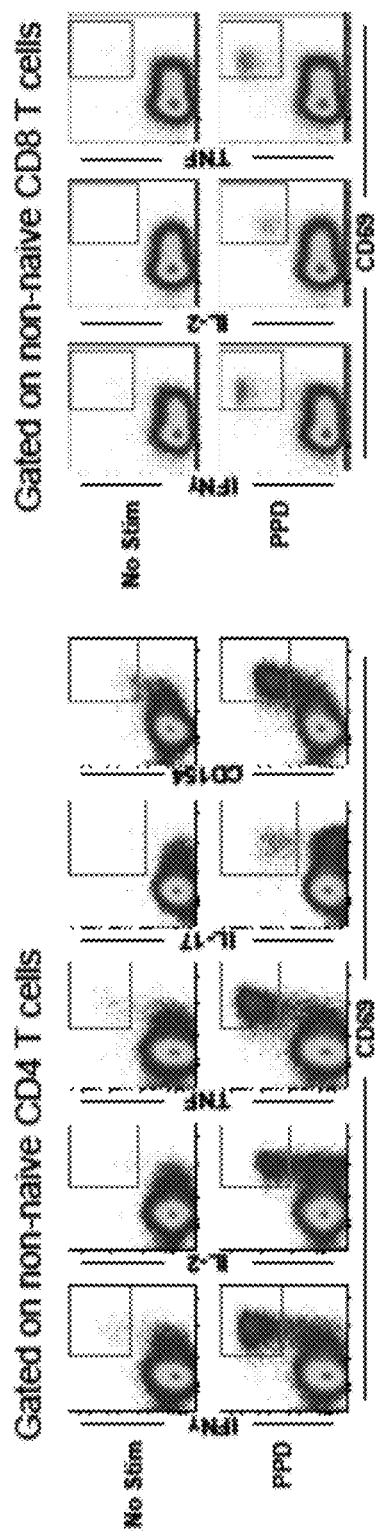

To investigate whether antigen-responsive T cells were located in the ivCD45− lung tissue compartment 1 month after BCG vaccination, cells isolated from lung lobes were restimulated in vitro with Mtb whole cell lysate (WCL) and analyzed by intracellular cytokine staining. Following IV BCG, ivCD45− IFNγ+CD4 and CD8 T cells were observed across all lung lobes (FIGS. 23B and 24B), as well as in the lung LN (FIGS. 25A-25D). Antigen-responsive T cells were largely CD69+ with a subset also expressing CD103 (a tissue homing marker expressed on some Trm (Masopust & Soerens *Annu Rev Immunol* 37:521-546 (2019)); FIGS. 23C and 24C). Thus, these cells may represent bona fide Trm, or recently-activated T cells due to the presence of BCG (FIGS. 20A and 23A). Overall, these data show that the vaccine route that provided the greatest level of protection (IV) had increased T cells throughout the lung tissue.

The increased detection of T cell responses in tissues containing BCG suggests alternative approaches to lung delivery may be critical for enhancing Trm. Indeed, a recent report that endobronchial instillation of BCG into the lower left lung lobe provides protection against repeated limiting-dose Mtb challenge in the same lobe (Dijkman et al. *Nat Med* 25:255-262 (2019)) suggests that direct mucosal delivery may be more efficacious than the AE approach used here. To determine whether direct instillation of BCG into the NHP lung would increase T cells in the lung parenchyma, BCG was instilled endobronchially (EB) into the left lung lobes. Strikingly, ~75% of CD4 and CD8 T cells isolated from the two left lung lobes were CD69+ivCD45−, compared to 7.1%-45% in the right lobes (FIGS. 23A and 24A). Furthermore, BCG CFU ($>10^4$) were detected only in the left lung lobes where the antigen-responsive CD4 T cells were also highest (FIGS. 25A-25D). Collectively, these data are consistent with FIGS. 20A-20C and suggest a general concordance between the presence of BCG in a given tissue following immunization and the detection of antigen-responsive T cells.

Example 8—Immune Associations of Bacterial Control

Figure 23D:
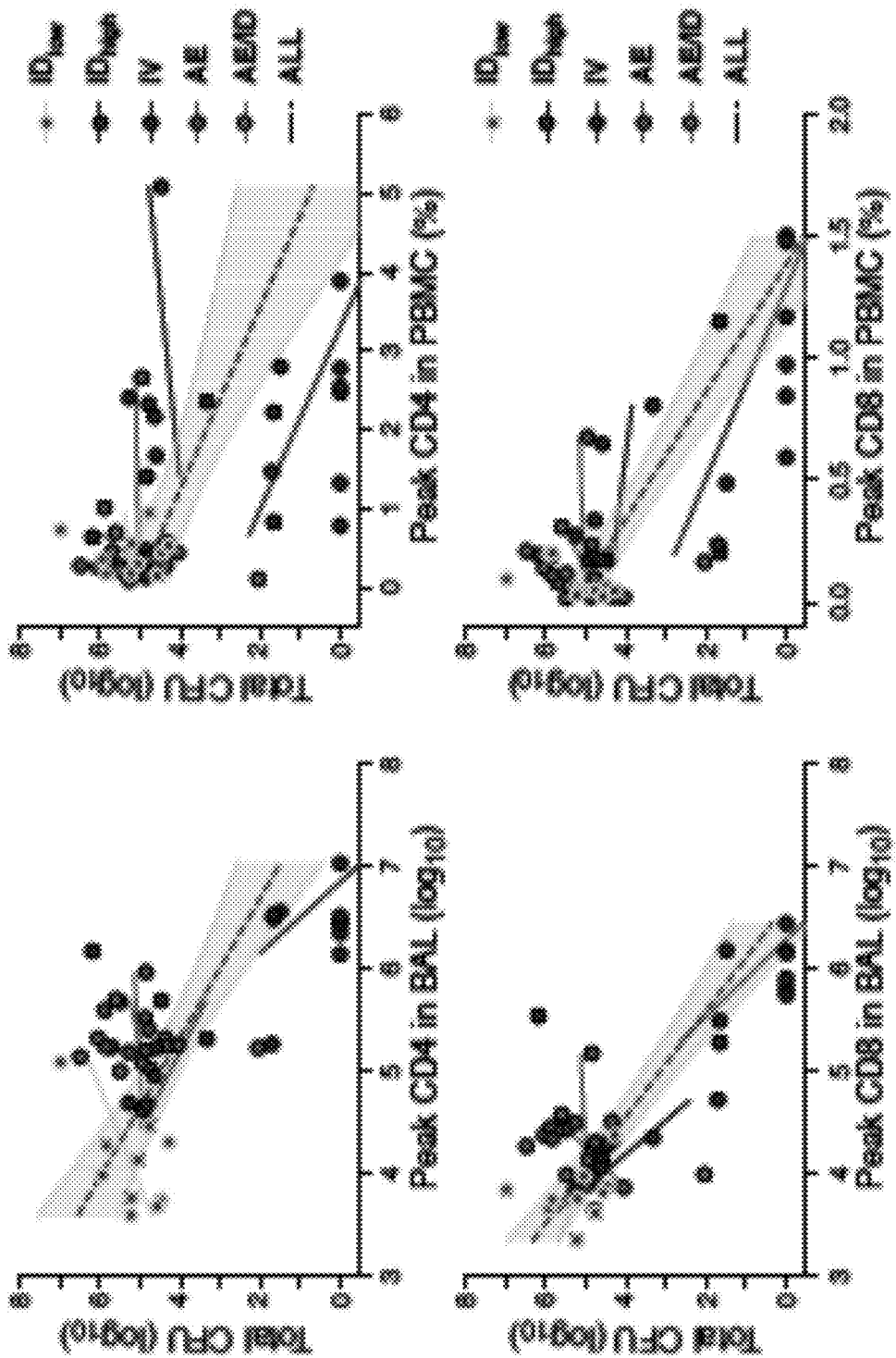

Based on the differences in immune responses and protection, several multiple regressions were used to test whether antigen-responsive CD4 or CD8 T cell numbers (BAL) or frequencies (PBMC) after immunization were associated with disease severity (CFU; FIG. 23D). Results indicate that when controlling for all vaccine routes, peak CD4 T cells in the BAL and PBMC, and peak CD8 T cells in the BAL do not have a significant association with total CFU. Of note, in PBMC, higher peak CD8 frequencies are associated with lower total CFU after controlling for route. Overall, these results show that the route of BCG vaccination is the primary determinant of Mtb control with IV being the only route that was significantly protective against TB (FIG. 18F).

Example 9—Discussion

Vaccines that prevent Mtb infection will have a major impact in limiting latent infection, active TB disease (primary or reactivated), and transmission (Harris et al. *Human Vaccines Immunother* 12:2813-2832 (2016)). This study provides a comprehensive immune analysis of how the route and dose of BCG influence vaccine-mediated protection in a highly susceptible rhesus model. The data demonstrating that IV BCG immunization results in markedly increased antigen-responsive T cells, including T cells throughout the lung parenchyma, and dramatic protection against Mtb challenge, represent a major step forward in the field of TB vaccine research.

Of 10 Mtb-challenged NHP that received IV BCG, 6 had sterilizing immunity (to the limits of detection by multiple criteria), and an additional 3 had <45 detectable Mtb bacilli at necropsy, a >1,000-fold reduction in CFU from the benchmark control of ID BCG vaccination. Thus, the IV vaccine route elicits robust and systemic immune responses that mediate durable protection. The data in FIG. 23A showing robust and localized T cell responses in lung tissue following direct BCG instillation provide a potential mechanistic difference between EB and AE delivery that could influence protection.

Only one other vaccine approach, a CMV vector encoding Mtb antigens and delivered subcutaneously, has shown substantive protection against Mtb challenge in a similar NHP infection model. In two separate studies, no TB lesions were detected by CT scanning in 1/7 and 13/27 animals (with 10/27 being Mtb culture-negative), after challenge with 25 and 10 CFU of Mtb, respectively, 6 months after the final immunization (Hansen et al. *Nat Med* 24:130-143 (2018)). The overall extent of TB infection and disease was reduced by 68% compared to unvaccinated controls. While T cell responses were induced comparably in all animals following CMV, protection was correlated with distinct innate signatures. Moreover, following CMV immunization and Mtb challenge, all animals, irrespective of protection, generated primary T cell responses to Mtb-specific antigens. By contrast, Applicants show here that there were low to undetectable antibody or T cell responses to Mtb antigens after challenge in the protected IV-immunized NHP. These data suggest potentially different mechanisms and kinetics by which these two vaccine platforms mediate protection.

A major focus of this study was to understand how the route and dose of BCG influence priming of T cell responses in tissues and blood. The delivery of BCG to the spleen, LN, and lungs following IV immunization led to the generation of a durable reservoir of peripheral memory cells in the spleen and bone marrow, as well as a high number of antigen-responsive T cells in the lung parenchyma. This contrasts with the far more localized BCG distribution and T cell immunity following ID and AE delivery. Future studies will determine the dose and duration of BCG persistence required to mediate protection after IV BCG to further understand the mechanisms of T cell priming.

There are at least three immune mechanisms for how IV BCG may mediate protection, compared to the other routes tested. First, since Mtb-responsive T cells are critical for control of infection in humans, the rapid elimination of Mtb may be due to the high magnitude of T cell responses in the lung tissue. The data presented here are consistent with studies in mice demonstrating the superior capacity of lung-localized Trm over circulating T cells to control TB disease (Sakai et al. *J Immunol* 192:2965-2969 (2014); Moguche et al. *J Exp Med* 212:715-728 (2015)) and NHP studies showing that depletion of lung interstitial CD4 T cells during SIV infection of latently-infected NHP is associated with reactivation and dissemination of pulmonary TB infection (Corleis et al. *Cell Reports* 26:1409-1418 (2019)). In addition to the role of conventional T cells, donor-unrestricted T cells can also respond to Mtb antigens and the transfer of γδ T cells in NHP reduced TB disease (Joosten et al. *Vaccine* 37:3022-3030 (2019); Qaqish et al. *J Immunol* 198:4753-4763 (2017)). While there was a transient increase in Vγ9+γδ T cells and MAIT cells in the BAL after IV BCG, such cells represented less than 10% of T cells in the BAL at the time of challenge. Second, antibodies might prevent or limit Mtb infection; however, while antibody levels were higher in BAL and plasma following IV BCG compared to the other routes of vaccination, they declined to pre-vaccination levels in the BAL at the time of challenge and were not boosted following challenge with Mtb. Although there is some evidence that antibodies can mediate control against Mtb in vivo or in vitro (Lu et al. *Cell* 167:433-443 (2016); Li et al. *Nat Rev Immunol* 18:591-596 (2018)), depletion of B cells prior to Mtb challenge in NHP did not alter overall disease progression (Phuah et al. *Infect Immun* 84:1301-1311 (2016)), and there is no evidence in any animal model that vaccine-induced antibody responses can prevent infection or provide protection to the extent shown here (Li et al. *Nat Rev Immunol* 18:591-596 (2018)). Third, macrophages could eliminate Mtb directly: a recent study in mice showed that access of high numbers of BCG to the bone marrow following IV BCG vaccination induced epigenetically modified macrophages with enhanced capacity to protect against Mtb infection (Kaufmann et al. *Cell* 172:176-190 (2018)) a process termed "trained immunity" (Joosten et al. *J Clin Invest* 128:1837-1851 (2018); Kleinnijenhuis et al. *J Innate Immun* 6:152-158 (2014)). Furthermore, PBMCs from humans recently exposed to Mtb or BCG can limit Mtb growth in vitro through innate and T cell activation (Joosten et al. *Vaccine* 37:3022-3030 (2019)). Here, Applicants were unable to detect BCG in the bone marrow of NHP, 1 month after IV BCG vaccination. Furthermore, in an initial analysis, there was no increased innate activation of PBMC to non-Mtb antigens following IV BCG, a hallmark of trained immunity. Nonetheless, it is possible that any of these three mechanisms might act independently or together to mediate protection. Future studies, in which IV BCG-immunized NHP are depleted of CD4 or CD8 T cells just prior to challenge, may provide the first direct evidence for their role in protection and help delineate the contribution of other mechanisms.

As 9 of 10 animals were protected by IV BCG immunization, Applicants were unable to define an immune correlate of protection within this group. Ongoing studies in which the dose of IV BCG is decreased to alter immunity and limit protection may reveal correlates and mechanisms of protection. Nevertheless, there were several unique quantitative and qualitative differences in the immune responses following IV BCG that may underlie protection. First, there were substantially higher frequencies and numbers of Mtb antigen-responsive CD4 Th1 and CD8 T cells in BAL and PBMC (FIGS. 9A-9D), with a small fraction of CD4 cells also producing IL-17. While CD4 T cells are more commonly associated with protection, CD8 T cells have also been shown to have a role in BCG-mediated protection in NHP (Chen et al. *PLoS Pathogens* 5, e1000392, doi: 10.1371/journal.ppat.1000392 (2009)). Second, the memory phenotype of responding CD4 T cells indicated greater differentiation based on the increased proportion of Ttm and Tem compared to Tcm in the blood and BAL (FIGS. 10E, 10F). This composition provides for both maintenance of durable memory cells and a population of effectors for rapid control (Soares et al. *J Infect Dis* 207:1084-1094 (2013)). Third, there was a unique CD4 T cell transcriptional profile in BAL, including upregulation of genes such as TNFSF8 (CD153) and IL-21R, which have been associated with protection against TB (Sallin et al. *Nat Microbiol* 3:1198-1205 (2018); Booty et al. *Scientific Rep* 6:36720 (2016)) (FIGS. 9F-9H). Fourth, and perhaps most striking, was the large population of T cells across all the lung parenchyma tissue which have a critical role in mouse models of Mtb (Sakai et al. *J Immunol* 192:2965-2969 (2014); Moguche et al. *J Exp Med* 212:715-728 (2015)) (FIGS. 23A and 24A). An important finding was that while BAL CD4 T cell responses were increased in $ID_{high}$, AE and AE/ID-immunized animals compared to $ID_{low}$, there were limited lung tissue responses and no increased protection. These data suggest that while measurement of BAL responses may provide additional insights into vaccine correlates compared to blood (Dijkman et al. *Nat Med* 25:255-262 (2019)), they may not accurately reflect lung Trm (Corleis et al. *Cell Reports* 26:1409-1418 (2019)) that may be the mechanism of protection. These findings have potentially important implications for using BAL to determine immune correlates and mechanisms of protection.

The results from this study have potential implications for clinical translation. A major milestone was reached last year in a clinical study investigating whether revaccination with the standard dose of ID BCG (the same as the $ID_{low}$ dose used in this study) could prevent Mtb infection in African adults. While BCG revaccination did not reduce the incidence of early Quantiferon conversion (a measure of Mtb infection), it did decrease sustained Quantiferon conversion (Nemes et al. *Nes England J Med* 379:138-149 (2018)). A larger follow-up study is planned to determine whether BCG ID revaccination can prevent disease. The striking finding here, that IV BCG prevents infection and disease against Mtb to a far greater extent than ID BCG, provides compelling data supporting clinical development for this route of immunization. In this regard, direct IV immunization with a live attenuated malaria vaccine has been demonstrated to be safe and feasible in several Phase I studies across multiple age groups in Africa (Jongo et al. *Am J Trop Med Hyg* doi:10.4269/ajtmh.18-0835 (2019)). A major consideration for this approach is the safety of IV BCG. Accordingly, transient clinical signs (elevated liver enzymes, globulin, and CRP), cellular perturbations in lung and lung LN, and increased spleen size were observed at the high dose of IV BCG administered here within the first month following immunization, but had normalized by the time of challenge.

In conclusion, this study provides a paradigm shift toward developing vaccines focused on preventing TB infection, which would also prevent latency, active disease, and transmission. Moreover, the data support preclinical testing of IV administration for other subunit platforms such as RNA or attenuated viral vectors to induce T cell responses in lung tissue. Finally, this study provides a benchmark against which future interventions should be tested and a new framework towards a better understanding of the immune correlates and mechanisms of protection against TB.

Example 10—Methods

Animals. Male and female Indian-origin rhesus macaques (*Macaca* mulatta) were used in these studies (FIG. 3A). All experimentation complied with ethical regulations at the respective institutions (Animal Care and Use Committees of the Vaccine Research Center, NIAID, NIH and of Bioqual, Inc., and of the Institutional Animal Care and Use Committee of the University of Pittsburgh). Animals were housed and cared for in accordance with local, state, federal, and institute policies in facilities accredited by the American Association for Accreditation of Laboratory Animal Care (AAALAC), under standards established in the Animal Welfare Act and the Guide for the Care and Use of Laboratory Animals. Animals were monitored for physical health, food consumption, body weight, temperature, complete blood counts, and serum chemistries. All infections were performed at the University of Pittsburgh where animals were housed in a Biosafety Level 3 facility.

The sample size for this study was determined using bacterial burden (measured as $\log_{10}$ of total thoracic CFU) as the primary outcome variable. Initially, BCG route efficacy was to be tested by comparing IV, AE, and AE/ID routes to $ID_{low}$ vaccination and it was found that 10 animals per group would be sufficient to obtain over 90% power and the type I error rate for 3 group comparisons was adjusted (alpha=0.0167). After initiation of the first cohort of NHP in this study, Applicants elected to test the effect of dose on ID vaccination by adding an $ID_{high}$ group (n=8). The additional treatment group did not substantially reduce the power of the study. In order to detect a 1.5 difference in total CFU ($\log_{10}$) with a pooled standard deviation of 0.8 (using prior data), Applicants obtained over 90% (90.7%) power using 10 animals per group with an adjusted type I error rate for 4 group comparisons (alpha=0.0125). The comparison made between the $ID_{high}$ (n=8) and $ID_{low}$ (n=10) groups achieved 85.6% power detecting the same difference (1.5 $\log_{10}$) and with an alpha=0.0125.

BCG vaccination. For Mtb challenge studies, 3-5-year-old rhesus macaques were randomized into experimental groups based on gender, weight, and pre-vaccination CD4 T cell responses to PPD in BAL. Animals were vaccinated at Bioqual, Inc. under sedation and in successive cohorts as outlined in FIG. 3A. BCG Danish Strain 1331 (Statens Serum Institut, Copenhagen, Denmark) was expanded (Fitzpatrick et al. *Tuberculosis* 114:47-53 (2019)), frozen at ~3×10$^8$ CFU ml$^{-1}$ in single-use aliquots and stored at –80° C. Immediately prior to injection, BCG (for all vaccine routes) was diluted in cold PBS containing 0.05% tyloxapol (Sigma-Aldrich) and 0.002% Antifoam Y-30 (Sigma-Aldrich) to prevent clumping of BCG and foaming during aerosolization (Saini et al. *Tuberculosis* 92:160-165 (2012)). ID BCG was injected in the left upper arm (5×10$^5$ CFU; $ID_{low}$) or split across both upper arms (5×10$^7$ CFU; $ID_{high}$) in a volume of 200 µl per site IV BCG (5×10$^7$ CFU) was injected into the left saphenous vein in a volume of 2 ml; AE BCG (5×10$^7$ CFU) was delivered in a 2 ml volume via pediatric mask attached to a Pari eFlow nebulizer (PARI Pharma GmgH) that delivered 4 µM particles deep into the lung, as described (Darrah et al. *npj Vaccines* 4, 21, doi: 10.1038/s41541-019-0113-9 (2019)); AE/ID animals were immunized simultaneously (5×10$^7$ CFU AE plus 5×10$^5$ CFU ID in left arm); EB BCG (5×10$^7$ CFU in 2 ml; cohort 6 only) was instilled into the left lung lobes using an endoscope. No loss of viability was observed for BCG after aerosolization. In pilot studies, lower doses of BCG were prepared and delivered as described above. Text refers to nominal BCG doses—actual BCG CFU for each vaccine group in every cohort were quantitated immediately after vaccination.

Mtb challenge. Animals were challenged by bronchoscope with 4-36 CFU barcoded Mtb Erdman (FIG. 3A) in a 2 ml volume as previously described (Martin et al. *mBio* 8, doi:10.1128/mBio.00312-17 (2017)). Infectious doses across this range result in similar levels of TB disease in unvaccinated rhesus (FIG. 3B). Clinical monitoring included regular monitoring of appetite, behavior and activity, weight, erythrocyte sedimentation rate (ESR), Mtb growth from gastric aspirate, and coughing. These signs, as well as PET CT characteristics, were used as criteria in determining whether an animal qualified as meeting humane endpoint prior to the pre-determined study end point.

PET CT scans and analysis. PET CT scans were performed using a microPET Focus preclinical PET scanner (Siemens Molecular Solutions) and a clinical eight-slice helical CT scanner (NeuroLogica Corporation) as previously described (White et al. *JoVE* doi:10.3791/56375 (2017); Maiello et al. *Infect Immun* 86, doi:10.1128/iai.00505-17 (2018); Lin et al. *Nat Med* 20:75-79 (2014); Coleman et al. *Infect Immun* 82:2400-2404 (2014)). 2-deoxy-2-($^{18}$F)Fluorodeoxyglucose (FDG) was used as the PET probe. Serial scans were performed prior to, 4 and 8 weeks after Mtb, and before necropsy (cohorts 1-3) or at 2 and 4 weeks after BCG (cohorts 5a, b). OsiriX MD (v.10.0.1), a DICOM (Digital Imaging and Communications in Medicine) image viewer, was used for scan analyses, as described (White et al. *JoVE* doi:10.3791/56375 (2017)). Lung inflammation was measured as total FDG activity within the lungs. A region of interest (ROI) was segmented which encompassed all lung tissue on CT and was then transferred to the co-registered PET scan. On the PET scan, all image voxels of FDG-avid pathology (Standard Uptake Value >2.3) were isolated and summated resulting in a value of cumulative SUV. To account for basal metabolic FDG uptake, total FDG activity was normalized to resting muscle resulting in a total lung inflammation value. Individual granulomas were counted on each CT scan. If granulomas were too small and numerous within a specific area to count individually or if they consolidated, quantification was considered to be too numerous to count (tntc). To measure the volume of the spleen, an ROI was drawn outlining the entire organ on each of the axial slices of the CT scan and the volume was computed across these ROIs (using a tool in OsiriX). Any scans for which visibility of the entire spleen was limited (n=2) were excluded from this analysis.

Necropsy, pathology scoring, and Mtb and BCG burden. For challenge studies (cohorts 1-3), NHP were euthanized 11-15 weeks after Mtb or at humane endpoint by sodium pentobarbital injection, followed by gross examination for pathology. A published scoring system (Maiello et al. *Infect Immun* 86, doi:10.1128/iai.00505-17 (2018)) was used to determine total pathology from each lung lobe (number and size of lesions), LN (size and extent of necrosis), and extrapulmonary compartments (number and size of lesions). Pre-necropsy PET CT scans were used to find lesions in the lungs. Each lesion (including granulomas, consolidations and clusters of granulomas) in the lung, all thoracic LNs, half of each lung lobe, and random samples of spleen and liver were homogenized to create single-cell suspensions. Suspensions were plated on 7H11 agar (Difco) and incubated at 37° C. with 5% $CO_2$ for 3 weeks for CFU enumeration or formalin-fixed and paraffin-embedded for histological examination. CFU were counted and summed to calculate the total thoracic bacterial burden for the animal (Maiello et al. *Infect Immun* 86, doi:10.1128/iai.00505-17 (2018); Gideon et al. *PLoS Pathogens* 11, e1004603, doi: 10.1371/journal.ppat.1004603 (2015); Phuah et al. *Infect Immun* 84:1301-1311 (2016)).

To determine BCG CFU, BAL, bone marrow aspirates, and blood were collected from animals prior to euthanasia. Individual lung lobes and thoracic and peripheral LN, spleen, liver, and the skin site(s) of injection (if applicable) were excised. 0.5 ml of blood and bone marrow and 10% of retrieved BAL wash fluid were plated; ~1 g of tissue (or one whole LN or skin biopsy) was processed in water in gentleMACS M Tubes (Miltenyi Biotec) using a gentleMACS Dissociator (Miltenyi Biotec). Samples were plated and counted as above. Data are reported as CFU ml$^{-1}$ of blood or bone marrow, CFU per total BAL collected, CFU per one LN or skin biopsy, CFU per lung lobe or spleen, or CFU per gram of liver. CFU for individual lung lobes and LN were averaged for each animal.

Rhesus blood, BAL, and tissue processing. Blood PBMC were isolated using Ficoll-Paque PLUS gradient separation (GE Healthcare Biosciences) and standard procedures; BAL wash fluid (3×20 ml washes of PBS) was centrifuged and cells were combined before counting, as described (Darrah et al. *npj Vaccines* 4, 21, doi:10.1038/s41541-019-0113-9 (2019)). LN were mechanically disrupted and filtered through a 70 µM cell strainer. Lung and spleen tissues were processed using gentleMACS C Tubes and Dissociator in RPMI 1640 (Thermo Fisher Scientific). Spleen mononuclear cells were further separated using Ficoll-Paque. Lung tissue was digested using collagenase, Type I (Thermo Fisher Scientific) and DNAse (Sigma-Aldrich) for 30-45 minutes at 37° C. with shaking, followed by passing through a cell strainer. Single-cell suspensions were resuspended in warm R10 (RPMI 1640 with 2 mM L-glutamine, 100 U ml-1 penicillin, 100 µg ml$^{-1}$ streptomycin, and 10% heat-inactivated FBS; Atlantic Biologicals) or cryopreserved in FBS containing 10% DMSO.

Multiparameter flow cytometry. Generally, longitudinal PBMC samples were batch-analyzed for antigen-specific T cell responses or cellular composition at the end of the study from cryopreserved samples, whereas BAL and tissue (necropsy) samples were analyzed fresh. PBMC were washed, thawed and rested overnight in R10 prior to stimulation, as described (Darrah et al. *npj Vaccines* 4, 21, doi:10.1038/s41541-019-0113-9 (2019)). For T cell stimulation assays, 1-5 million viable cells were plated in 96-well V-bottom plates (Corning) in R10 and incubated with R10 alone (background), or with 20 µg ml$^{-1}$ Tuberculin PPD (Statens Serum Institut, Copenhagen, Denmark), 20 µg ml$^{-1}$ H37Rv Mtb whole cell lysate (WCL; BEI Resources), or 1 µg ml$^{-1}$ each of ESAT-6 and CFP-10 peptide pools (provided by Aeras, Rockville, MD) for 2 hours before adding 10 µg ml$^{-1}$ BD GolgiPlug (BD Biosciences). The concentrations of PPD and WCL were optimized to detect CD4 T cell responses; however, protein antigen stimulation may underestimate CD8 T cell responses. For logistical reasons, fresh samples (BAL and tissues) were incubated overnight (14 hours total) and PBMC were incubated for 6 hours before intracellular cytokine staining. For cellular composition determination, cells were stained immediately ex vivo or after thawing. Antibody and tetramer information for each flow cytometry panel is listed on gating trees in FIGS. 26-29C. Generally, cells were stained as follows (not all steps apply to all panels, all are at room temperature): Wash twice with PBS/BSA (0.1%); 20-minute incubation with rhesus MR1 tetramer (Corbett et al. *Nature* 509:361-365 (2014)) (NIH Tetramer Core Facility) in PBS/BSA; wash twice with PBS; live/dead stain in PBS for 20 minutes; wash twice with PBS/BSA; 10-minute incubation with human FcR blocking reagent (Miltenyi Biotec); incubation with surface marker antibody cocktail in PBS/BSA containing 1× Brilliant Stain Buffer Plus (BD Biosciences) for 20 minutes; wash thrice with PBS/BSA (0.1%); 20 minute incubation BD Cytofix/Cytoperm Solution (BD Biosciences); wash twice with Perm/Wash Buffer (BD Biosciences); 30 minute incubation with intracellular antibody cocktail in Perm/Wash Buffer containing 1× Brilliant Stain Buffer Plus; wash thrice with Perm/Wash Buffer. For Ki-67 staining, samples were stained for surface markers and cytokines as described above, followed by nuclear permeabilization using eBioscience™ Foxp3/Transcription Factor Staining Buffer (Thermo Fisher Scientific) and incubation with antibody against Ki-67 following kit instructions. Data were acquired on either a modified BD LSR II or modified BD FACSymphony™ and analyzed using FlowJo software (v. 9.9.6 BD Biosciences). Gating strategies can be found in FIGS. 26-29C. All cytokine data presented graphically are background-subtracted.

Intravascular CD45 Staining. One month after BCG-vaccination, animals in cohort 6 (n=2 per vaccine group) received an IV injection of Alexa Fluor 647-conjugated anti-CD45 antibody (ivCD45; 60 µg/kg, clone MB4-6D6, Miltenyi Biotec) 5 minutes prior to euthanasia. Blood was collected prior to anti-CD45 injection as a negative control, and prior to euthanasia as a positive control. Animals underwent whole body perfusion with cold saline before tissue collection. Tissues were processed for BCG CFU quantification and flow cytometric analysis as described above. Staining panels used were as in FIGS. 26, 27A-27F, with the omission of the APC-conjugated antibodies.

Immunohistochemistry. Embedded tissue sections were deparaffinized (100% xylene, 10 minutes; 100% ethanol, 5 minutes; 70% ethanol, 5 minutes), boiled under pressure for 6 minutes in antigen retrieval buffer (1× Tris EDTA, pH 9.0), and cooled. Sections were blocked in PBS (1% BSA) in a humidified chamber at room temperature for 30 minutes followed by staining for CD3 (CD3-12, Abcam), CD11c (5D11, Leica), and CD20 (Thermo Scientific, RB-9013-PO) for 18 hours at 4° C. in a humidified chamber. After washing with PBS in coplin jars, sections were incubated for 1 hour at room temperature with conjugated anti-rabbit IgG Alexa Fluor 488 (Life Technologies, A21206), Anti-rat IgG Alexa Fluor 546 (Invitrogen, A11081), and anti-mouse IgG Alexa Fluor 647 (Jackson ImmunoResearch, 7 5606-150). After washing, coverslips were applied using Prolong Gold antifade with Dapi mounting media (Life Technologies). Slides were cured for 18-24 hours before imaging on an Olympus FluoView FV1000 confocal microscope. Lung sections were imaged and 2 random representative 1 mm$^2$ ROI from each animal were analyzed using CellProfiler™v2.2.0. Pipelines were designed for analysis by adding modules for individual channel quantification based on pixel intensity and pixel size providing a numerical value for each cell type and total cells.

Histologic analyses were performed by a veterinary pathologist (EK) in a blinded fashion on hematoxylin/eosin (H&E) stained sections from all tissues harvested. IFNγ ELISpots were performed at 0, 4, 6, and 8 weeks after Mtb and at necropsy. One day prior to use, hydrophobic high protein binding membranes 96-well plates (Millipore Sigma) were hydrated with 40% ethanol, washed with sterile water, and coated with anti-human/monkey IFNγ antibody (15 µg ml–1, MT126L, MabTech) overnight at 4° C. Plates were washed with HBSS and blocked with RPMI with 10% human AB serum for 2 hours at 37° C. with 5% $CO_2$. 200,000 PBMC well$^{-1}$ were incubated in RPMI supplemented with L-glutamate, HEPES and 10% human AB serum containing 2 µg ml$^{-1}$ ESAT-6 or CFP-10 peptide pools for 40-48 hours at 37° C. with 5% $CO_2$. Medium alone or phorbol 12,13-dibutyrate (12.5 µg ml$^{-1}$) plus ionomycin (37.5 µg ml$^{-1}$) were added as negative (background) and positive controls, respectively. To develop, plates were washed with PBS and biotinylated anti-human IFNγ antibody (2.5 µg ml$^{-1}$, 7-B6-1, MabTech) was added for 2 hours at 37° C. with 5% $CO_2$. After washing, streptavidin-horseradish peroxidase (1:100, MabTech) was added for 45 minutes at 37° C. with 5% $CO_2$. Spots were stained using AEC peroxidase (Vector Laboratories, Inc.) per the manufacturer's instructions and counted manually on an ELISpot plate reader. Data are reported as average ELISpots from duplicate background-subtracted wells. Wells with confluent spots were described as too numerous to count (tntc).

To measure innate cytokine production following BCG immunization as one assessment of trained immunity, cryopreserved PBMC were batch-analyzed. Cells were thawed and resuspended in warm R10. $5 \times 10^5$ cells well$^{-1}$ in 96-well V-bottom plates were rested overnight at 37° C. with 5% $CO_2$. Cells were resuspended in Trained Immunity Media (Kleinnijenhuis et al. *J Innate Immun* 6:152-158 (2014)) plus H37Rv Mtb whole cell lysate (BEI Resources, 20 µg ml-1), heat-killed *Staphylococcus aureus* (InvivoGen, $1 \times 10^6$ ml$^{-1}$), *Escherichia coli* LPS (Sigma-Aldrich, 1 ng ml$^{-1}$), or RPMI and incubated for 24 hours at 37° C. with 5% $CO_2$ before collecting supernatants. Cytokine and chemokine measurements were determined using a MILLIPLEX NHP cytokine multiplex kit per instructions (Millipore Sigma) and analyzed on a Bio-Plex Magpix Multiplex Reader (Bio-Rad).

Antibody ELISAs. IgG, IgA, IgM titers to Mtb H37Rv whole cell lysate were assessed in plasma and 10-fold concentrated BAL fluid. WCL was used based on greater sensitivity compared to PPD, culture filtrate protein, or lipoarabinomannan. 96-well MaxiSorp ELISA plates (Nunc) were coated overnight at 4° C. with 0.1 µg of WCL. Plates were blocked with PBS/FBS (10%) for 2 hours at room temperature and washed with PBS/TWEEN 20 (0.05%). 1:5 serially-diluted plasma or concentrated BAL fluid (8 dilutions per sample) was incubated at 37° C. for 2 hours, followed by washing. 100 µl of goat anti-monkey HRP-conjugated IgG h+1 (50 ng ml$^{-1}$; Bethyl Laboratories, Inc.), IgA α chain (0.1 µg ml$^{-1}$, Rockland Immunochemicals Inc.), or IgM α chain (0.4 µg ml$^{-1}$, Sera Care) was added for 2 hours at room temperature, followed by washing. 100 µl Ultra TMB substrate (Invitrogen) was added for 12 min followed by 100 µl 2N sulfuric acid. Data were collected on a Spectramax i3X microplate reader (Molecular Devices) at 450 nm using Softmax Pro and presented either as endpoint titer (reciprocal of last dilution with an OD above the limit of detection or 2× the OD of an empty well) at 0.2 for IgG and IgA, or midpoint titer for IgM where samples did not titer to a cutoff of 0.2.

Single-cell transcriptional profiling. High-throughput single-cell mRNA sequencing by Seq-Well was performed on single-cell suspensions obtained from NHP BAL, as previously described (Giehran et al. *Nat Methods* 14:395-398 (2017)). 15,000 viable cells per sample were applied directly to the surface of a Seq-Well device. At each time point after BCG, 2 arrays were run for each sample—one unstimulated and one stimulated overnight with 20 µg ml$^{-1}$ of PPD in R10.

Sequencing and alignment: Sequencing for all samples was performed on an Illumina Nova-Seq. Reads were aligned to the *M. mulatta* genome using STAR (Dobin et al. *Bioinformatics* 29:15-21 (2013)), and the aligned reads were then collapsed by cell barcode and unique molecular identifier (UMI) sequences using DropSeq Tools v1 to generate digital gene expression (DGE) matrices (Macosko et al. *Cell* 161:1202-1214 (2015)). To account for potential index swapping, Applicants merged all cell barcodes from the same sequencing run that were within a hamming distance of 1.

Analysis of single-cell sequencing data: For each array, Applicants assessed the quality of constructed libraries by examining the distribution of reads, genes and transcripts per cell (FIG. 14B). At each time point, Applicants next performed dimensionality reduction (PCA) and clustering as previously described (Satija et al. *Nat Biotechnol* 33:495-502 (2015); Wolf et al. *Genome Biol* 19, 15, doi:10.1186/s13059-017-1382-0 (2018)). Results were visualized in a 2-dimensional space using UMAP (Becht et al. *Nat Biotechnol* doi:10.1038/nbt.4314 (2018)), and each cluster was annotated based on the identity of highly expressed genes.

Module Identification: Data were subsetted on genes with significant PCA loadings that were determined through a randomization approach ('JackStraws') as input for WGCNA functions. Following the WGCNA tutorial (http:// Horvath.genetics.ucla.edu/html/Coexpression/Network/ Rpackages/WGCNA/Tutorials/); Applicants chose an appropriate soft power threshold to calculate the adjacency matrix. As scRNA-Seq data are zero-inflated, adjacency matrices with high power further inflate these zeros, and yield few correlated modules. Therefore, when possible, Applicants chose a power as suggested by the authors (i.e. the first power with a scale free topology above 0.8); however, if this power yielded few modules (fewer than 3), the power was decreased. An adjacency matrix was then generated using the selected soft power and it was transformed into a Topological Overlap Matrix (TOM). Subsequently, Applicants hierarchically clustered this TOM, and used the cutreeDynamic function with method 'tree' to modules using a dissimilarity threshold of 0.5 (i.e., a correlation of 0.5). To test for significance in correlation structure of the module, a permutation test was implemented. Binning the genes in the true module 786 by average gene expression (#bins=10), Applicants randomly picked genes with the same distribution of average expression from the total list of genes used for module discovery 10,000 times. For each of these random modules, the one-sided Mann-Whitney U test was performed between the distribution of dissimilarity values between the genes in the true module, and the distribution between the genes in the random module. Correcting the resulting P-values for multiple hypothesis testing by Benjamini-Hochberg FDR correction, Applicants considered the module significant if fewer than 500 tests (P<0.05) had FDR >0.05.

Gene Module Enrichments: To characterize the 7 significant gene modules, an enrichment analysis was performed using databases of gene expression signatures (Savant and GSEA/MsigDb). Specifically, the enrichments in the Savant database, which includes signatures from ImmGen, mouse body atlas, and other datasets (http://newpathways.mcdb.u-cla.edu/savant-dev/), were performed using genes included in significant modules and background expression set of 32,681 genes detected across single cells using Piano (va-remo.github.io/piano/).

Statistical Methods. Any data shown on a log scale was transformed by adding 1 to the entire dataset to ensure zeros could be seen in graphs. For continuous variables, vaccine routes were compared using a Kruskal-Wallis test with Dunn's multiple comparison adjustment or one-way ANOVA with Dunnett's multiple comparison adjustment (comparing all routes to $ID_{low}$ BCG). Fisher's exact tests were run for multiple CFU thresholds (evaluating protection) to assess the association between vaccine route and protection from Mtb (FIG. 18F). A permutation test (Roederer et al. *Cytometry. Part A: J Int Soc Anal Cytol* 79:167-174 (2011)) was used to compare fractional distributions (pie charts) of all vaccine groups to $ID_{low}$ BCG. For clinical parameters, combined pre-vaccination measurements from all animals were compared against distributions from every vaccine group at every time point using Dunnett's test for multiple comparisons. To assess whether post-vaccination antigen-responsive CD4 or CD8 T cells in the BAL or PBMC are associated with disease severity, Applicants first calculated peak T cell responses for each animal over the course of vaccine regimen. $Log_{10}$ transformed CD4 and CD8 cell counts were calculated within BAL and frequencies of CD4 and CD8 cells were calculated within PBMC. To assess the effects of vaccine route and T cells on total CFU ($log_{10}$ transformed), several multiple linear regressions were run in JMP® Pro (version 12.1.0). Cytokine production for trained immunity assay were compared using a 2-way ANOVA and Dunnett's multiple comparison test. Serial PBMC responses to CFP, ESAT-6 or CFP-10 by IFNγ ELISpot were analyzed by using a Wilcoxon signed-rank test to compare pre-infection versus 12 weeks post-infection time points (within each vaccine route).

Data Availability. All relevant data are available from the corresponding author upon reasonable request. RNA-sequencing data that support this study have been deposited in the Gene Expression Omnibus (GEO), accession number GSE132527.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of eliciting an enhanced immune response comprising administering intravenously (IV) to a subject in need of prophylactic treatment of *Mycobacterium tuberculosis* (MTB) a pharmaceutical formulation comprising one or more modulating agents and Bacille Calmette-Guerin (BCG), wherein the one or more modulating agents are selected from the group consisting of an RNA encoding one or more MTB antigens selected from Ag85A and Ag85B, a viral vector encoding one or more MTB antigens selected from Ag85A and Ag85B, and one or more MTB antigens selected from Ag85A and Ag85B, and wherein the one or more modulating agents increase expression of IFNγ, IL-2, TNF, and/or IL-17 in systemic and/or lung T cells; and
   confirming an enhanced immune response was elicited in the subject, thereby providing an enhanced immune response for prophylactic treatment, by:
   detecting an increased fractional or absolute number of Vγ9$^+$ γδ T cells in a blood sample obtained from the subject; or
   detecting an increased proportion of transitional (Ttm) memory cells compared to Central (Tcm) memory cells in a blood sample obtained from the subject.

2. The method of claim 1, wherein the viral vector is an attenuated viral vector.

* * * * *